United States Patent [19]

Matsunaga et al.

[11] Patent Number: 5,821,258
[45] Date of Patent: Oct. 13, 1998

[54] PHENYLBENZIMIDAZOLE DERIVATIVES

[75] Inventors: Akio Matsunaga; Yuki Nakajima; Hiroshi Kohno; Hiroshi Ohkouchi; Daiji Iwata; Hajime Edatsugi, all of Chiba-ken, Japan

[73] Assignee: Mitsui Chemicals, Inc., Tokyo, Japan

[21] Appl. No.: 577,262

[22] Filed: Dec. 22, 1995

[30] Foreign Application Priority Data

Dec. 27, 1994 [JP] Japan .................................. 6-325429

[51] Int. Cl.⁶ ..................... A61K 31/415; C07D 235/18; C07D 403/12
[52] U.S. Cl. .................... 514/394; 548/306.1; 548/310.7
[58] Field of Search ............................ 548/306.1, 310.7; 514/394

[56] References Cited

U.S. PATENT DOCUMENTS 5,273,991  12/1993  Lee ......................................... 514/397

FOREIGN PATENT DOCUMENTS

| 0148431 | 7/1985 | European Pat. Off. . |
| 0194529 | 9/1986 | European Pat. Off. . |
| 0209707 | 1/1987 | European Pat. Off. . |
| 0246868 | 11/1987 | European Pat. Off. . |
| WO93/13739 | 7/1993 | WIPO . |

OTHER PUBLICATIONS

Arcamone et al, "Synthesis, DNA–Binding Properties, and Antitumor Activity of Novel Distamycin Derivatives", *J. Med. Chem.*, 1989, 32, pp. 774–778.

Oesterle et al, "Chemical Modifications of Aminonaphthalenesulfonic Acid Derivatives Increase Effectively and Specificity of Reverse Transcriptase Inhibition and Change Mode of Action of Reverse Transcriptase and DNA Polymerase Alpha Inhibition", *Antiviral Research*, 1993, vol. 22, No. 2–3, pp. 107–119.

F. Arcamone et al, "Structure and Synthesis of Distamyci A", *Nature*, vol. 203, pp. 1064–1065, 1964.

Teng et al, "The Molecular Structure of the Complex of Hoechst 33258 and the DNA Dodecamer d(CGCGAAT-TCGCG)", *Nucleic Acids Research*, vol. 16, pp.2671–2690, 1988.

Baker et al, "Sequence–Specific Cleavage of Double–Helical DNA. N–Bromoacetyldistamycin", *J. Am. Chem. Soc.*, vol. 107, pp. 8266–8268, 1985.

Fukui et al, "Methioninemethylsulfonium Salts", *Fukui, Kanai, and Kitano*, vol. 25, pp. 804–807, 1959.

Valu et al, "DNA–Directed Alkylating Agents. 3. Structure–Activity Relationships for Acridine–Liked Aniline Mustards: Consequences of Varying the Length of the Linker Chain", *J. Med. Chem.*, vol. 33, pp. 3014–3019, 1990.

Palmer et al, "Hypoxia–Selective Antitumor Agents. 3. Relationships Between Structure and Cytotoxicity Against Cultured Tumor Cells for Substituted N,N–Bis(2–chloroethyl)anilines", *J. Med. Chem.*, vol. 33, pp. 112–121, 1990.

Everett et al, "Aryl–2–Halogenoalkylamines, Part II", *Everett and Ross*, 420, pp. 19720–1983, 1948.

Alley et al, "Feasibility of Drug Screening With Panels of Human Tumor Cell Lines Using a Microculture Tetrazolium Assay", *Cancer Research*, vol. 48, pp. 589–601, 1988.

Sklyarova et al., Khim.–Farm. Zh. (1988), 22(6), pp. 697–699 and CA 110:192707 (1989).

Sklyarova et al., J. Org. Chem. USSR, 25 (1989), 1.2, pp. 169–171.

*Primary Examiner*—Johann Richter
*Assistant Examiner*—Laura L. Stockton
*Attorney, Agent, or Firm*—Burns, Doane, Swecker & Mathis, L.L.P.

[57] ABSTRACT

Described herein is an anticancer agent, an antiviral agent or an antimicrobial agent which contains, as an active ingredient for acting on DNA, a compound presented by the following formula (1) or its pharmacologically acceptable salt:

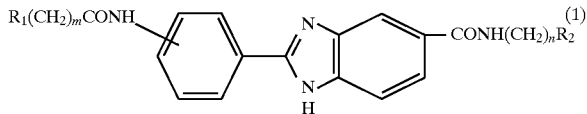

29 Claims, No Drawings

PHENYLBENZIMIDAZOLE DERIVATIVES

BACKGROUND OF THE INVENTION

1. Field of the Invention

The present invention relates to compounds which are novel phenylbenzimidazole derivatives which bond to DNA and inhibit the growth of cells, and it also relates to the application of these derivatives to medicinal compositions, particularly anticancer agents, antimicrobial agents and antiviral agents.

2. Description of the Related Art

Some of compounds which act on DNA can be used as anticancer agents. For example, adriamnycin has been useful as an anticancer agent which intercalates DNA. Furthermore, compounds such as cisplatin and mitomycin which react with DNA have also often been used. Such an anticancer function based on the action on DNA can be considered to be established to some extent, though all of the function cannot be elucidated. On the other hand, in recent years, distamycin and netropsin have been noticed as substances which bond to DNA to exert an anti-tumor activity [Nature, Vol. 203, p. 1064–1065 (1964)]. Much attention has been paid to these substances as groove binders which are different from the conventional anticancer agents in a bonding mechanism to DNA. In addition, a compound such as Hoechst 33258 [Nucleic Acids Research, Vol. 16, p. 2671–2690 (1988)] is also known whose bond to DNA has already been confirmed.

However, it cannot be presently presumed at all from the knowledge regarding the conventional anticancer agents what moiety of each anticancer agent is an actually necessary structure or what other structure can be substituted. Nevertheless, it is valuable to predict and search the presence of another compound having a desirable structure. Such a search of the new structure is considered to be particularly required for the creation of a novel anticancer agent.

Moreover, compounds in which an alkylating agent is bonded to the distamycin derivatives are known, and typical examples of such compounds are described in J. Am. Chem. Soc., Vol. 107, p. 8266 (1985), EP 246868, WO 93-13739, J. Med. Chem., Vol. 32, p. 774 (1989), and the like. Other compounds are also known in which an alkylating agent is bonded to a compound similar to the distamycin (U.S. Pat. No. 5,273,991). In several of these compounds, a bis(2-chloroethyl)amino residue is used as the alkylating agent, but it is already known that this residue is a part of the structure of the anticancer agent. For example, chlorambucil is known as the anticancer agent having the bis(2-chloroethyl)amino residue in its molecule. The anticancer activity of this compound is presumed to be the result of its alkylation to DNA, an enzyme or the like. However, the merit of adding the alkylating agent having a chloroethylamine structure as a partial structure of the anticancer agent which bonds to DNA has scarcely been recognized so far.

The above-mentioned distamycin is a typical example of the compounds which bond to DNA, but compounds which have benzimidazole in each molecule and which can bond to DNA are also known. For example, Hoechst 33258 has a structure containing two benzimidazoles, a phenol and a piperazine. In this compound, however, a feature that aromatic rings are bonded via amide bonds as in the distamycin is not present. Comparing these structures with each other, the structures which can bond to DNA are definitely different from each other. That is to say, the structures capable of bonding to DNA can be classified into some groups, but there has not been found any report in which the evaluation of their usefulness is made.

SUMMARY OF THE INVENTION

The present inventors have searched a novel structure in expectation of the presence of a compound which has a structure other than known compounds, partially maintaining the structure of benzimidazole and which has an anticancer function. As a result, novel compounds having a structure, in which a phenyl group is directly bonded to benzimidazole and another substituent is added via an amide bond, have been selected as useful anticancer agents. Above all, 1H-2-phenylbenzimidazole-5-carboxamide derivatives have been particularly selected. These compounds possess novel structures. Furthermore, these compounds show an inhibitory activity on tumor cell growth equal to that of distamycin in vitro. This activity as the anticancer agent has also been newly found by the present inventors.

The activity as the anticancer agent can probably be enhanced by the addition of an alkylating agent. This has been simultaneously investigated, and as a result, it has been apparent that a compound containing the alkylating agent exerts a higher anti-tumor activity as compared with another compound containing no alkylating agent. It has been understood from this fact that the compound having the skeleton of phenylbenzimidazole can become a highly-active anticancer agent by adding the alkylating agent into the molecule of the compound.

On the basis of the above-mentioned knowledge, the prevent inventors have completed the invention of novel anticancer agents.

An object of the present invention is to provide a novel compound which acts on DNA, or a novel compound which has a partial structure capable of acting on DNA and which is useful as the anticancer agent.

A compound of the present invention which can achieve the above-mentioned object is a compound represented by the following formula (1) or its pharmacologically acceptable salt:

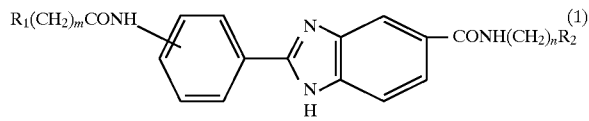

wherein each of m and n is independently an integer of from 0 to 5; each of $R_1$ and $R_2$ is independently a hydrogen atom, a halogen atom, an alkylthio group having 1 to 8 carbon atoms, preferably 1 to 4 carbon atoms, an amino group which may be substituted, an ammonium group which may be substituted, a sulfonium group which may be substituted, a phenyl group which may be substituted, a hetero-five-membered ring group which may be substituted, a hetero-six-membered ring group which may be substituted, an amidino group, a guanidino group, an amino acid residue or a group represented by the formula (2)

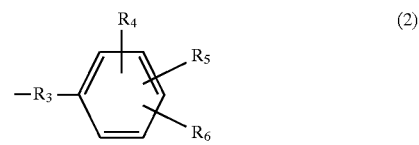

wherein $R_3$ is a direct bond or an oxygen atom {when $R_3$ is an oxygen atom, m or n of $(CH_2)_m$ or $(CH_2)_n$ to which $R_3$ bonds is not 0}; $R_4$ is a hydrogen atom, an alkyl group having 1 to 8 carbon atoms, an alkoxy group having 1 to 8 carbon atoms, a halogen atom, a trifluoromethyl group, a cyano group, an amidino group, a carboxyl group or —$COR_7$ wherein $R_7$ is an alkylamino group having 1 to 8 carbon atoms which may be substituted by a substituted amino group, an amino group which may be substituted by a phenyl group which may be substituted, or a benzylamino group which may be substituted; $R_5$ is a hydrogen atom, an alkyl group having 1 to 8 carbon atoms, an alkoxy group having 1 to 8 carbon atoms or a halogen atom; $R_6$ is a —$(CH_2)_pN(R_8)_2$ or —$(CH_2)_pNR_8R_9$ wherein p is an integer of from 0 to 5; $R_8$ is —$CH_2CH_2W$ wherein W is a halogen atom, a hydroxyl group, a mesyloxy group or a tosyloxy group or —$OCOR_7$ wherein $R_7$ is as defined above; $R_9$ is an alkyl group having 1 to 5 carbon atoms or a mesyl group; and the phenyl group having a $R_1(CH_2)_mCONH$ group can be substituted by the $R_1(CH_2)_mCONH$ group at any position, preferably at the 3-position or the 4-position of the phenyl group.

The compound of the present invention acts on DNA, and so it is useful as an active ingredient of an anticancer agent, an antiviral agent or an antimicrobial agent.

DETAILED DESCRIPTION OF THE INVENTION

AND PREFERRED EMBODIMENTS

Now, the present invention will be described in more detail.

In the formula (1), examples of "a halogen atom" represented by $R_1$ or $R_2$ include Cl, Br and I.

Examples of "an amino group which may be substituted" represented by $R_1$ or $R_2$ include an amino group, monoalkylamino groups and dialkylamino groups substituted by a straight-chain or a branched alkyl group having 1 to 8 carbon atoms. As the dialkylamino groups, those having the alkyl groups of 1 to 4 carbon atoms are desirable. Above all, a methylamino group, ethylamino group, n-propylamino group, isopropylamino group, n-butylamino group, dimethylamino group, diethylamino group, dipropylamino group and diisopropylamino group are desirable.

Examples of "an alkylthio group having 1 to 8 carbon atoms" represented by $R_1$ or $R_2$ include straight-chain and branched alkylthio groups having 1 to 8 carbon atoms, and typical suitable examples thereof include a methylthio group, ethylthio group, n-propylthio group, isopropylthio group, n-butylthio group, isobutylthio group, t-butylthio group, n-pentylthio group, n-hexylthio group, n-heptylthio group and n-octylthio group.

Examples of "an ammonium group which may be substituted" represented by $R_1$ or $R_2$ include a trimethylammonium group, a triethylammonium group and ammonium groups represented by the following formulae (3-1) to (3-14):

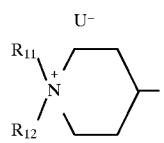 (3-1)

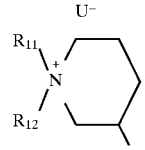 (3-2)

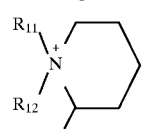 (3-3)

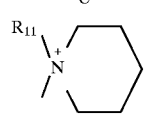 (3-4)

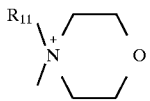 (3-5)

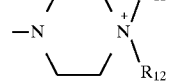 (3-6)

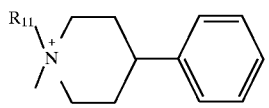 (3-7)

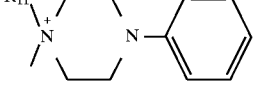 (3-8)

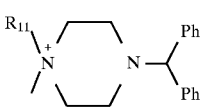 (3-9)

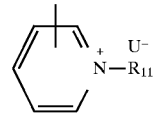 (3-10)

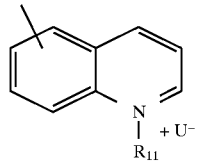 (3-11)

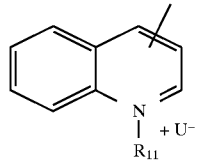 (3-12)

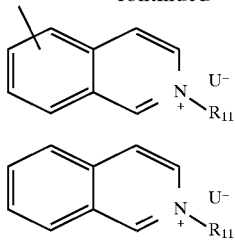 (3-13)

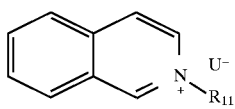 (3-14)

The acid residue bound to the above "ammonium group which may be substituted" is required to be usable as a portion of drug, and examples of the acid residue include inorganic acid residues such as hydrogen chloride, hydrogen iodide, hydrogen bromide, tetrafluoroboric acid, perchloric acid and phosphoric acid, organic sulfonic acid residues such as methanesulfonic acid, toluenesulfonic acid, camphorsulfonic acid and 1,5-naphthalenedisulfonic acid, and carboxylic acids such as lactic acid, maleic acid and malonic acid. In these formulae, each of $R_{11}$ and $R_{12}$ is independently a straight-chain or a branched alkyl group having 1 to 8 carbon atoms, and suitable examples thereof include a methyl group, ethyl group, n-propyl group, isopropyl group, n-butyl group, isobutyl group, t-butyl group, n-pentyl group, n-hexyl group, n-heptyl group and n-octyl group.

Examples of "a sulfonium group which may be substituted" represented by $R_1$ or $R_2$ include sulfonium groups substituted by a straight-chain or a branched alkyl group having 1 to 3 carbon atoms, and typical examples thereof include a dimethylsulfonium group, diethylsulfonium group, methylethylsulfonium group, methylpropylsulfonium group, diisopropylsulfonium group, methylisopropylsulfonium group, and sulfonium groups represented by the formulae (4-1) or (4-2):

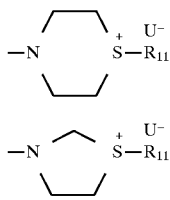 (4-1)

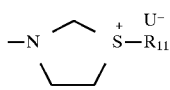 (4-2)

The acid residue bound to the above "sulfonium group which may be substituted" is required to be usable as a portion of drug, and examples of the acid residue include inorganic acid residues such as hydrogen chloride, hydrogen iodide, hydrogen bromide, tetrafluoroboric acid, perchloric acid and phosphoric acid, organic sulfonic acid residues such as methanesulfonic acid, toluenesulfonic acid, camphorsulfonic acid and 1,5-naphthalenedisulfonic acid, and carboxylic acids such as lactic acid, maleic acid and malonic acid. In these formulae, $R_{11}$ is a straight-chain or a branched alkyl group having 1 to 8 carbon atoms, and suitable examples thereof include a methyl group, ethyl group, n-propyl group, isopropyl group, n-butyl group, isobutyl group, t-butyl group, n-pentyl group, n-hexyl group, n-heptyl group and n-octyl group.

Examples of "a phenyl group which may be substituted" represented by $R_1$ or $R_2$ include a phenyl group which may be substituted with at least one of halogen atoms (a fluorine atom, a chlorine atom, a bromine atom and an iodine atom); straight-chain and branched alkyl groups having 1 to 5 carbon atoms; straight-chain and branched alkoxy groups having 1 to 3 carbon atoms; alkoxycarbonyl groups having 2 to 4 carbon atoms; a trifluoromethyl group; a cyano group; an amidino group; a guanidino group and dialkylamino groups in which the alkyl groups have 1 to 3 carbon atoms, respectively. Suitable examples thereof include a chlorophenyl group, dichlorophenyl group, trichlorophenyl group, bromophenyl group, dibromophenyl group, tribromophenyl group, fluorophenyl group, difluorophenyl group, trifluorophenyl group, methylphenyl group, ethylphenyl group, n-propylphenyl group, isopropylphenyl group, n-butylphenyl group, isobutylphenyl group, t-butylphenyl group, n-pentylphenyl group, methoxyphenyl group, ethoxyphenyl group, n-propyloxyphenyl group, isopropyloxyphenyl group, methoxycarbonylphenyl group, ethoxycarbonylphenyl group, n-propyloxycarbonylphenyl group, trifluoromethylphenyl group, cyanophenyl group, amidinophenyl group, guanidinophenyl group, dimethylaminophenyl group, diethylaminophenyl group, dipropylaminophenyl group, methoxyphenyl group and 3,4,5-trimethoxy group. In the case of monosubstitution, the position of the substituent on the phenyl group is the 2-, 3- or 4-position; in the case of disubstitution, the positions of the substituents thereon are two positions of the 2-, 3-, 4-, 5- and 6-positions; and in the case of trisubstitution, the positions of the substituents thereon are three positions of the 2-, 3-, 4-, 5- and 6-positions, unless otherwise noted.

Examples of "a hetero-five-membered ring group which may be substituted" represented by $R_1$ or $R_2$ include a pyrrolyl group, furyl group, thienyl group, imidazolyl group, oxazolyl group, pyrazolyl group, thiazolyl group, isothiazolyl group, isoxazolyl group, pyrrolinyl group, imidazolidinyl group, pyrazolidinyl group, pyrazolinyl group, furazanyl group, tetrahydrofuranyl group, triazolyl group and tetrazoyl group.

Examples of "a hetero-six-membered ring group which may be substituted" represented by $R_1$ or $R_2$ include a pyridyl group, pyrimidinyl group, pyranyl group, pyrazinyl group, pyridazinyl group, piperidyl group, piperazinyl group, thiomorpholino group, 4-methyl-1-piperazino group, 4-benzyl-1-piperazino group, 1-morpholino group, 1-piperidino group, 4-piperidino group and 4-methyl-1-piperidino group.

Here, in the above-mentioned "a hetero-five-membered ring group which may be substituted" and "a hetero-six-membered ring group which may be substituted", the passage "may be substituted" means that this group may be substituted by, for example, a halogen atom (a fluorine atom, a chlorine atom, a bromine atom or an iodine atom), a straight-chain and branched alkyl group having 1 to 5 carbon atoms, a straight-chain and branched alkoxy group having 1 to 5 carbon atoms, an alkoxycarbonyl group having 2 to 4 carbon atoms, a haloalkyl group having 1 to 3 carbon atoms, a cyano group, an amidino group and/or a dialkylamino group having 1 to 3 carbon atoms.

"An amino acid residue" as $R_1$ or $R_2$ is defined specially in the present invention as a group which can be obtained by omitting a carboxyl group from an amino acid. Suitable examples of this amino acid include arginine, histidine and lysine.

"A direct bond" represented by $R_3$ means that the substituted or non-substituted phenyl group in the formula (2) is directly bonded via no $R_3$.

Examples of a halogen atom represented by $R_4$ or $R_5$ in the formula (2) include F, Cl, Br and I.

Suitable examples of a halogen atom of W in —$CH_2CH_2W$ represented by $R_8$ include Cl and Br.

Preferable examples of an alkyl group having 1 to 8 carbon atoms represented by $R_4$ or $R_5$ include a methyl group, ethyl group, n-propyl group, isopropyl group, n-butyl group, isobutyl group, t-butyl group, n-pentyl group, n-hexyl group, n-heptyl group and n-octyl group.

Preferable examples of an alkoxy group having 1 to 8 carbon atoms represented by $R_4$ or $R_5$ include a methoxy group, ethoxy group, n-propyloxy group, isopropyloxy group, n-butoxy group, isobutoxy group, t-butoxy group, n-pentyloxy group, n-hexyloxy group, n-heptyloxy group and n-octyloxy group.

Preferable examples of "an alkylamino group which may be substituted by a substituted amino group" represented by $R_7$ include a dimethylaminoethyl group, dimethylaminopropyl group, dimethylaminobutyl group, diethylaminoethyl group, diethylaminopropyl group, diethylaminobutyl group, dipropylaminoethyl group, dipropylaminopropyl group, dipropylaminobutyl group, diisopropylaminoethyl group, diisopropylaminopropyl group and diisopropylaminobutyl group.

Preferable examples of "an amino group which may be substituted by a phenyl group which may be substituted" represented by $R_7$ include aniline, 4-dimethylaminoaniline and 4-chloroaniline.

Preferable examples of "a benzylamino group which may be substituted" represented by $R_7$ include benzylamine and 4-dimethylaminobenzylamine.

As a pharmacologically acceptable salt, any salt is acceptable, so far as it is usable as a drug, and examples of the pharmacologically acceptable salt include inorganic acid salts such as hydrochlorides, hydrobromates, hydroiodates, sulfates, nitrates and phosphates, and organic acid salts such as methanesulfonates, toluenesulfonates, camphorsulfonates, acetates, fumarates, maleates, citrates, oxalates and tartrates.

Next, the compounds represented by the formula (1) will be classified into groups A and B, and typical preparation processes thereof will be described.

Group A: A compound in which $R_1$ is a hydrogen atom, a halogen atom or a group represented by the formula (2), or its pharmacologically acceptable salt.

Group B: A compound in which $R_2$ is a hydrogen atom, a halogen atom or a group represented by the formula (2), or its pharmacologically acceptable salt.

In the undermentioned description and examples, the following abbreviations represent the corresponding compounds:

"DCC" . . . N,N'-dicyclohexylcarbodiimide,
"CDI" . . . N,N'-carbonyldiimidazole,
"HOSu" . . . N-hydroxysuccinimide,
"EDCI" . . . 1-(3-dimethylaminopropyl)-3-ethylcarbodiimide hydrochloride,
"DECP" . . . Diethyl cyanophosphonate,
"HOBt" . . . 1-hydroxybenzotriazole,
"DMAP" . . . 4-dimethylaminopyridine,
"DMF" . . . Dimethylformamide,
"THF" . . . Tetrahydrofuran,
"DMSO" . . . Dimethyl sulfoxide,
"IPA" . . . Isopropanol,
"chlorambusyl" . . . 4-[4-{bis(2-chloroethyl)amino}phenyl]butyric acid, and "Pd/C" . . . Active carbon with palladium (usually, a palladium content is 5–10%).

I. Synthesis of an intermediate

As shown in the following reaction formula (1), an aldehyde of the formula (6) and 3,4-diaminobenzoic acid or its ester of the formula (7) are heated at a temperature of from 100° C. to a reflux temperature, preferably at 130° to 200° C. in nitrobenzene, and the temperature of the reaction system is then returned to room temperature. A produced 1H-2-phenylbenzimidazole-5-carboxylic acid derivative or its ester derivative represented by the formula (5) can be collected by filtration:

Reaction formula (1):

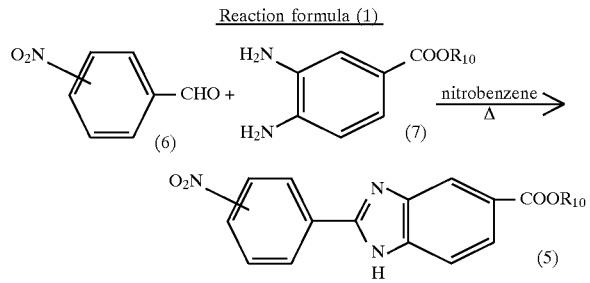

Here, when the ester is obtained, this ester can be hydrolyzed as shown in the following reaction formula (2), thereby obtaining a 1H-2-phenylbenzimidazole-5-carboxylic acid derivative represented by the formula (8):

Reaction formula (2):

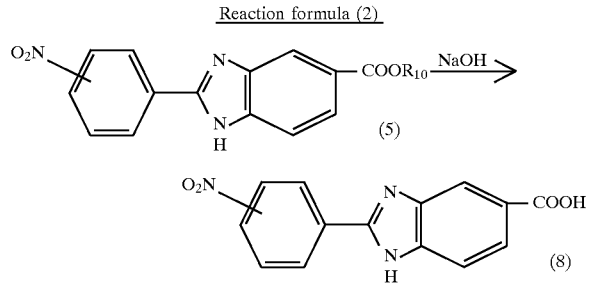

No particular restriction is put on the amounts of the aldehyde of the formula (6) and the 3,4-diaminobenzoic acid ester of the formula (7), but in general, the amount of the latter is in the range of from 80 to 120 mol parts with respect to 100 mol parts of the former. The reaction in nitrobenzene is carried out by the heating, until the starting materials have disappeared, while the progress of the reaction is observed, but in either case, a heating time of 5 to 100 hours leads to successful results. The heating may be carried out continuously or intermittently, but the total heating time should be in the above-mentioned range. The hydrolysis of the ester can be accomplished by heating the ester in the presence of sodium hydroxide or potassium hydroxide in a mixed solvent of water and ethanol or water and methanol. In this case, a ratio of water is in the range of from 5 to 90% by weight, but a ratio of from 40 to 60% by weight can give good results. A heating temperature is in the range of from 50° C. to a reflux temperature.

Concretely, if 3-nitrobenzaldehyde or 4-nitrobenzaldehyde is selected as the starting material, 1H-2-(3-nitrophenyl)benzimidazole-5-carboxylic acid or 1H-2-(4-nitrophenyl)benzimidazole-5-carboxylic acid can be synthesized by the same procedure as described above. The compound represented by the formula (8) can be used for the synthesis of compounds in the groups A and B.

II. Synthesis of a compound in the group A

As shown in the following reaction formula (3), for example, an amino compound represented by the formula (9) having $R_2$ [which is as defined above in the case of the formula (1)] is bonded to a carboxylic acid represented by the formula (8) in the presence of a suitable condensing agent such as DCC, CDI, EDCI or DECP to obtain an intermediate of the formula (10). Next, the nitro group of this intermediate is reduced to a corresponding amino compound of the formula (11) by catalytic hydrogenation, and this amino compound is then reacted with a carbonyl compound represented by the formula (12) having $R_1$ [which is a hydrogen atom, a halogen atom or a group represented by the formula (2)] to synthesize a compound of the formula (1) in the group A:

Reaction formula (3):

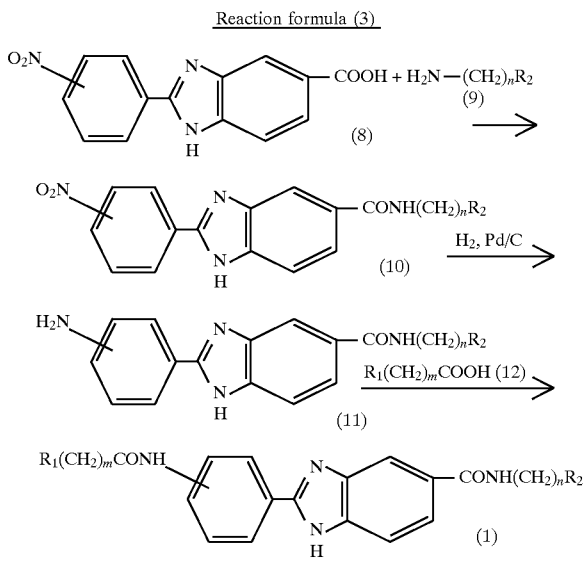

As a solvent for use in the bonding of the amino compound of the formula (9) and the carboxylic acid of the formula (8) in the presence of the condensing agent, various kinds of solvents are usable, but DMF or a mixed solvent containing DMF leads to relatively good results. The reaction is preferably carried out in the range of from −5° to 30° C. During the reaction, the progress of the reaction can be observed, but a reaction time is usually in the range of from 1 to 50 hours.

As the amino compound represented by the formula (9) having $R_2$, there can be used a compound synthesized from known compounds by combining known reactions, or a commercially available reagent. For example, when dimethylaminopropylamine, diethylaminopropylamine or dipropylaminopropylamine is used as the compound of the formula (9), a product can be obtained in which $R_2$ is a substituted amino group. Alternatively, when methylthiopropylamine, ethylthiopropylamine, propylthiopropylamine or butylthiopropylamine is used, an alkylthio group can be introduced into $R_2$. Furthermore, when aminopropyltrimethylammonium or aminopropyltriethylammonium is used, a trimethylammonium group or a triethylammonium group can be introduced into $R_2$. The phenyl group which may be substituted, the hetero-five-membered ring group which may be substituted, or the hetero-six-membered ring group which may be substituted can be introduced into $R_2$ of the compound in the group A by using the compound of the formula (9) in which $R_2$ is the group to be introduced.

A compound in which $R_2$ is an amidino group can be synthesized as follows.

As shown in the following reaction formula (4), the carboxylic acid of the formula (8) is first reacted with β-aminopropionitrile to obtain a reaction mixture containing a compound of the formula (13).

At this time, a usual condensing agent such as DCC, CDI, EDCI or DECP can be used. A method in which HOBt or HOSu is added to DCC can also be used. The reaction is suitably carried out at 0° to 30° C.

Next, this reaction mixture is suspended in ethanol, and a hydrogen chloride gas is then fed. Afterward, the resultant crystal is collected by filtration, and then dissolved or suspended in a solvent. An ammonia gas is further introduced into the solution to obtain a desired amidino compound represented by the formula (14). In this case, the solvent is preferably ethanol or a mixed solvent of ethanol and methanol. In the mixed solvent, the ratio of ethanol can optionally be selected in the range of from 10 to 100%. If this amidino compound is used as the compound of the formula (10) in the reaction formula (3), the compound of the group A in which $R_2$ is an amidino group can be obtained:

Reaction formula (4):

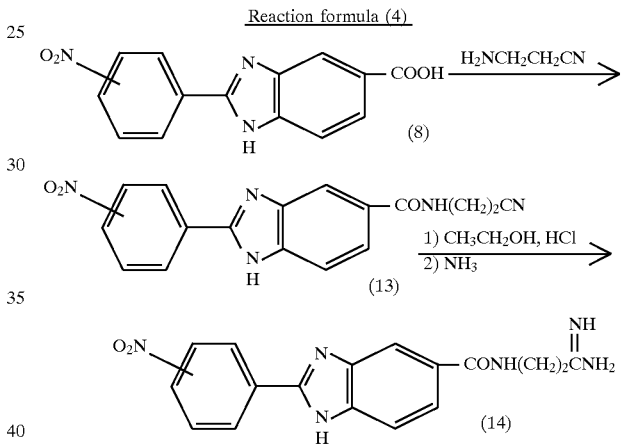

Typical examples of the compound of the formula (8) in the reaction formulae (3) and (4) include 1H-2-(3-nitrophenyl)benzimidazole-5-carboxylic acid or 1H-2-(4-nitrophenyl)benzimidazole-5-carboxylic acid.

Next, reference will be made to a synthesis method of a compound in which $R_1$ is a desired group.

For example, a compound in which $R_1$ is a substituent represented by the formula (2) can be synthesized by a process shown by the following reaction formula (5):

Reaction formula (5):

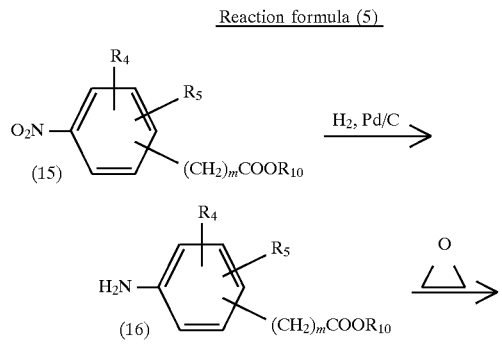

-continued
Reaction formula (5)

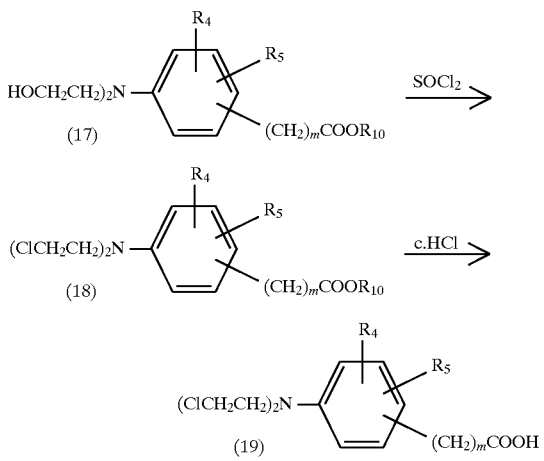

In the first place, a carboxylic acid ester derivative having a nitro group of the formula (15) is reduced to a corresponding amino compound of the formula (16) by catalytic hydrogenation using Pd/C as a catalyst. At this time, methanol, ethanol, DMF and the like can be used singly or in the form of a mixture of two or more thereof as a solvent. The reaction is preferably carried out at a temperature of from 0° to 30° C. A reaction time is in the range of from 30 minutes to 2 hours.

As the carboxylic acid derivative represented by the formula (15) which can be used herein, there can be used a compound synthesized from known compounds by known reactions, or a commercially available reagent.

Next, the thus produced amino compound of the formula (16) is reacted with ethylene oxide to obtain a compound of the formula (17). At this time, a mixture obtained by mixing a solvent such as water, THF, dichloromethane or benzene and acetic acid at an optional ratio can be used as a solvent. The reaction is preferably carried out at a temperature of from −20° to 120° C. A reaction time is suitably in the range of from 1 to 50 hours.

Furthermore, the OH group of the compound of the formula (17) is replaced with a Cl group by the use of a suitable reagent such as thionyl chloride, oxalyl chloride, phosphorus pentachloride, phosphorus oxychloride, mesyl chloride (in DMF), a combination of mesyl chloride and sodium chloride, a combination of mesyl chloride and lithium chloride, or dichlorotriphenylphosphorane, thereby obtaining a compound of the formula (18). The reaction is carried out at a temperature of from 0° to 100° C. A reaction time is in the range of from 20 minutes to 5 hours. In this case, a usual solvent such as chloroform, benzene or toluene can be used. Moreover, this solvent can be mixed with DMF. When thionyl chloride or oxalyl chloride is used, the reaction can be done under conditions of non-solvent.

The compound represented by the formula (18) can be hydrolyzed with an acid to obtain a carboxylic acid derivative represented by the formula (19). For example, the hydrolysis can be successfully accomplished with concentrated hydrochloric acid by heating at a temperature of from 80° C. to a reflux temperature. A reaction time is suitably in the range of from 30 minutes to 5 hours.

When this compound of the formula (19) is used as the compound of the formula (12) in the reaction formula (3), the compound of the group A in which $R_1$ is a substituent represented by the formula (2) can be obtained.

For example, the compound represented by the formula (11) can be bonded to the compound represented by the formula (19) by the use of a suitable condensing agent such as DCC, CDI, EDCI or DECP. In this case, a conventional solvent is usable, but DMF or a mixed solvent containing DMF leads to relatively good results. The reaction is preferably carried out in the range of from −5° to 30° C. During the reaction, the progress of the reaction can be observed, but a reaction time is usually in the range of from 1 to 50 hours. Alternatively, the compound of the formula (19) can be treated with thionyl chloride or oxalyl chloride in a conventional solvent (e.g., methylene chloride, chloroform, toluene and DMF can be used singly or in the form of a mixture of two or more thereof) to obtain an acid chloride, and this product can be then reacted with the compound represented by the formula (11) to bond them to each other. Here, the reaction is preferably carried out in the range of from −5° to 30° C. During the reaction, the progress of the reaction can be observed, but a reaction time is usually in the range of from 1 to 50 hours.

Another side chain represented by $R_1$ can also be prepared by using commercially available reagents and several steps of known reactions.

III. Synthesis of a compound in the group B

In the first place, an introduction method of $R_2$ will be described.

First, a technique of introducing $R_2$ will be described.

To start with, reference will be made to the synthesis of a compound in which $R_2$ is, for example, a substituent represented by the formula (2).

The introduction of $R_6$ into the substituent represented by the formula (2) can usually be achieved by either of the following two methods.

Method A:

As shown in the following reaction formula (6), a halogenated benzene derivative (in the formula (20), F is shown as an example of a halogen atom) containing a nitro group and suitable substituents which is represented by the formula (20) is reacted with N,N-bis(2-hydroxyethyl)amine to obtain a compound of the formula (21). In this time, DMSO is used as a solvent, and a reaction temperature is in the range of from 20° to 150° C. A reaction time is preferably in the range of from 30 minutes to 10 hours. As the halogenated benzene derivative containing the suitable substituents, there can be used a commercially available reagent or a compound which can be synthesized by the use of a known reaction. For example, the halogenated benzene derivative containing an amidino group can be introduced from a halogenated benzene derivative containing a cyano group by the utilization of a known reaction.

Next, the thus obtained intermediate of the formula (21) is reacted with a suitable chlorinating agent such as thionyl chloride, oxalyl chloride, phosphorus pentachloride, phosphorus oxychloride, mesyl chloride or a combination of mesyl chloride (in DMF) and sodium chloride to obtain a chloride of the formula (22). The reaction is carried out at 0° to 150° C., and a reaction time is in the range of from 5 minutes to 5 hours. As a solvent, there can be used a usual solvent such as chloroform, benzene or toluene. Furthermore, such a solvent can be mixed with DMF. In addition, the reaction can be done under non-solvent.

Reaction (6):

Reaction formula (6)

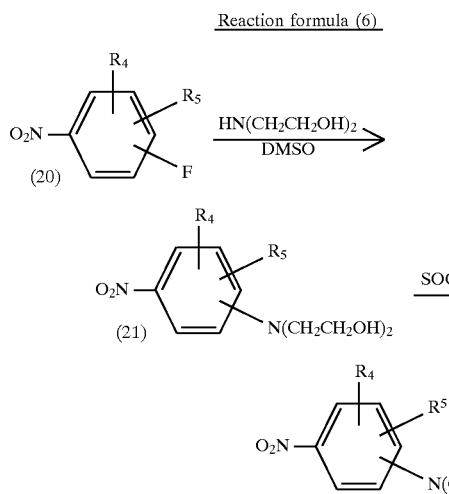

Method B:

As shown in the following reaction formula (7), an aniline derivative (in the case that p is 0) or an aminoalkylbenzene derivative (in the case that p is 1 or more) having a nitro group and suitable substituents which is represented by the formula (23) is reacted with ethylene oxide to obtain a compound of the formula (24). As a solvent at this time, there can be used a mixture obtained by mixing a solvent such as water, THF, dichloromethane or benzene with acetic acid at an optional ratio. The reaction is suitably carried out at −20° to 120° C., and a reaction time is suitably in the range of from 1 to 50 hours. As the aniline derivative or the aminoalkylbenzene derivative having the nitro group and the suitable substituents, there can be used a commercially available reagent or a compound which can be synthesized by the use of a known reaction.

Next, the compound of the formula (24) can be chlorinated with a suitable chlorinating agent such as thionyl chloride, oxalyl chloride, phosphorus pentachloride, phosphorus oxychloride, mesyl chloride (in DMF) or a combination of mesyl chloride and sodium chloride to obtain a compound of the formula (25). The reaction is suitably carried out at 0° to 150° C., and a reaction time is in the range of from 5 minutes to 5 hours. As a solvent, there can be used a conventional solvent such as chloroform, benzene or toluene. Furthermore, such a solvent can be mixed with DMF. In addition, the reaction can be done under non-solvent in the case of thionyl chloride or oxalyl chloride.

Reaction (7):

Reaction formula (7)

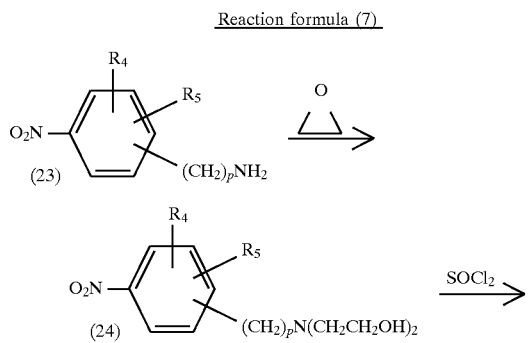

-continued
Reaction formula (7)

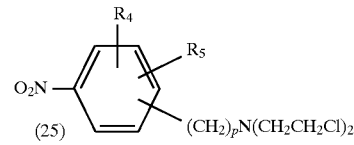

Each of the compounds of the formula (22) and (25) obtained in the above-mentioned methods A and B can be further subjected to the following reaction to introduce the substituent represented by the formula (2) into the compound in the group B.

In the first place, each of these compounds (nitro compounds) is catalytically hydrogenated to obtain a corresponding amino compound. A reaction formula in which the compound of the formula (22) is used is as follows.

Reaction formula (8):

Reaction formula (8)

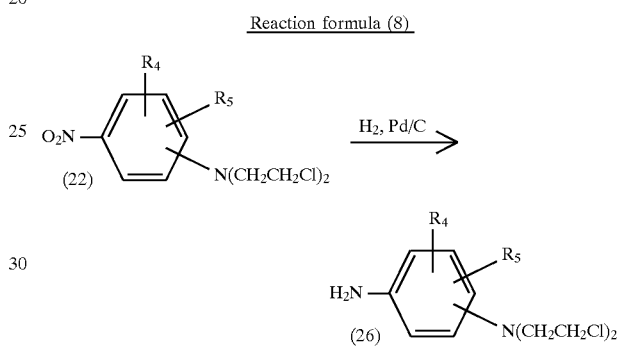

The nitro compound of the formula (25) can also be converted into the amino compound in the same manner.

When hydrochloric acid is added in an amount equal to or more than mols of the nitro compound, usually in an amount of from 1 to 1.2 mols at the catalytic hydrogenation, the amino compound can be stably obtained. The catalytic hydrogenation is suitably carried out at 5° to 30° C., and a solvent to be used, a conventional solvent can be used. For example, DMF or a mixed solvent of DMF and methanol is desirable. The ratio of DMF in this mixed solvent can be selected in the range of from 5 to 100%, preferably from 20 to 100%.

For the synthesis of the corresponding amino compound from the usual nitrobenzene derivative, there is usually employed the catalytic hydrogenation using Pd/C as a catalyst or a process utilizing a reaction in which tin chloride and hydrochloric acid are used. In particular, as the reduction method of the above-mentioned nitrobenzene derivative to which N,N-bis(2-chloroethyl)amino group is bonded, there is known a reduction method using tin chloride and hydrochloric acid, as reported in, for exam- ple, J. Chem. Soc. p. 1972–1983 (1949) or J. Med. Chem. Vol. 33, p. 112 to 121 (1990).

However, in place of this usual method, the following technique can also be used to efficiently perform the reduction reaction, and some treatments subsequent to the reaction can easily be accomplished advantageously. That is to say, the nitro compound which is the starting material is dissolved in a suitable solvent, for example, a single solvent or a mixed solvent of ethanol, methanol, ethyl acetate, THF and DMF, and Pd/C is then added in an amount corresponding to 0.5 to 50% by weight of the nitro compound, followed by hydrogenation at room temperature under atmospheric pressure, to obtain the corresponding amino compound. At this time, hydrochloric acid can be added in an amount equal to or more than mols of the nitro compound, usually in an amount of from 1 to 1.2 mols. The catalyst is removed by filtration and the solvent is then distilled off, followed by a treatment with one or more kinds of suitable solvents such as ethanol, IPA and ether, whereby a desired hydrochloride can be simply obtained.

Furthermore, as shown in the following reaction formula (9), an amino compound of the formula (28) can be synthesized from a carboxylic acid of the formula (27) in accordance with a process shown in J. Med. Chem. Vol. 33, p. 3014–3019 (1990).

Reaction formula (9):

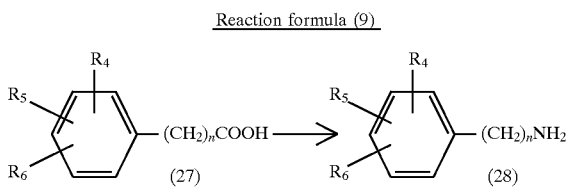

By the use of this process, an aminoalkylbenzene derivative can be synthesized in which $R_3$ is a chain having two or more methylene groups.

Here, the compound of the formula (26) corresponds to the compound of the formula (28) in which n is 0 and $R_6$ is an N,N-bis(2-chloroethyl)amino group. In the following description, therefore, reactions using the compound having the formula (28) will be referred to, but needless to say, the compound of the formula (26) can be used as the compound of the formula (28).

As shown in the reaction formula (10), a benzimidazole derivative of the formula (8) is bonded to the amino compound of the formula (28) in the presence of a conventional condensing agent (CDI, DECP, DCC, a combination of DCC and HOBt, or the like) to synthesize the compound of the formula (29).

Reaction formula (10):

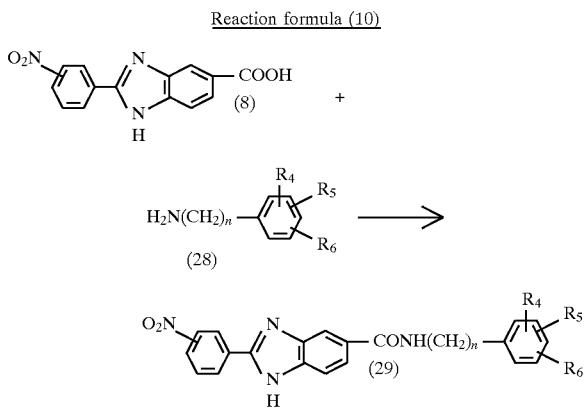

As a solvent for this reaction, DMF is desirable, but another conventional solvent can also be used. The state of this reaction can be observed by TLC or the like to confirm the completion of the reaction, but the reaction is preferably carried out for a period of from 1 to 40 hours. A reaction temperature is preferably in the range of from −5° to 40° C.

Moreover, as shown in the following reaction formula (11), the nitro group of the compound of the formula (29) can be reduced to a corresponding amino group by catalytic hydrogenation using Pd/C as a catalyst.

Reaction formula (11):

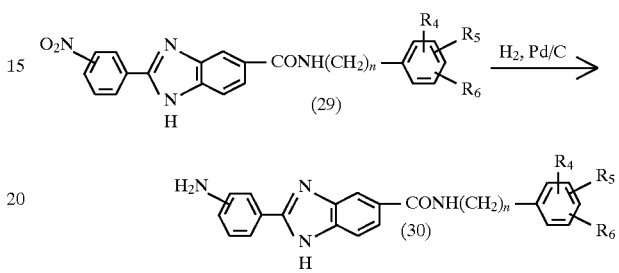

This reaction proceeds substantially quantitatively. In this case, ethanol, methanol and DMF can be used singly or in a combination of two or more thereof as a solvent. At this time, hydrochloric acid can be added in an amount equal to or more than mols of the nitro compound, usually in an amount of from 1 to 1.2 mols. The reaction is preferably carried out at a temperature of from 0° to 40° C. for a period of from 10 minutes to 20 hours.

The bonding of the aniline derivative in the reaction formula (10) and the successive reducing reaction in the reaction formula (11) establish a novel synthetic route which has not been found in literature so far. For example, a bonding reaction of a distamycin derivative and N,N-bis(2-chloroethyl)-1,4-phenylenediamine is disclosed in Japanese Patent Laid-open No. 92933/1994, but in this publication, a distamycin moiety is previously synthesized, and the bonding reaction of N,N-bis(2-chloroethyl)-1,4-phenylenediamine is finally carried out. This is based on a conception that the bonding of an N,N-bis(2-chloroethyl) amino group which is highly chemically reactive is performed in the last step. On the contrary, the present inventors have developed the technique that even if the aniline derivative moiety is previously introduced into the molecule, the desired compound can be obtained in a high yield.

Next, as shown in the following reaction formula (12), the amino compound of the formula (30) obtained by the previous reducing reaction is bonded to the carboxylic acid derivative of the formula (12) in the presence of a conventional condensing agent such as DCC, CDI, EDCI or DECP to introduce a $R_1$ moiety to the amino compound, thereby obtaining a compound in the group B [$R_2$ is a group shown in the formula (2)].

Reaction formula (12):

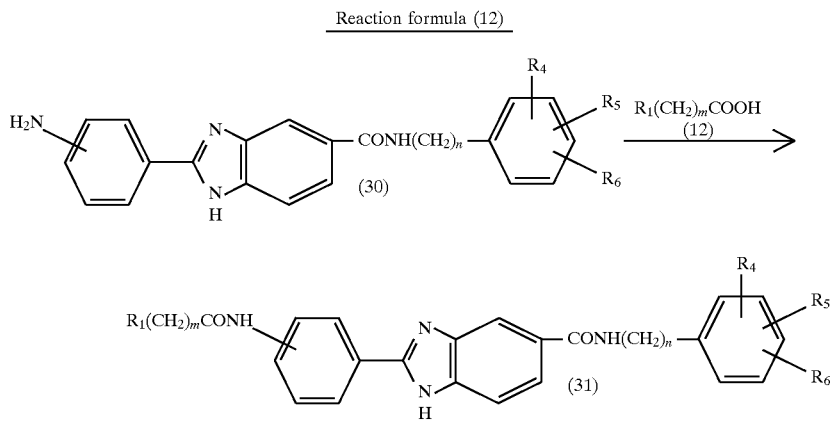

As a solvent for this reaction, a usual solvent is usable, but DMF or a mixed solvent containing DMF leads to good results. The reaction is preferably carried out at a temperature of from 0° to 40° C. for a period of from 30 minutes to 40 hours.

The employment of the following process permits the synthesis of a compound in the group B in which $R_1$ is a hydrogen atom, a halogen atom or a group other than the groups represented by the formula (2).

For example, as shown in the following reaction formula (13), a compound represented by the formula (32) can be methylated in accordance with a technique described in J. Org. Chem., Vol. 25, p. 804–807 (1960) or with the aid of a usual methylating agent (e.g., methyl iodide, dimethylsulfuric acid or methyl p-toluenesulfonate) to obtain a sulfonium derivative represented by the formula (33).

Reaction formula (13):

A counter anion ($I^-$) of the sulfonium compound obtained here can be converted into another anion in a known manner. For example, $I^-$ can be converted into $Cl^-$ by the use of a $Cl^-$ type ion exchange resin (Dowex 1×8).

In the above-mentioned reaction formula (12), when a compound in which $R_1$ is a substituted or an unsubstituted amino group is used as the compound of the formula (12), a compound in the group B can be obtained in which $R_1$ is the substituted or the unsubstituted amino group.

The thus obtained compound in which $R_1$ is the amino group substituted by two alkyl groups is further alkylated in a known manner, whereby this compound can be converted into a compound in which $R_1$ is an ammonium group.

Furthermore, as shown in the following reaction formula (14), a compound represented by the formula (34) is methylated with methyl iodide to obtain a compound represented by the formula (35).

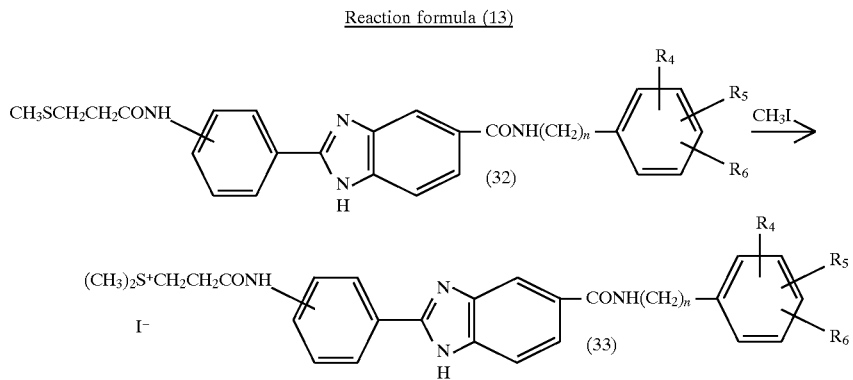

As a solvent for this reaction, formic acid, acetic acid, acetone or the like can be used. Alternatively, the reaction can be done under non-solvent. The reaction is preferably carried out at a temperature of from 0° to 60° C. for a period of from 1 to 60 hours.

Reaction formula (14):

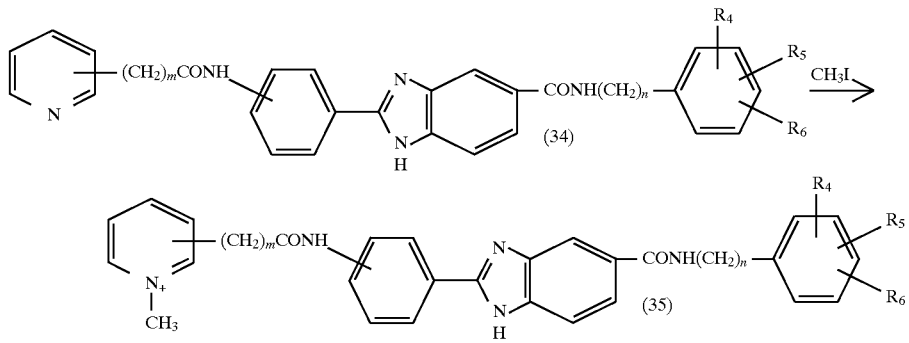

At this time, a usual solvent such as methanol, acetone, chloroform or methylene chloride is used. The reaction is preferably carried out at a temperature of from −5° to 50° C. for a period of from 1 to 50 hours.

Moreover, as shown in the following reaction formula (15), when the amino compound of the formula (30) is reacted with guanidoacetic acid, a compound of the formula (36) can be synthesized in which a guanidino group is introduced into $R_1$.

Reaction formula (15):

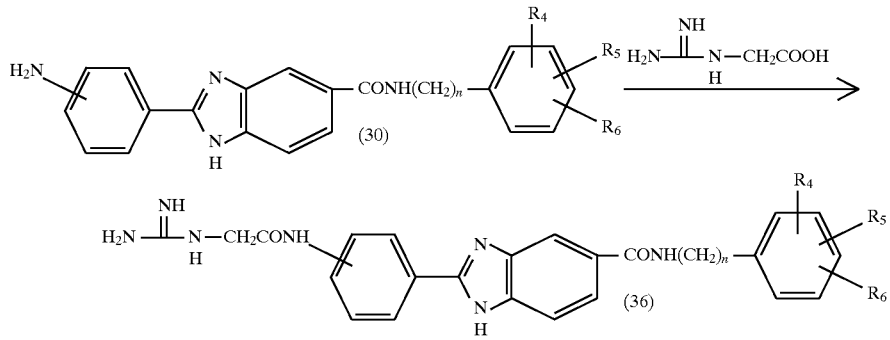

A compound in which $R_1$ is an amidino group can be synthesized as follows. First, the amino compound of the formula (30) is bonded to a carboxylic acid derivative having a cyano group such as 3-cyanopropionic acid in the presence of a conventional condensing agent such as DCC, CDI, EDCI or DECP. As a solvent for this reaction, a conventional solvent is usable, but DMF or a mixed solvent containing DMF leads to good results. The reaction is preferably carried out at a temperature of from 0° to 40° C. for a period of from 1 to 24 hours. The resultant product is dissolved or suspended in a solvent, and a hydrochloric acid gas is then blown thereinto, thereby obtaining an imidated compound. This compound is then dissolved or suspended in the solvent, and an ammonium gas is then blown thereinto, thereby synthesizing the desired compound in which the amidino group is introduced into $R_1$. As the solvent, ethanol, methanol or a mixed solvent thereof is used. In this case, the reaction is preferably carried out at a temperature of from 0° to 40° C. for a period of from 30 minutes to 24 hours.

Another compound can be synthesized by changing starting materials under the above-mentioned conditions.

The compounds in the groups A and B can be synthesized as described above, but the synthesis of a compound in which both of $R_1$ and $R_2$ are groups represented by the formula (2) can be accomplished, for example, as follows.

In the first place, as shown in the following reaction formula (16), a compound (a nitro compound) represented by the formula (37) can be reduced to a corresponding amino group of the formula (38) by catalytic hydrogenation using Pd/C as a catalyst. In this case, ethanol, methanol and DMF can be used singly or in a combination of two or more thereof as a solvent.

Reaction formula (16):

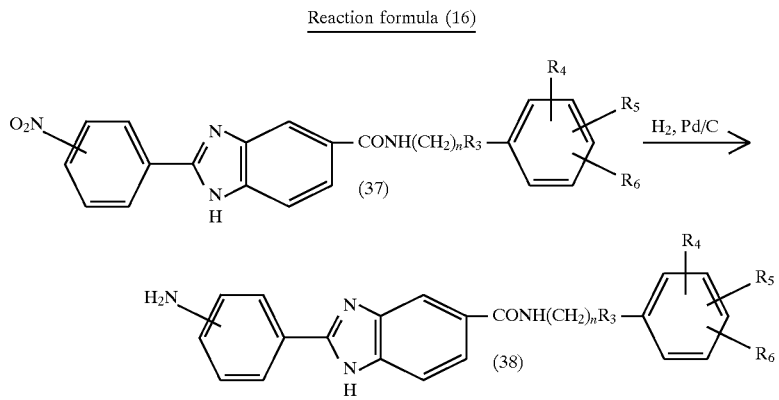

At this time, hydrochloric acid can be added in an amount equal to or more than mols of the nitro compound, usually in an amount of from 1 to 1.2 mols. The reaction is preferably carried out for a period of from 10 minutes to 20 hours.

Next, as shown in the following reaction formula (17), the amino compound of the formula (38) can be reacted with a carboxylic acid derivative of the formula (39) to obtain a compound represented by the formula (40).

Reaction formula (17):

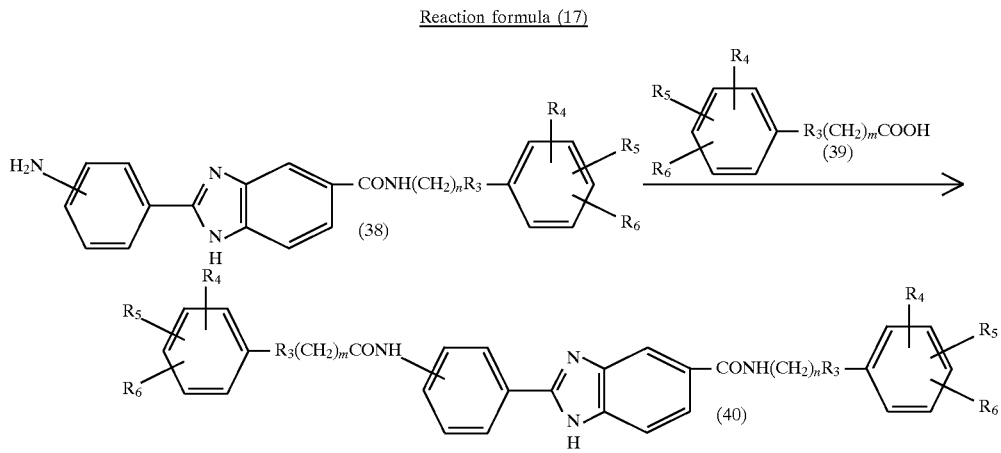

At this time, a conventional condensing agent (e.g., DCC, CDI, EDCI or DECP) can be used. As a solvent for the above-mentioned reaction, a conventional solvent is usable, but DMF or a mixed solvent containing DMF leads to good results. The reaction is preferably carried out at a temperature of from 0° to 40° C. for a period of from 30 minutes to 40 hours.

Examples of the compound of the formula (1) according to the present invention will be enumerated in Table 1 given below. In Table 1, neither an ammonium group nor a counter anion of a sulfonium group is shown, but any counter anion is usable, so far as it is pharmacologically acceptable. When the counter anion is required to be specified, its typical example will be mentioned.

The compounds of the present invention can be used as anticancer agents having excellent activity. Examples of carcinomas to which the compounds of the present invention can be applied include leukemia, osteosarcoma, breast cancer, ovarian cancer, stomach cancer, colon cancer, lung cancer, and head and neck cancer. In addition, the compounds of the present invention can also be utilized as antimicrobial agents and antiviral agents.

Pharmaceutical compositions can be prepared in accordance with well-known techniques.

Various dosage forms can be selected in compliance with the purpose of a medical treatment, and typical examples of the dosage forms include solid preparations, liquid preparations and other preparations such as suppositories. These dosage forms will be described in more detail.

Examples of the solid preparations include tablets, pills, powders, granules and capsules; examples of the liquid preparations include injectable solutions, suspensions, syrups and emulsions; and examples of the other preparations include suppositories.

In preparing the pharmaceutical compositions in the form of the tablets, there can be used a wide variety of carriers which have been heretofore well known in this field. Examples of the carriers include excipients such as lactose, sucrose, sodium chloride, glucose, starch, calcium carbonate, kaolin, crystalline cellulose and silicic acid; binders such as water, ethanol, propanol, simple syrup, glucose solution, starch solution, gelatin solution, shellac solution, methyl cellulose solution, hydroxypropyl cellulose solution, polyvinyl pyrrolidone solution and carboxymethyl cellulose solution; disintegrators such as dry starch, sodium alginate, agar powder, sodium hydrogencarbonate, calcium carbonate, polyoxyethylene sorbitan fatty acid esters, sodium lauryl sulfate, stearic acid monoglyceride, starch and lactose; disintegration inhibitors such as sucrose, stearic acid, cacao butter and hydrogenated oil; absorption promoters such as quaternary ammonium bases and sodium lauryl sulfate; humectants such as glycerin and starch; adsorbents such as starch, lactose, kaolin, bentonite, colloidal silicic acid, crystalline cellulose and light anhydrous silicic acid; and lubricants such as talc, stearates, boric acid powder and polyethylene glycol.

If necessary, the tablets can also take the usual forms of coated tablets such as sugar-coated tablets, gelatin-coated tablets, enteric coated tablets, film-coated tablets, bilayer tablets or multilayer tablets.

In preparing the pharmaceutical compositions in the form of the pills, there can be used a wide variety of carriers which have been heretofore well known in this field. Examples of the carriers include excipients such as glucose, lactose, starch, cacao butter, hardened vegetable oil, kaolin and talc; binders such as powdered acacia, powdered tragacanth and gelatin; and disintegrators such as carboxymethylcellulose calcium and agar.

The capsules can be prepared in accordance with a conventional procedure, i.e., by mixing a compound as an active ingredient with any of the previously enumerated carriers, and then filling the resulting mixture into hard gelatin capsules, soft capsules or the like.

In preparing the pharmaceutical compositions in the form of the injections, solutions, emulsions or sus- pensions are prepared by the use of diluents. Examples of the diluents which can often be used in this field include water, ethanol, macrogol, propylene glycol, ethoxylated isostearyl alcohol, polyoxylated isostearyl alcohol, polyoxyethylene sorbitan fatty acid esters, cotton seed oil, corn oil, peanut oil and olive oil. Moreover, the compounds of the present invention can also be used in the form of aqueous suspensions prepared by adding water thereto in the presence of a suitable surfactant, or in the form of emulsions prepared with the aid of a surfactant such as polyoxyethylene hardened castor oil (HCO-60). Furthermore, sodium chloride, glucose and/or glycerol may be contained in the pharmaceutical compositions, and a conventional solubilizer, buffering agent and/or soothing agent may be added thereto.

In preparing the pharmaceutical compositions in the form of suppositories, there can be used a wide variety of carriers which have been heretofore well known in this field. Examples of the carriers include polyethylene glycol, cacao butter, higher alcohols, esters of higher alcohols, gelatin and semisynthetic glycerides.

If necessary, the pharmaceutical compositions can contain colorants, preservatives, perfumes, flavors, sweeteners and/or other drugs.

No particular restriction is put on an administration manner of the pharmaceutical compositions of the present invention, and they may be administered in accordance with the form of the pharmaceutical composition, the age, sex and other conditions of a patient and the severity of a disease. For example, the tablets, pills, solutions, suspensions, emulsions, powders, granules, syrups and capsules can be orally administered. The injections can be intravenously administered alone or after mixed with a usual infusion fluid such as glucose or an amino acid. Alternatively, they may also be administered intramuscularly, subcutaneously or intraperitoneally as required. The suppositories can be administered intrarectally. The dose of the pharmaceutical compositions of the present invention can be suitably determined in compliance with the administration manner, the age, sex and other conditions of a patient, and the severity of a disease. However, the dose should conventionally be determined so that the amount of the compound as the active ingredient may be in the range of from about 0.001 to 1,000 mg per day for an adult. Moreover, it is desirable that each unit dosage form of the pharmaceutical composition to be administered contains the compound as the active ingredient in an amount in the range of about 0.001 to 1,000 mg.

Generally speaking, anticancer agents, for example, even agents such as adriamycin and cisplatin which have often been used, have no small side effect. At a present technical level, the side effect should be judged in consideration of relations with functional strength, and the problem of the side effect is unavoidable to some extent. The side effect of the compounds according to the present invention is at such a level as to be acceptable as the anticancer agents.

TABLE 1

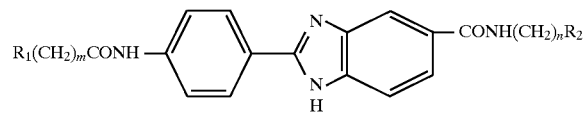

$R_1(CH_2)_m CONH$—⟨benzene⟩—⟨benzimidazole(N,NH)⟩—$CONH(CH_2)_n R_2$

| Compound No. | $R_1$ | m | $R_2$ | n |
|---|---|---|---|---|
| 1 | $(ClCH_2CH_2)_2N$—⟨phenyl⟩— | 0 | —NH—C(=NH)—$NH_2$ | 2 |
| 2 | $(ClCH_2CH_2)_2N$—⟨phenyl⟩— | 3 | —NH—C(=NH)—$NH_2$ | 2 |
| 3 | $(ClCH_2CH_2)_2N$—⟨phenyl, $H_3C$-substituted⟩— | 0 | —NH—C(=NH)—$NH_2$ | 2 |

TABLE 1-continued
| | | | | |
|---|---|---|---|---|
| 4 | 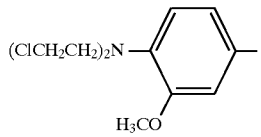 | 0 | 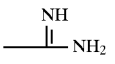 | 2 |
| 5 | 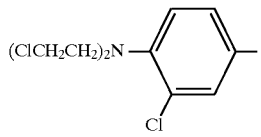 | 0 | 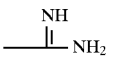 | 2 |
| 6 | 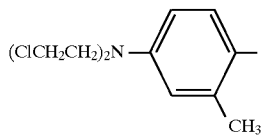 | 0 | 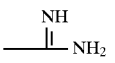 | 2 |
| 7 | 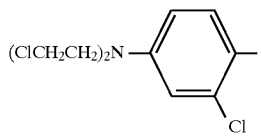 | 0 | 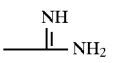 | 2 |
| 8 | 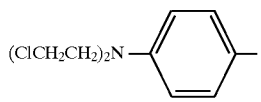 | 1 | 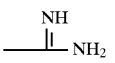 | 2 |
| 9 | 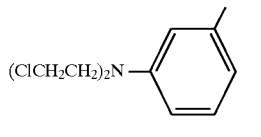 | 0 | 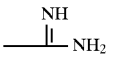 | 2 |
| 10 | 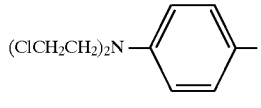 | 0 | 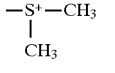 | 2 |
| 11 | 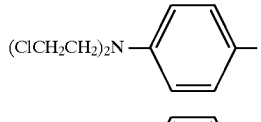 | 3 | 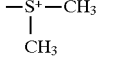 | 2 |
| 12 | 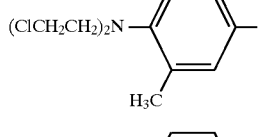 | 0 |  | 2 |
| 13 | 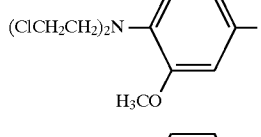 | 0 | 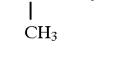 | 2 |
| 14 | 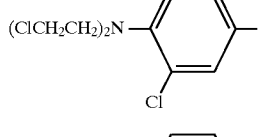 | 0 | 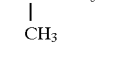 | 2 |
| 15 | 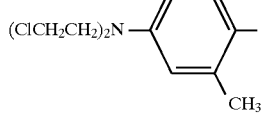 | 0 | 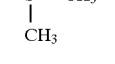 | 2 |

TABLE 1-continued
| 16 | 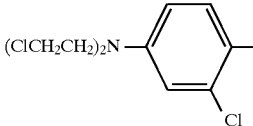 | 0 | −S⁺(CH₃)CH₃ | 2 |
| --- | --- | --- | --- | --- |
| 17 | 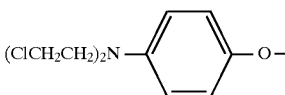 | 1 | −S⁺(CH₃)CH₃ | 2 |
| 18 | 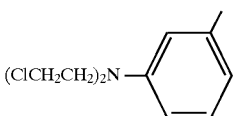 | 0 | −S⁺(CH₃)CH₃ | 2 |
| 19 | 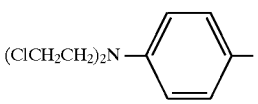 | 0 | −NH−C(=NH)−NH₂ | 1 |
| 20 | 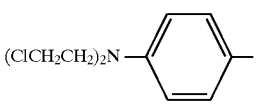 | 3 | −NH−C(=NH)−NH₂ | 1 |
| 21 | 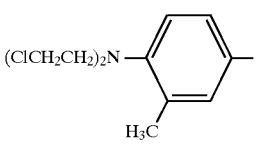 | 0 | −NH−C(=NH)−NH₂ | 1 |
| 22 | 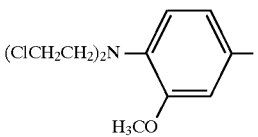 | 0 | −NH−C(=NH)−NH₂ | 1 |
| 23 | 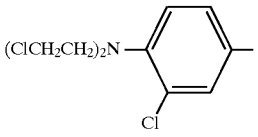 | 0 | −NH−C(=NH)−NH₂ | 1 |
| 24 | 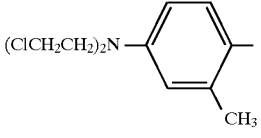 | 0 | −NH−C(=NH)−NH₂ | 1 |
| 25 | 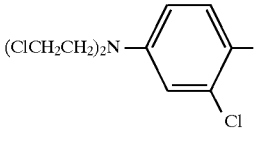 | 0 | −NH−C(=NH)−NH₂ | 1 |
| 26 | 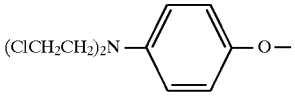 | 1 | −NH−C(=NH)−NH₂ | 1 |
| 27 | 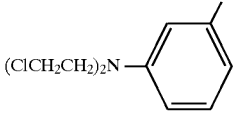 | 0 | −NH−C(=NH)−NH₂ | 1 |

TABLE 1-continued
| # | Structure | | Group | n |
|---|---|---|---|---|
| 28 | 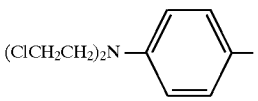 | 0 | —N(CH₃)CH₃ | 3 |
| 29 | 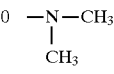 | 3 | —N(CH₃)CH₃ | 3 |
| 30 | 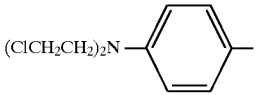 | 0 | —N(CH₃)CH₃ | 3 |
| 31 | 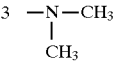 | 0 | —N(CH₃)CH₃ | 3 |
| 32 | 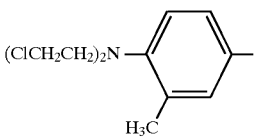 | 0 | —N(CH₃)CH₃ | 3 |
| 33 | 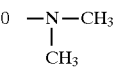 | 0 | —N(CH₃)CH₃ | 3 |
| 34 | 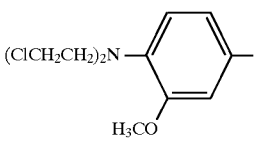 | 0 | —N(CH₃)CH₃ | 3 |
| 35 | 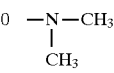 | 1 | —N(CH₃)CH₃ | 3 |
| 36 | 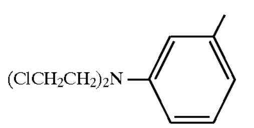 | 0 | —N(CH₃)CH₃ | 3 |
| 37 | 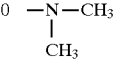 | 0 | —Cl | 2 |
| 38 | 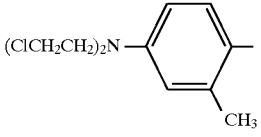 | 0 | —Br | 2 |
| 39 | 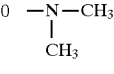 | 0 | —S—CH₃ | 2 |
| 40 | 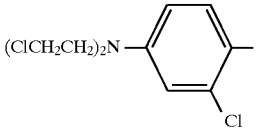 | 0 | —N⁺(CH₃)₃ | 3 |

TABLE 1-continued
| | | | | |
|---|---|---|---|---|
| 41 | (ClCH₂CH₂)₂N—⌬— | 0 | imidazoline | 3 |
| 42 | (ClCH₂CH₂)₂N—⌬— | 0 | furan | 0 |
| 43 | (ClCH₂CH₂)₂N—⌬— | 0 | —C₆H₄—NH—C(=NH)NH₂ | 0 |
| 44 | H | 0 | —N(CH₃)₂ | 3 |
| 45 | H | 0 | —C(=NH)NH₂ | 2 |
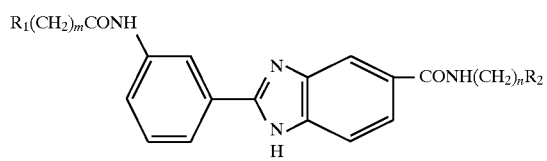
| Compound No. | R₁ | m | R₂ | n |
|---|---|---|---|---|
| 46 | (ClCH₂CH₂)₂N—⌬— | 0 | —C(=NH)NH₂ | 2 |
| 47 | (ClCH₂CH₂)₂N—⌬— | 3 | —C(=NH)NH₂ | 2 |
| 48 | (ClCH₂CH₂)₂N—⌬(3-CH₃)— | 0 | —C(=NH)NH₂ | 2 |
| 49 | (ClCH₂CH₂)₂N—⌬(3-OCH₃)— | 0 | —C(=NH)NH₂ | 2 |
| 50 | (ClCH₂CH₂)₂N—⌬(3-Cl)— | 0 | —C(=NH)NH₂ | 2 |
| 51 | (ClCH₂CH₂)₂N—⌬(3-CH₃)— | 0 | —C(=NH)NH₂ | 2 |

TABLE 1-continued
| 52 | 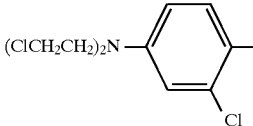 | 0 |  | 2 |
| 53 | 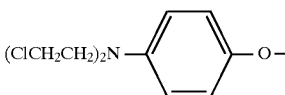 | 1 |  | 2 |
| 54 | 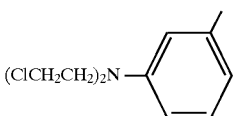 | 0 |  | 2 |
| 55 | 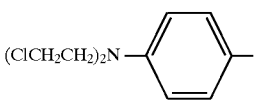 | 0 | —S⁺—CH₃<br>    \|<br>    CH₃ | 2 |
| 56 |  | 3 | —S⁺—CH₃<br>    \|<br>    CH₃ | 2 |
| 57 | 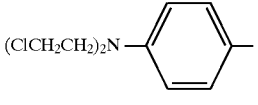 | 0 | —S⁺—CH₃<br>    \|<br>    CH₃ | 2 |
| 58 |  | 0 | —S⁺—CH₃<br>    \|<br>    CH₃ | 2 |
| 59 | 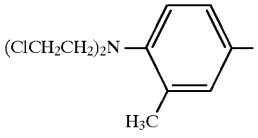 | 0 | —S⁺—CH₃<br>    \|<br>    CH₃ | 2 |
| 60 |  | 0 | —S⁺—CH₃<br>    \|<br>    CH₃ | 2 |
| 61 | 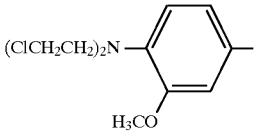 | 0 | —S⁺—CH₃<br>    \|<br>    CH₃ | 2 |
| 62 |  | 1 | —S⁺—CH₃<br>    \|<br>    CH₃ | 2 |
| 63 | 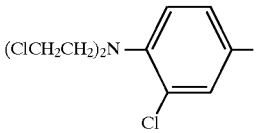 | 0 | —S⁺—CH₃<br>    \|<br>    CH₃ | 2 |

TABLE 1-continued

| | | | | |
|---|---|---|---|---|
| 64 | (ClCH₂CH₂)₂N—⟨phenyl⟩— | 0 | —NH—C(=NH)—NH₂ | 1 |
| 65 | (ClCH₂CH₂)₂N—⟨phenyl⟩— | 3 | —NH—C(=NH)—NH₂ | 1 |
| 66 | (ClCH₂CH₂)₂N—⟨phenyl, H₃C⟩— | 0 | —NH—C(=NH)—NH₂ | 1 |
| 67 | (ClCH₂CH₂)₂N—⟨phenyl, H₃CO⟩— | 0 | —NH—C(=NH)—NH₂ | 1 |
| 68 | (ClCH₂CH₂)₂N—⟨phenyl, Cl⟩— | 0 | —NH—C(=NH)—NH₂ | 1 |
| 69 | (ClCH₂CH₂)₂N—⟨phenyl, CH₃⟩— | 0 | —NH—C(=NH)—NH₂ | 1 |
| 70 | (ClCH₂CH₂)₂N—⟨phenyl, Cl⟩— | 0 | —NH—C(=NH)—NH₂ | 1 |
| 71 | (ClCH₂CH₂)₂N—⟨phenyl⟩—O— | 1 | —NH—C(=NH)—NH₂ | 1 |
| 72 | (ClCH₂CH₂)₂N—⟨phenyl⟩— | 0 | —NH—C(=NH)—NH₂ | 1 |
| 73 | (ClCH₂CH₂)₂N—⟨phenyl⟩— | 0 | —N(CH₃)—CH₃ | 3 |
| 74 | (ClCH₂CH₂)₂N—⟨phenyl⟩— | 3 | —N(CH₃)—CH₃ | 3 |
| 75 | (ClCH₂CH₂)₂N—⟨phenyl, H₃C⟩— | 0 | —N(CH₃)—CH₃ | 3 |

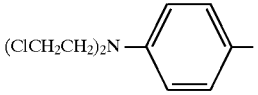
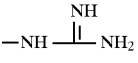
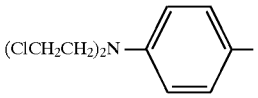
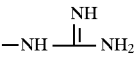
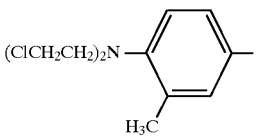
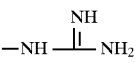
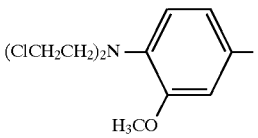
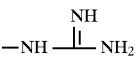
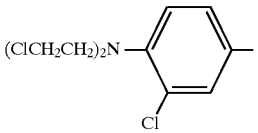
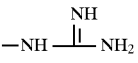
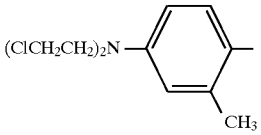
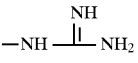
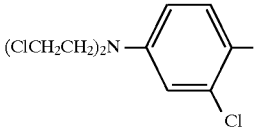
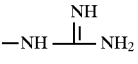
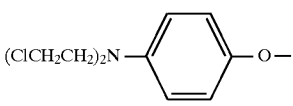
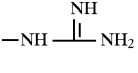
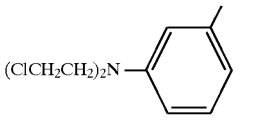
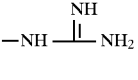
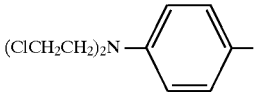
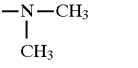
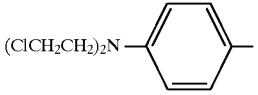
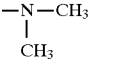
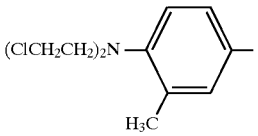
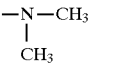

TABLE 1-continued

| # | Ar | n | R | m |
|---|---|---|---|---|
| 76 | (ClCH₂CH₂)₂N—[phenyl, H₃CO substituent]— | 0 | —N(CH₃)CH₃ | 3 |
| 77 | (ClCH₂CH₂)₂N—[phenyl, Cl substituent]— | 0 | —N(CH₃)CH₃ | 3 |
| 78 | (ClCH₂CH₂)₂N—[phenyl, CH₃ substituent]— | 0 | —N(CH₃)CH₃ | 3 |
| 79 | (ClCH₂CH₂)₂N—[phenyl, Cl substituent]— | 0 | —N(CH₃)CH₃ | 3 |
| 80 | (ClCH₂CH₂)₂N—[phenyl]—O— | 1 | —N(CH₃)CH₃ | 3 |
| 81 | (ClCH₂CH₂)₂N—[phenyl, CH₃ substituent]— | 0 | —N(CH₃)CH₃ | 3 |
| 82 | (ClCH₂CH₂)₂N—[phenyl]— | 0 | —Cl | 2 |
| 83 | (ClCH₂CH₂)₂N—[phenyl]— | 0 | —Br | 2 |
| 84 | (ClCH₂CH₂)₂N—[phenyl]— | 0 | —S—CH₃ | 2 |
| 85 | (ClCH₂CH₂)₂N—[phenyl]— | 0 | —N⁺(CH₃)₃ | 3 |
| 86 | (ClCH₂CH₂)₂N—[phenyl]— | 0 | [4,5-dihydroimidazol-2-yl] | 3 |
| 87 | (ClCH₂CH₂)₂N—[phenyl]— | 0 | [furan-2-yl] | 0 |
| 88 | (ClCH₂CH₂)₂N—[phenyl]— | 0 | —[phenyl]—NH—C(=NH)NH₂ | 0 |

TABLE 1-continued

| | | | | |
|---|---|---|---|---|
| 89 | H | 0 | —N(CH$_3$)—CH$_3$ | 3 |
| 90 | H | 0 | —C(=NH)NH$_2$ | 2 |

R$_1$(CH$_2$)$_m$CONH—[phenyl]—[benzimidazole]—CONH(CH$_2$)$_n$R$_2$

| Compound No. | R$_1$ | m | R$_2$ | n |
|---|---|---|---|---|
| 91 | (ClCH$_2$CH$_2$)$_2$N—[p-phenyl]— | 0 | —[p-phenyl]—N(CH$_2$CH$_2$Cl)$_2$ | 0 |
| 92 | (ClCH$_2$CH$_2$)$_2$N—[p-phenyl]— | 0 | —[m-phenyl]—N(CH$_2$CH$_2$Cl)$_2$ | 0 |
| 93 | (ClCH$_2$CH$_2$)$_2$N—[m-phenyl]— | 0 | —[p-phenyl]—N(CH$_2$CH$_2$Cl)$_2$ | 0 |
| 94 | (ClCH$_2$CH$_2$)$_2$N—[m-phenyl]— | 0 | —[m-phenyl]—N(CH$_2$CH$_2$Cl)$_2$ | 0 |
| 95 | ClCH$_2$CH$_2$N(CH$_2$CH$_3$)—[p-phenyl]— | 0 | —[p-phenyl]—N(CH$_2$CH$_2$Cl)(CH$_2$CH$_3$) | 0 |
| 96 | ClCH$_2$CH$_2$N(CH$_2$CH$_3$)—[p-phenyl]— | 0 | —[m-phenyl]—N(CH$_2$CH$_2$Cl)(CH$_2$CH$_3$) | 0 |
| 97 | ClCH$_2$CH$_2$N(CH$_2$CH$_3$)—[m-phenyl]— | 0 | —[p-phenyl]—N(CH$_2$CH$_2$Cl)(CH$_2$CH$_3$) | 0 |
| 98 | ClCH$_2$CH$_2$N(CH$_2$CH$_3$)—[m-phenyl]— | 0 | —[m-phenyl]—N(CH$_2$CH$_2$Cl)(CH$_2$CH$_3$) | 0 |

R$_1$(CH$_2$)$_m$CONH—[phenyl]—[benzimidazole]—CONH(CH$_2$)$_n$R$_2$

| Compound No. | R$_1$ | m | R$_2$ | n |
|---|---|---|---|---|
| 99 | (ClCH$_2$CH$_2$)$_2$N—[p-phenyl]— | 0 | —[p-phenyl]—N(CH$_2$CH$_2$Cl)$_2$ | 0 |

TABLE 1-continued

| Compound No. | (structure 1) | | (structure 2) | |
|---|---|---|---|---|
| 100 | (ClCH₂CH₂)₂N—⟨phenyl, para⟩— | 0 | —⟨phenyl, meta⟩—N(CH₂CH₂Cl)₂ | 0 |
| 101 | (ClCH₂CH₂)₂N—⟨phenyl, meta⟩— | 0 | —⟨phenyl, para⟩—N(CH₂CH₂Cl)₂ | 0 |
| 102 | (ClCH₂CH₂)₂N—⟨phenyl, meta⟩— | 0 | —⟨phenyl, meta⟩—N(CH₂CH₂Cl)₂ | 0 |
| 103 | ClCH₂CH₂N(CH₂CH₃)—⟨phenyl, para⟩— | 0 | —⟨phenyl, para⟩—N(CH₂CH₂Cl)(CH₂CH₃) | 0 |
| 104 | ClCH₂CH₂N(CH₂CH₃)—⟨phenyl, para⟩— | 0 | —⟨phenyl, meta⟩—N(CH₂CH₂Cl)(CH₂CH₃) | 0 |
| 105 | ClCH₂CH₂N(CH₂CH₃)—⟨phenyl, meta⟩— | 0 | —⟨phenyl, para⟩—N(CH₂CH₂Cl)(CH₂CH₃) | 0 |
| 106 | ClCH₂CH₂N(CH₂CH₃)—⟨phenyl, meta⟩— | 0 | —⟨phenyl, meta⟩—N(CH₂CH₂Cl)(CH₂CH₃) | 0 |

$R_1(CH_2)_m CONH$—⟨phenyl⟩—⟨benzimidazole (NH)⟩—$CONH(CH_2)_n R_2$

| Compound No. | $R_1$ | m | $R_2$ | n |
|---|---|---|---|---|
| 1001 | H₂N—C(=NH)—NH— | 1 | —⟨phenyl, para⟩—N(CH₂CH₂Cl)₂ | 0 |
| 1002 | H₂N—C(=NH)—NH— | 1 | —⟨phenyl, para⟩—N(CH₂CH₂Cl)₂ | 2 |
| 1003 | H₂N—C(=NH)—NH— | 1 | —⟨phenyl, para⟩—N(CH₂CH₂Cl)₂ | 3 |
| 1004 | H₂N—C(=NH)—NH— | 1 | —⟨phenyl, para-N(CH₂CH₂Cl)₂, meta-CH₃⟩ | 0 |

TABLE 1-continued

| No. | R | n | Ar | m |
|---|---|---|---|---|
| 1005 | H₂N-C(=NH)-NH- | 1 | 4-[N(CH₂CH₂Cl)₂]-3-OCH₃-phenyl | 0 |
| 1006 | H₂N-C(=NH)-NH- | 1 | 4-[N(CH₂CH₂Cl)₂]-3-Cl-phenyl | 0 |
| 1007 | H₂N-C(=NH)-NH- | 1 | 3-[N(CH₂CH₂Cl)₂]-4-CH₃-phenyl | 0 |
| 1008 | H₂N-C(=NH)-NH- | 1 | 3-[N(CH₂CH₂Cl)₂]-4-Cl-phenyl | 0 |
| 1009 | H₂N-C(=NH)-NH- | 1 | -O-C₆H₄-N(CH₂CH₂Cl)₂ (para) | 1 |
| 1010 | H₂N-C(=NH)-NH- | 1 | 3-[N(CH₂CH₂Cl)₂]-phenyl | 0 |
| 1011 | H₂N-C(=NH)-NH- | 3 | 4-[N(CH₂CH₂Cl)₂]-phenyl | 0 |
| 1012 | H₂N-C(=NH)-NH- | 3 | 4-[N(CH₂CH₂Cl)₂]-phenyl | 2 |
| 1013 | H₂N-C(=NH)-NH- | 3 | 4-[N(CH₂CH₂Cl)₂]-phenyl | 3 |
| 1014 | H₂N-C(=NH)-NH- | 3 | 4-[N(CH₂CH₂Cl)₂]-3-CH₃-phenyl | 0 |
| 1015 | H₂N-C(=NH)-NH- | 3 | 4-[N(CH₂CH₂Cl)₂]-3-OCH₃-phenyl | 0 |
| 1016 | H₂N-C(=NH)-NH- | 3 | 4-[N(CH₂CH₂Cl)₂]-3-Cl-phenyl | 0 |

TABLE 1-continued

| No. | Group 1 | n | Group 2 | m |
|---|---|---|---|---|
| 1017 | H$_2$N-C(=NH)-NH- | 3 | 4-N(CH$_2$CH$_2$Cl)$_2$-3-CH$_3$-phenyl | 0 |
| 1018 | H$_2$N-C(=NH)-NH- | 3 | 4-N(CH$_2$CH$_2$Cl)$_2$-2-Cl-phenyl | 0 |
| 1019 | H$_2$N-C(=NH)-NH- | 3 | -O-(4-N(CH$_2$CH$_2$Cl)$_2$-phenyl) | 1 |
| 1020 | H$_2$N-C(=NH)-NH- | 3 | 3-N(CH$_2$CH$_2$Cl)$_2$-phenyl | 0 |
| 1021 | H$_2$N-C(=NH)- | 3 | 4-N(CH$_2$CH$_2$Cl)$_2$-phenyl | 0 |
| 1022 | H$_2$N-C(=NH)- | 3 | 4-N(CH$_2$CH$_2$Cl)$_2$-phenyl | 2 |
| 1023 | H$_2$N-C(=NH)- | 3 | 4-N(CH$_2$CH$_2$Cl)$_2$-phenyl | 3 |
| 1024 | H$_2$N-C(=NH)- | 3 | 4-N(CH$_2$CH$_2$Cl)$_2$-3-CH$_3$-phenyl | 0 |
| 1025 | H$_2$N-C(=NH)- | 3 | 4-N(CH$_2$CH$_2$Cl)$_2$-3-OCH$_3$-phenyl | 0 |
| 1026 | H$_2$N-C(=NH)- | 3 | 4-N(CH$_2$CH$_2$Cl)$_2$-3-Cl-phenyl | 0 |
| 1027 | H$_2$N-C(=NH)- | 3 | 4-N(CH$_2$CH$_2$Cl)$_2$-2-CH$_3$-phenyl | 0 |
| 1028 | H$_2$N-C(=NH)- | 3 | 4-N(CH$_2$CH$_2$Cl)$_2$-2-Cl-phenyl | 0 |

TABLE 1-continued

| No. | Group 1 | n | Group 2 | Val |
|---|---|---|---|---|
| 1029 | H₂N−C(=NH)− | 3 | −O−C₆H₄−N(CH₂CH₂Cl)₂ (para) | 1 |
| 1030 | H₂N−C(=NH)− | 3 | 3-CH₃-C₆H₄-N(CH₂CH₂Cl)₂ | 0 |
| 1031 | (CH₃)₂N− | 3 | 4-CH₃-C₆H₄-N(CH₂CH₂Cl)₂ | 0 |
| 1032 | (CH₃)₂N− | 3 | 4-CH₃-C₆H₄-N(CH₂CH₂Cl)₂ | 2 |
| 1033 | (CH₃)₂N− | 3 | 4-CH₃-C₆H₄-N(CH₂CH₂Cl)₂ | 3 |
| 1034 | (CH₃)₂N− | 3 | 4-CH₃-2-CH₃-C₆H₃-N(CH₂CH₂Cl)₂ | 0 |
| 1035 | (CH₃)₂N− | 3 | 4-CH₃-2-OCH₃-C₆H₃-N(CH₂CH₂Cl)₂ | 0 |
| 1036 | (CH₃)₂N− | 3 | 4-CH₃-2-Cl-C₆H₃-N(CH₂CH₂Cl)₂ | 0 |
| 1037 | (CH₃)₂N− | 3 | 4-CH₃-3-CH₃-C₆H₃-N(CH₂CH₂Cl)₂ | 0 |
| 1038 | (CH₃)₂N− | 3 | 4-Cl-C₆H₃-N(CH₂CH₂Cl)₂ | 0 |
| 1039 | (CH₃)₂N− | 3 | −O−C₆H₄−N(CH₂CH₂Cl)₂ (para) | 1 |
| 1040 | (CH₃)₂N− | 3 | 3-CH₃-C₆H₄-N(CH₂CH₂Cl)₂ | 0 |
| 1041 | (CH₃)₂S⁺− | 2 | 4-C₆H₄-N(CH₂CH₂Cl)₂ | 0 |

TABLE 1-continued

| No. | Group 1 | n | Group 2 | Val |
|---|---|---|---|---|
| 1042 | H₃C—S⁺(CH₃)— | 2 | —C₆H₄—N(CH₂CH₂Cl)₂ | 2 |
| 1043 | H₃C—S⁺(CH₃)— | 2 | —C₆H₄—N(CH₂CH₂Cl)₂ | 3 |
| 1044 | H₃C—S⁺(CH₃)— | 2 | —C₆H₃(CH₃)—N(CH₂CH₂Cl)₂ | 0 |
| 1045 | H₃C—S⁺(CH₃)— | 2 | —C₆H₃(OCH₃)—N(CH₂CH₂Cl)₂ | 0 |
| 1046 | H₃C—S⁺(CH₃)— | 2 | —C₆H₃(Cl)—N(CH₂CH₂Cl)₂ | 0 |
| 1047 | H₃C—S⁺(CH₃)— | 2 | —C₆H₃(CH₃)—N(CH₂CH₂Cl)₂ | 0 |
| 1048 | H₃C—S⁺(CH₃)— | 2 | —C₆H₃(Cl)—N(CH₂CH₂Cl)₂ | 0 |
| 1049 | H₃C—S⁺(CH₃)— | 2 | —O—C₆H₄—N(CH₂CH₂Cl)₂ | 1 |
| 1050 | H₃C—S⁺(CH₃)— | 2 | —C₆H₄—N(CH₂CH₂Cl)₂ (meta) | 0 |
| 1051 | morpholino-N— | 2 | —C₆H₄—N(CH₂CH₂Cl)₂ | 0 |
| 1052 | morpholino-N— | 2 | —C₆H₄—N(CH₂CH₂Cl)₂ | 3 |
| 1053 | morpholino-N— | 2 | —C₆H₃(CH₃)—N(CH₂CH₂Cl)₂ | 0 |

TABLE 1-continued

| # | Structure 1 | n | Structure 2 | m |
|---|---|---|---|---|
| 1054 | morpholine N— | 2 | 4-(N(CH₂CH₂Cl)₂)-2-Cl-phenyl | 0 |
| 1055 | morpholine N— | 2 | 3-(N(CH₂CH₂Cl)₂)-phenyl | 0 |
| 1056 | morpholine N⁺—CH₃ | 2 | 4-(N(CH₂CH₂Cl)₂)-phenyl | 0 |
| 1057 | morpholine N⁺—CH₃ | 2 | 4-(N(CH₂CH₂Cl)₂)-phenyl | 3 |
| 1058 | morpholine N⁺—CH₃ | 2 | 4-(N(CH₂CH₂Cl)₂)-2-CH₃-phenyl | 0 |
| 1059 | morpholine N⁺—CH₃ | 2 | 4-(N(CH₂CH₂Cl)₂)-2-Cl-phenyl | 0 |
| 1060 | morpholine N⁺—CH₃ | 2 | 3-(N(CH₂CH₂Cl)₂)-phenyl | 0 |
| 1061 | 3-pyridyl | 1 | 4-(N(CH₂CH₂Cl)₂)-phenyl | 0 |
| 1062 | 3-pyridyl | 1 | 4-(N(CH₂CH₂Cl)₂)-phenyl | 3 |
| 1063 | 3-pyridyl | 1 | 4-(N(CH₂CH₂Cl)₂)-2-CH₃-phenyl | 0 |
| 1064 | 3-pyridyl | 1 | 4-(N(CH₂CH₂Cl)₂)-2-Cl-phenyl | 0 |
| 1065 | 3-pyridyl | 1 | 3-(N(CH₂CH₂Cl)₂)-phenyl | 0 |

TABLE 1-continued
| No. | Structure 1 | | Structure 2 | |
|---|---|---|---|---|
| 1066 | 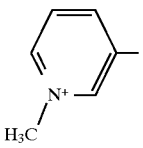 | 1 | 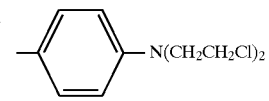 | 0 |
| 1067 | 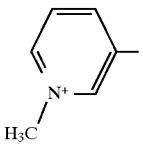 | 1 | 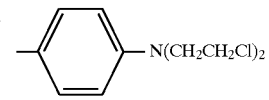 | 3 |
| 1068 | 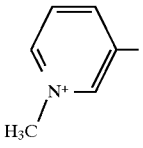 | 1 | 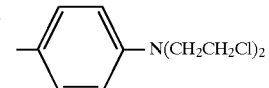 | 0 |
| 1069 | 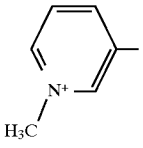 | 1 | 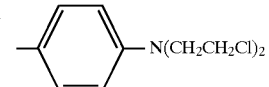 | 0 |
| 1070 | 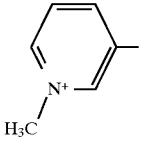 | 1 | 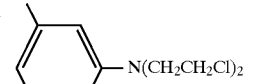 | 0 |
| 1071 | 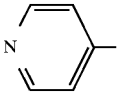 | 1 | 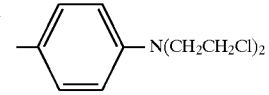 | 0 |
| 1072 | 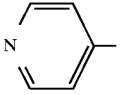 | 1 | 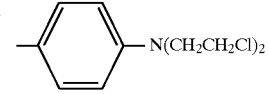 | 3 |
| 1073 | 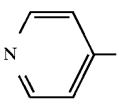 | 1 | 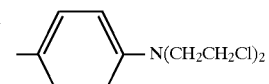 | 0 |
| 1074 | 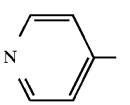 | 1 | 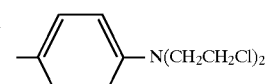 | 0 |
| 1075 | 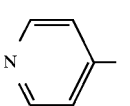 | 1 |  | 0 |
| 1076 | 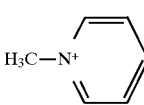 | 1 | 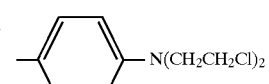 | 0 |
| 1077 | 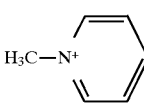 | 1 | 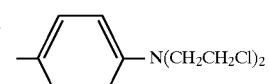 | 3 |

TABLE 1-continued

| | | | | |
|---|---|---|---|---|
| 1078 | H₃C—N⁺(pyridinium)— | 1 | —C₆H₃(2-CH₃)—N(CH₂CH₂Cl)₂ | 0 |
| 1079 | H₃C—N⁺(pyridinium)— | 1 | —C₆H₃(2-Cl)—N(CH₂CH₂Cl)₂ | 0 |
| 1080 | H₃C—N⁺(pyridinium)— | 1 | —C₆H₄(meta)—N(CH₂CH₂Cl)₂ | 0 |
| 1081 | H₃C—S⁺(CH₃)— | 1 | —C₆H₄—N(CH₂CH₂Cl)₂ | 0 |
| 1082 | H₃C—S⁺(CH₃)— | 1 | —C₆H₄—N(CH₂CH₂Cl)₂ | 3 |
| 1083 | H₃C—S⁺(CH₃)— | 1 | —C₆H₃(2-CH₃)—N(CH₂CH₂Cl)₂ | 0 |
| 1084 | H₃C—S⁺(CH₃)— | 1 | —C₆H₃(2-Cl)—N(CH₂CH₂Cl)₂ | 0 |
| 1085 | H₃C—S⁺(CH₃)— | 1 | —C₆H₄(meta)—N(CH₂CH₂Cl)₂ | 0 |
| 1086 | H₃C—S⁺(CH₃)— | 3 | —C₆H₄—N(CH₂CH₂Cl)₂ | 0 |
| 1087 | H₃C—S⁺(CH₃)— | 3 | —C₆H₄—N(CH₂CH₂Cl)₂ | 3 |
| 1088 | H₃C—S⁺(CH₃)— | 3 | —C₆H₃(2-CH₃)—N(CH₂CH₂Cl)₂ | 0 |
| 1089 | H₃C—S⁺(CH₃)— | 3 | —C₆H₃(2-Cl)—N(CH₂CH₂Cl)₂ | 0 |

TABLE 1-continued

| | | | | |
|---|---|---|---|---|
| 1090 |  H₃C—S⁺— with CH₃ | 3 | 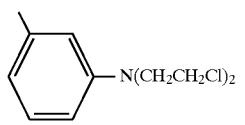 —⟨phenyl⟩—N(CH₂CH₂Cl)₂ (meta) | 0 |
| 1091 | H₃C—S— | 2 | 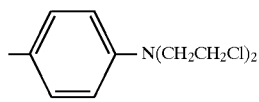 —⟨phenyl⟩—N(CH₂CH₂Cl)₂ | 0 |
| 1092 | H₃C—S— | 2 | 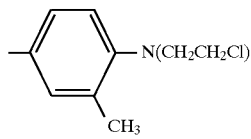 —⟨phenyl⟩—N(CH₂CH₂Cl)₂ with CH₃ | 0 |
| 1093 | H₃C—S— | 2 | 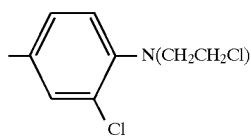 —⟨phenyl⟩—N(CH₂CH₂Cl)₂ with Cl | 0 |
| 1094 | Cl— | 2 | 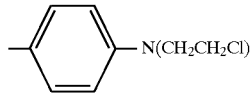 —⟨phenyl⟩—N(CH₂CH₂Cl)₂ | 0 |
| 1095 | 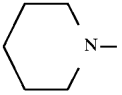 piperidinyl-N— | 2 | 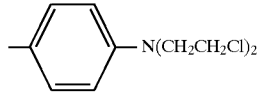 —⟨phenyl⟩—N(CH₂CH₂Cl)₂ | 0 |
| 1096 | 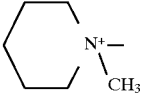 N-methylpiperidinium | 2 | 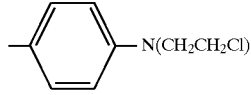 —⟨phenyl⟩—N(CH₂CH₂Cl)₂ | 0 |
| 1097 | 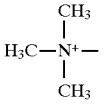 H₃C—N⁺(CH₃)₂— | 3 | 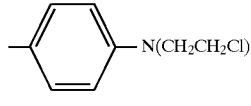 —⟨phenyl⟩—N(CH₂CH₂Cl)₂ | 0 |
| 1098 | 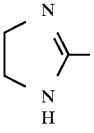 imidazoline | 3 | 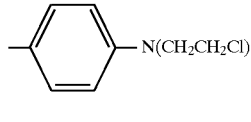 —⟨phenyl⟩—N(CH₂CH₂Cl)₂ | 0 |
| 1099 | 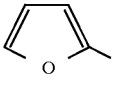 furyl | 0 | 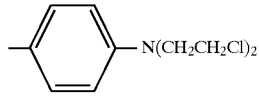 —⟨phenyl⟩—N(CH₂CH₂Cl)₂ | 0 |
| 1100 | 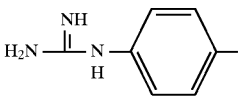 H₂N—C(=NH)—NH—⟨phenyl⟩— | 0 | 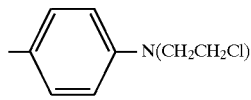 —⟨phenyl⟩—N(CH₂CH₂Cl)₂ | 0 |
| 1101 | 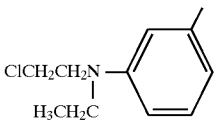 ClCH₂CH₂N(CH₂CH₃)—⟨phenyl⟩— | 2 | 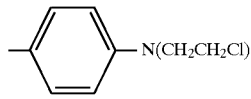 —⟨phenyl⟩—N(CH₂CH₂Cl)₂ | 0 |
| 1102 | 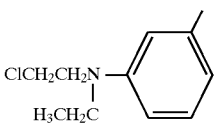 ClCH₂CH₂N(CH₂CH₃)—⟨phenyl⟩— | 4 | 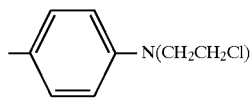 —⟨phenyl⟩—N(CH₂CH₂Cl)₂ | 0 |

TABLE 1-continued
| No. | (structure) | m/k | (structure) | n |
|---|---|---|---|---|
| 1103 | 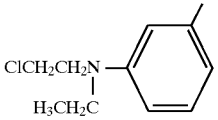 | 5 | 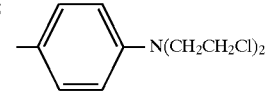 | 0 |
| 1104 |  | 1 | 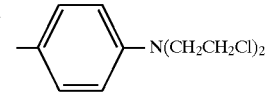 | 0 |
| 1105 |  | 2 | 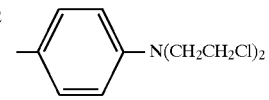 | 0 |
| 1106 |  | 4 | 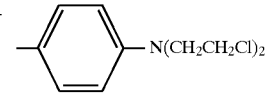 | 0 |
| 1107 |  | 5 | 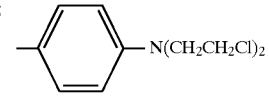 | 0 |
| 1108 | 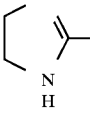 | 1 | 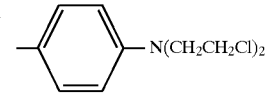 | 0 |
| 1109 | 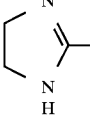 | 2 | 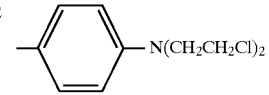 | 0 |
| 1110 | 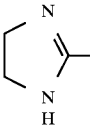 | 3 | 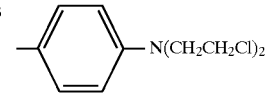 | 0 |
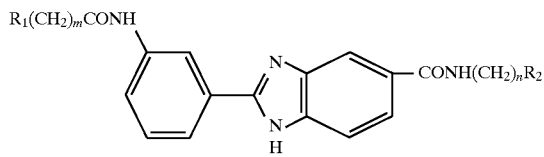
| Compound No. | $R_1$ | m | $R_2$ | n |
|---|---|---|---|---|
| 2001 |  | 1 | 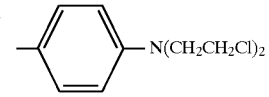 | 0 |
| 2002 |  | 1 | 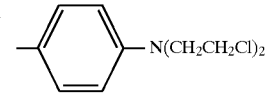 | 2 |
| 2003 |  | 1 | 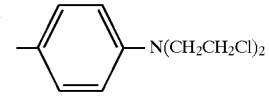 | 3 |

TABLE 1-continued

| | | | | |
|---|---|---|---|---|
| 2004 | H₂N−C(=NH)−NH− | 1 | 4-[N(CH₂CH₂Cl)₂]-2-CH₃-phenyl- | 0 |
| 2005 | H₂N−C(=NH)−NH− | 1 | 4-[N(CH₂CH₂Cl)₂]-2-OCH₃-phenyl- | 0 |
| 2006 | H₂N−C(=NH)−NH− | 1 | 4-[N(CH₂CH₂Cl)₂]-2-Cl-phenyl- | 0 |
| 2007 | H₂N−C(=NH)−NH− | 1 | 4-[N(CH₂CH₂Cl)₂]-3-CH₃-phenyl- | 0 |
| 2008 | H₂N−C(=NH)−NH− | 1 | 4-[N(CH₂CH₂Cl)₂]-3-Cl-phenyl- | 0 |
| 2009 | H₂N−C(=NH)−NH− | 1 | −O−C₆H₄−N(CH₂CH₂Cl)₂ | 1 |
| 2010 | H₂N−C(=NH)−NH− | 1 | 3-[N(CH₂CH₂Cl)₂]-phenyl- | 0 |
| 2011 | H₂N−C(=NH)−NH− | 3 | 4-[N(CH₂CH₂Cl)₂]-phenyl- | 0 |
| 2012 | H₂N−C(=NH)−NH− | 3 | 4-[N(CH₂CH₂Cl)₂]-phenyl- | 2 |
| 2013 | H₂N−C(=NH)−NH− | 3 | 4-[N(CH₂CH₂Cl)₂]-phenyl- | 3 |
| 2014 | H₂N−C(=NH)−NH− | 3 | 4-[N(CH₂CH₂Cl)₂]-2-CH₃-phenyl- | 0 |
| 2015 | H₂N−C(=NH)−NH− | 3 | 4-[N(CH₂CH₂Cl)₂]-2-OCH₃-phenyl- | 0 |

TABLE 1-continued

| | | | | |
|---|---|---|---|---|
| 2016 | H₂N–C(=NH)–NH– | 3 | 4-[N(CH₂CH₂Cl)₂]-2-Cl-C₆H₃– | 0 |
| 2017 | H₂N–C(=NH)–NH– | 3 | 4-[N(CH₂CH₂Cl)₂]-3-CH₃-C₆H₃– | 0 |
| 2018 | H₂N–C(=NH)–NH– | 3 | 3-[N(CH₂CH₂Cl)₂]-4-Cl-C₆H₃– | 0 |
| 2019 | H₂N–C(=NH)–NH– | 3 | –O–C₆H₄–N(CH₂CH₂Cl)₂ | 1 |
| 2020 | H₂N–C(=NH)–NH– | 3 | 3-[N(CH₂CH₂Cl)₂]-C₆H₄– | 0 |
| 2021 | H₂N–C(=NH)– | 3 | 4-[N(CH₂CH₂Cl)₂]-C₆H₄– | 0 |
| 2022 | H₂N–C(=NH)– | 3 | 4-[N(CH₂CH₂Cl)₂]-C₆H₄– | 2 |
| 2023 | H₂N–C(=NH)– | 3 | 4-[N(CH₂CH₂Cl)₂]-C₆H₄– | 3 |
| 2024 | H₂N–C(=NH)– | 3 | 4-[N(CH₂CH₂Cl)₂]-3-CH₃-C₆H₃– | 0 |
| 2025 | H₂N–C(=NH)– | 3 | 4-[N(CH₂CH₂Cl)₂]-3-OCH₃-C₆H₃– | 0 |
| 2026 | H₂N–C(=NH)– | 3 | 4-[N(CH₂CH₂Cl)₂]-2-Cl-C₆H₃– | 0 |
| 2027 | H₂N–C(=NH)– | 3 | 4-[N(CH₂CH₂Cl)₂]-3-CH₃-C₆H₃– | 0 |

TABLE 1-continued

| | | | | |
|---|---|---|---|---|
| 2028 | H₂N−C(=NH)− | 3 | 4-[N(CH₂CH₂Cl)₂]-3-Cl-C₆H₃− | 0 |
| 2029 | H₂N−C(=NH)− | 3 | −O−C₆H₄−N(CH₂CH₂Cl)₂ | 1 |
| 2030 | H₂N−C(=NH)− | 3 | 3-[N(CH₂CH₂Cl)₂]-C₆H₄− | 0 |
| 2031 | (CH₃)₂N− | 3 | 4-[N(CH₂CH₂Cl)₂]-C₆H₄− | 0 |
| 2032 | (CH₃)₂N− | 3 | 4-[N(CH₂CH₂Cl)₂]-C₆H₄− | 2 |
| 2033 | (CH₃)₂N− | 3 | 4-[N(CH₂CH₂Cl)₂]-C₆H₄− | 3 |
| 2034 | (CH₃)₂N− | 3 | 4-[N(CH₂CH₂Cl)₂]-3-CH₃-C₆H₃− | 0 |
| 2035 | (CH₃)₂N− | 3 | 4-[N(CH₂CH₂Cl)₂]-3-OCH₃-C₆H₃− | 0 |
| 2036 | (CH₃)₂N− | 3 | 4-[N(CH₂CH₂Cl)₂]-3-Cl-C₆H₃− | 0 |
| 2037 | (CH₃)₂N− | 3 | 3-[N(CH₂CH₂Cl)₂]-4-CH₃-C₆H₃− | 0 |
| 2038 | (CH₃)₂N− | 3 | 4-[N(CH₂CH₂Cl)₂]-3-Cl-C₆H₃− | 0 |
| 2039 | (CH₃)₂N− | 3 | −O−C₆H₄−N(CH₂CH₂Cl)₂ | 1 |

TABLE 1-continued

| No. | Group 1 | n | Group 2 | m |
|---|---|---|---|---|
| 2040 | H₃C—N(CH₃)— | 3 | 3-CH₃-C₆H₃-N(CH₂CH₂Cl)₂ | 0 |
| 2041 | H₃C—S⁺(CH₃)— | 2 | 4-N(CH₂CH₂Cl)₂-C₆H₄— | 0 |
| 2042 | H₃C—S⁺(CH₃)— | 2 | 4-N(CH₂CH₂Cl)₂-C₆H₄— | 2 |
| 2043 | H₃C—S⁺(CH₃)— | 2 | 4-N(CH₂CH₂Cl)₂-C₆H₄— | 3 |
| 2044 | H₃C—S⁺(CH₃)— | 2 | 4-N(CH₂CH₂Cl)₂-3-CH₃-C₆H₃— | 0 |
| 2045 | H₃C—S⁺(CH₃)— | 2 | 4-N(CH₂CH₂Cl)₂-3-OCH₃-C₆H₃— | 0 |
| 2046 | H₃C—S⁺(CH₃)— | 2 | 4-N(CH₂CH₂Cl)₂-3-Cl-C₆H₃— | 0 |
| 2047 | H₃C—S⁺(CH₃)— | 2 | 3-N(CH₂CH₂Cl)₂-5-CH₃-C₆H₃— | 0 |
| 2048 | H₃C—S⁺(CH₃)— | 2 | 3-N(CH₂CH₂Cl)₂-4-Cl-C₆H₃— | 0 |
| 2049 | H₃C—S⁺(CH₃)— | 2 | —O—C₆H₄-4-N(CH₂CH₂Cl)₂ | 1 |
| 2050 | H₃C—S⁺(CH₃)— | 2 | 3-N(CH₂CH₂Cl)₂-C₆H₄— | 0 |
| 2051 | morpholino-N— | 2 | 4-N(CH₂CH₂Cl)₂-C₆H₄— | 0 |
| 2052 | morpholino-N— | 2 | 4-N(CH₂CH₂Cl)₂-C₆H₄— | 3 |

TABLE 1-continued

| # | Structure 1 | n | Structure 2 | m |
|---|---|---|---|---|
| 2053 | morpholine-N— | 2 | 4-[N(CH₂CH₂Cl)₂]-2-CH₃-phenyl | 0 |
| 2054 | morpholine-N— | 2 | 4-[N(CH₂CH₂Cl)₂]-2-Cl-phenyl | 0 |
| 2055 | morpholine-N— | 2 | 3-[N(CH₂CH₂Cl)₂]-phenyl | 0 |
| 2056 | N-methyl-morpholinium | 2 | 4-[N(CH₂CH₂Cl)₂]-phenyl | 0 |
| 2057 | N-methyl-morpholinium | 2 | 4-[N(CH₂CH₂Cl)₂]-phenyl | 3 |
| 2058 | N-methyl-morpholinium | 2 | 4-[N(CH₂CH₂Cl)₂]-2-CH₃-phenyl | 0 |
| 2059 | N-methyl-morpholinium | 2 | 4-[N(CH₂CH₂Cl)₂]-2-Cl-phenyl | 0 |
| 2060 | N-methyl-morpholinium | 2 | 3-[N(CH₂CH₂Cl)₂]-phenyl | 0 |
| 2061 | pyridyl | 1 | 4-[N(CH₂CH₂Cl)₂]-phenyl | 0 |
| 2062 | pyridyl | 1 | 4-[N(CH₂CH₂Cl)₂]-phenyl | 3 |
| 2063 | pyridyl | 1 | 4-[N(CH₂CH₂Cl)₂]-2-CH₃-phenyl | 0 |
| 2064 | pyridyl | 1 | 4-[N(CH₂CH₂Cl)₂]-2-Cl-phenyl | 0 |

TABLE 1-continued
| | | | | |
|---|---|---|---|---|
| 2065 | 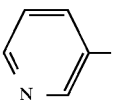 | 1 | 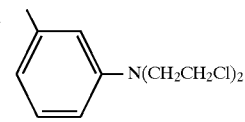 | 0 |
| 2066 | 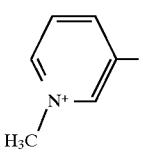 | 1 | 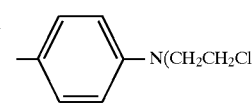 | 0 |
| 2067 | 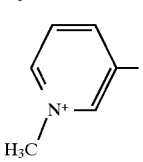 | 1 | 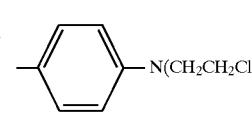 | 3 |
| 2068 | 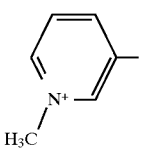 | 1 | 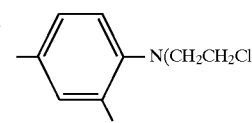 | 0 |
| 2069 | 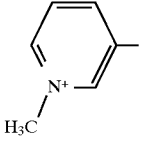 | 1 | 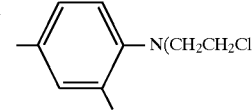 | 0 |
| 2070 | 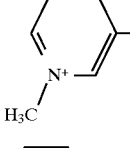 | 1 | 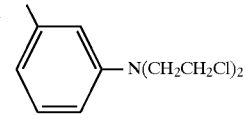 | 0 |
| 2071 | 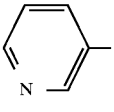 | 1 | 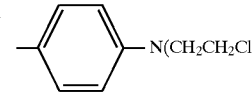 | 0 |
| 2072 | 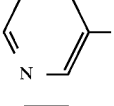 | 1 | 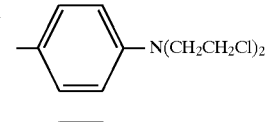 | 3 |
| 2073 | 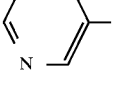 | 1 | 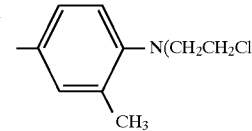 | 0 |
| 2074 | 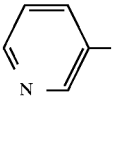 | 1 |  | 0 |
| 2075 | 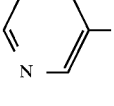 | 1 | 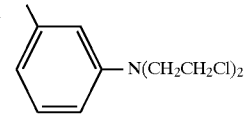 | 0 |
| 2076 | 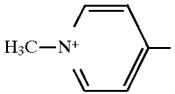 | 1 | 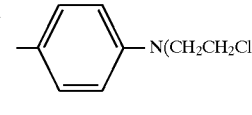 | 0 |

TABLE 1-continued

| | | | |
|---|---|---|---|
| 2077 | H₃C—N⁺(pyridinium)— | 1 | —C₆H₄—N(CH₂CH₂Cl)₂ | 3 |
| 2078 | H₃C—N⁺(pyridinium)— | 1 | —C₆H₃(CH₃)—N(CH₂CH₂Cl)₂ | 0 |
| 2079 | H₃C—N⁺(pyridinium)— | 1 | —C₆H₃(Cl)—N(CH₂CH₂Cl)₂ | 0 |
| 2080 | H₃C—N⁺(pyridinium)— | 1 | —C₆H₄(meta)—N(CH₂CH₂Cl)₂ | 0 |
| 2081 | (CH₃)₂S⁺— | 1 | —C₆H₄—N(CH₂CH₂Cl)₂ | 0 |
| 2082 | (CH₃)₂S⁺— | 1 | —C₆H₄—N(CH₂CH₂Cl)₂ | 3 |
| 2083 | (CH₃)₂S⁺— | 1 | —C₆H₃(CH₃)—N(CH₂CH₂Cl)₂ | 0 |
| 2084 | (CH₃)₂S⁺— | 1 | —C₆H₃(Cl)—N(CH₂CH₂Cl)₂ | 0 |
| 2085 | (CH₃)₂S⁺— | 1 | —C₆H₄(meta)—N(CH₂CH₂Cl)₂ | 0 |
| 2086 | (CH₃)₂S⁺— | 3 | —C₆H₄—N(CH₂CH₂Cl)₂ | 0 |
| 2087 | (CH₃)₂S⁺— | 3 | —C₆H₄—N(CH₂CH₂Cl)₂ | 3 |
| 2088 | (CH₃)₂S⁺— | 3 | —C₆H₃(CH₃)—N(CH₂CH₂Cl)₂ | 0 |

TABLE 1-continued

| | | | | |
|---|---|---|---|---|
| 2089 | H₃C—S⁺— with CH₃ | 3 | 4-N(CH₂CH₂Cl)₂, 3-Cl phenyl | 0 |
| 2090 | H₃C—S⁺— with CH₃ | 3 | 3-N(CH₂CH₂Cl)₂ phenyl | 0 |
| 2091 | H₃C—S— | 2 | 4-N(CH₂CH₂Cl)₂ phenyl | 0 |
| 2092 | H₃C—S— | 2 | 4-N(CH₂CH₂Cl)₂, 3-CH₃ phenyl | 0 |
| 2093 | H₃C—S— | 2 | 4-N(CH₂CH₂Cl)₂, 3-Cl phenyl | 0 |
| 2094 | Cl— | 2 | 4-N(CH₂CH₂Cl)₂ phenyl | 0 |
| 2095 | piperidin-1-yl | 2 | 4-N(CH₂CH₂Cl)₂ phenyl | 0 |
| 2096 | 1-methylpiperidinium-1-yl | 2 | 4-N(CH₂CH₂Cl)₂ phenyl | 0 |
| 2097 | (CH₃)₃N⁺— | 3 | 4-N(CH₂CH₂Cl)₂ phenyl | 0 |
| 2098 | 2-imidazolin-2-yl | 3 | 4-N(CH₂CH₂Cl)₂ phenyl | 0 |
| 2099 | furan-2-yl | 0 | 4-N(CH₂CH₂Cl)₂ phenyl | 0 |
| 2100 | H₂N—C(=NH)—NH—C₆H₄— | 0 | 4-N(CH₂CH₂Cl)₂ phenyl | 0 |
| 2101 | H₂N—C(=NH)—NH— | 2 | 4-N(CH₂CH₂Cl)₂ phenyl | 0 |

TABLE 1-continued

| | | | | |
|---|---|---|---|---|
| 2102 | H₂N—C(=NH)—NH— | 4 | —C₆H₄—N(CH₂CH₂Cl)₂ | 0 |
| 2103 | H₂N—C(=NH)—NH— | 5 | —C₆H₄—N(CH₂CH₂Cl)₂ | 0 |
| 2104 | H₂N—C(=NH)— | 1 | —C₆H₄—N(CH₂CH₂Cl)₂ | 0 |
| 2105 | H₂N—C(=NH)— | 2 | —C₆H₄—N(CH₂CH₂Cl)₂ | 0 |
| 2106 | H₂N—C(=NH)— | 4 | —C₆H₄—N(CH₂CH₂Cl)₂ | 0 |
| 2107 | H₂N—C(=NH)— | 5 | —C₆H₄—N(CH₂CH₂Cl)₂ | 0 |
| 2108 | 2-imidazolin-2-yl (N=C, NH, CH₂CH₂) | 1 | —C₆H₄—N(CH₂CH₂Cl)₂ | 0 |
| 2109 | 2-imidazolin-2-yl | 2 | —C₆H₄—N(CH₂CH₂Cl)₂ | 0 |
| 2110 | 1,4,5,6-tetrahydropyrimidin-2-yl | 3 | —C₆H₄—N(CH₂CH₂Cl)₂ | 0 |

The numbers of compounds in the undermentioned examples correspond to those of the compounds enumerated in Table 1.

EXAMPLE 1 (Compound 47)

1H-2-[3-[[4-[4-[N,N-bis(2-chloroethyl)amino] phenyl]butyryl]amino]phenyl]benzimidazole-5-[N-(2-amidinoethyl]carboxyamide hydrochloride

Reaction 1

1H-2-(3-nitrophenyl)benzimidazole-5-carboxylic acid

In 100 ml of nitrobenzene were dissolved 2.0 g (13.1 mmols, 1.0 eq.) of 3,4-diaminobenzoic acid and 2.0 g (13.2 mmols) of m-nitrobenzaldehyde, and the mixture was then heated and stirred for 21.5 hours in an oil bath at 155° C. The resulting solid was collected by filtration, and then washed with IPA to obtain 1.88 g (6.64 mmols, 50.3%) of the desired compound in the state of yellowish green white crystals.

mp: >270° C.
NMR (DMSO-d$_6$) δ: 9.03 (s, 1H), 8.64 (d, 1H), 8.36 (d, 1H), 8.31–8.17 (m, 1H), 7.89 (t, 2H), 7.80–7.68 (m, 1H)

Reaction 2

1H-2-(3-nitrophenyl)benzimidazole-5-[N-(2-cyanoethyl)]carboxyamide 1.0 g (3.53 mmols) of 1H-2-(3-nitrophenyl) benzimidazole-5-carboxylic acid was suspended in 20 ml of DMF, and 0.69 g (4.26 mmols, 1.2 eq.) of CDI was then added, followed by stirring at room temperature in a nitrogen atmosphere. After 3.5 hours, the solution was cooled on ice. Then, 0.27 ml (3.65 mmols, 1.0 eq.) of β-aminopropionitrile was added to the solution, and the temperature of the solution was then returned to room temperature. After stirring for 3 hours, the solution was then allowed to stand overnight. Next, the solution was concentrated under reduced pressure, and the resulting residue was crystallized from methanol, thereby obtaining 1.08 g (3.19 mmols, 90.4%) of the desired compound in the state of ocher crystals.

mp: >270° C.

NMR (DMSO-d$_6$) δ: 9.04 (s, 1H), 8.90 (m, 1H), 8.64 (d, 1H), 8.37 (d, 1H), 8.25–8.14 (m, 1H), 7.89 (t, 1H), 7.83–7.67 (m, 2H), 3.54 (q, 2H), 2.82 (t, 2H)

Reaction 3

1H-2-(3-nitrophenyl)benzimidazole-5-[N-(2-amidinoethyl)]carboxyamide hydrochloride 1.08 g (3.22 mmols) of 1H-2-(3-nitrophenyl) benzimidazole-5-[N-(2-cyanoethyl)]carboxyamide was suspended in 40 ml of ethanol, and a hydrochloric acid gas was then blown into the suspension under ice cooling. After the suspension was saturated with a hydrochloric acid gas over 30 minutes, the temperature of the suspension was returned to room temperature, followed by stirring for 3 hours. Next, the suspension was concentrated under reduced pressure. The resulting residue was decanted twice with ether and then suspended in 40 ml of ethanol, and an ammonia gas was blown thereinto under ice cooling. After saturated with the ammonia gas over 50 minutes, the suspension was stirred at room temperature for 3 hours, and then allowed to stand overnight. Next, the suspension was concentrated under reduced pressure, and the resulting residue was then sludged with methanol/acetone. The resulting solid was purified through silica gel column chromatography (ethyl acetate/IPA/water=5/2/1), and then sludged with methylene chloride and successively IPA to obtain 0.67 g (1.72 mmols, 53.5%) of the desired compound in the state of creamy crystals.

mp: >270° C.

NMR (DMSO-d$_6$) δ: 9.10–9.06 (m, 3H), 8.88 (t, 0.5H), 8.79 (t, 0.5H), 8.71 (bs, 3H), 8.35 (d, 1H), 8.31 (s, 0.5H), 8.15 (s, 0.5H), 7.88 (t, 1H), 7.88 (d, 1H), 7.75 (d, 0.5H), 7.63 (d, 1H), 3.65 (q, 2H), 2.73 (t, 2H)

Reaction 4

1H-2-[3-[[4-[4-[N,N-bis(2-chloroethyl)amino] phenyl]butyryl]amino]phenyl]benzimidazole-5-[N-(2-amidinoethyl]carboxyamide hydrochloride 0.33 g (0.83 mmol) of 1H-2-(3-nitrophenyl) benzimidazole-5-[N-(2-amidinoethyl)]carboxyamide hydrochloride was suspended in a mixed solvent of DMF and methanol, and catalytic hydrogenation was then carried out in the presence of 10% Pd/C as a catalyst to lead the above-mentioned compound to a corresponding amino compound. This DMF solution was stirred under ice cooling and under a nitrogen gas stream, and a methylene chloride solution of 4-[4-[N,N-bis(2-chloroethyl)amino]phenyl] butyryl chloride {which was prepared by adding 0.55 g (4.6 mmols, 5.0 eq.) of thionyl chloride to 0.28 g (0.92 mmol) of chlorambucil, removing thionyl chloride under reduced pressure after 5 minutes, and then carrying out azeotropic distillation with benzene twice} was added dropwise. The temperature of the suspension was returned to room temperature, followed by stirring for 7 hours. Next, the suspension was concentrated under reduced pressure, and the resulting residue was then purified through silica gel column chromatography (ethyl acetate/IPA/water=6/2/1), and then solidified with ethanol to obtain 0.23 g (0.36 mmols, 43.4%) of the desired compound in the state of light yellowish white crystals.

mp: A definite melting point was not present.

NMR (DMSO-d$_6$) δ: 10.31 (s, 1H), 9.09 (s, 2H), 8.98 (t, 1H), 8.68 (s, 1H), 8.66 (s, 2H), 8.27 (s, 1H), 7.97 (d, 2H), 7.78 (d, 1H), 7.70 (d, 1H), 7.58 (t, 1H), 7.07 (d, 2H), 6.68 (d, 2H), 3.65 (m, 2H), 2.72 (t, 2H), 2.55 (m, 2H), 2.40 (t, 2H), 1.89 (m, 2H)

IR (KBr) cm$^{-1}$: 3064, 1690, 1519, 1310, 1245, 810, 723

Elemental analysis: (C$_{31}$H$_{35}$Cl$_2$N$_7$O$_2$.2HCl.3H$_2$O) Calcd.: C:50.62, H:5.89, N:13.33, Cl:19.28 Found: C:50.36, H:5.61, N:12.77, Cl:19.76

EXAMPLE 2 (Compound 2)

1H-2-[4-[[4-[4-[N,N-bis(2-chloroethyl)amino] phenyl]butyryl]amino]phenyl]benzimidazole-5-[N-(2-amidinoethyl]carboxyamide hydrochloride Reaction 1

Methyl 3,4-diaminobenzoate 3.0 g of 3,4-diaminobenzoic acid was suspended in methanol, and 1.86 ml of thionyl chloride was then added dropwise. Afterward, thionyl chloride was further added as much as 0.5 ml twice, and the suspension was then heated under reflux for 11 hours. Next, thionyl chloride and methanol were distilled off, and the residue was dissolved in methylene chloride, washed with a 0.5N aqueous sodium hydroxide solution and a saturated sodium chloride solution, and then dried over sodium sulfate. After the solvent was distilled off, the residue was sludged with n-hexane to obtain 3.04 g (93%) of the desired compound.

NMR (CDCl$_3$) δ: 7.47 (dd, 1H), 7.41 (d, 1H), 6.67 (d, 1H), 3.85 (s, 3H)

Reaction 2

Methyl 1H-2-(4-nitrophenyl)benzimidazole-5-carboxylate

In 60 ml of nitrobenzene were dissolved 1.0 g (6.0 mmols) of methyl 3,4-diaminobenzoate and 0.91 g (6.0 mmols) of p-nitrobenzaldehyde (slightly undissolved), and the solution was then heated in an oil bath at 150° C. for 39 hours. Next, the solution was cooled with ice water, and the resulting crystals were collected by filtration to obtain 1.54 g (5.2 mmols, 86.5%) of the desired compound in the state of brown crystals.

mp: >280° C.

NMR (DMSO-d$_6$) δ: 8.44 (d, 2H), 8.31 (d, 2H), 8.16 (s, 1H), 7.9–7.7 (m, 2H), 3.9 (s, 3H)

Reaction 3

1H-2-(4-nitrophenyl)benzimidazole-5-carboxylic acid

In 20 ml of methanol was suspended 1.0 g (3.4 mmols) of methyl 1H-2-(4-nitrophenyl)benzimidazole-5-carboxylate, and 20 ml of a 1N aqueous sodium hydroxide solution was then added, followed by heating and stirring at 60° C. for 1 hour. Next, an amount corresponding to that of methanol was distilled off under reduced pressure. Water was added to the remaining reaction solution, and the solution was then acidified with 4N hydrochloric acid. Afterward, the resulting crystals were collected by filtration to obtain 0.94 g (3.3 mmols, 97.6%) of the desired compound in the state of yellowish white crystals.

mp: >278° C.

NMR (DMSO-d$_6$) δ: 8.47 (d, 2H), 8.43 (d, 2H), 8.25 (s, 1H), 7.9 (d, 1H), 7.7 (d, 1H)

Reaction 4

1H-2-(4-nitrophenyl)benzimidazole-5-[N-(2-cyanoethyl)]carboxyamide

In 42 ml of DMF was dissolved 0.48 g (1.69 mmols) of 1H-2-(4-nitrophenyl)benzimidazole-5-carboxylic acid, and 0.33 g (2.04 mmols, 1.2 eq.) of CDI was added, followed by stirring at room temperature under a nitrogen gas stream. After 3 hours, the solution was cooled on ice, and 0.14 ml (1.9 mmols, 1.1 eq.) of β-aminopropionitrile was then added. Next, the solution was stirred for 3 hours at room temperature and allowed to stand overnight. After concentration under reduced pressure, the resulting residue was sludged with methanol to obtain 0.47 g (1.4 mmols, 82.9%) of the desired compound in the state of yellow crystals.

mp: >270° C.

NMR (DMSO-$d_6$) δ: 8.94–8.9 (m, 1H), 8.45 (s, 4H), 8.3 (s, 0.5H), 8.1 (s, 0.5H), 7.85 (d, 0.5H), 7.65 (d, 0.5H), 3.54 (q, 2H), 2.82 (t, 2H)

Reaction 5

1H-2-(4-nitrophenyl)benzimidazole-5-[N-(2-amidinoethyl)]carboxyamide hydrochloride In 10 ml of ethanol was suspended 0.47 g (1.4 mmols) of 1H-2-(4-nitrophenyl)benzimidazole-5-[N-(2-cyanoethyl)] carboxyamide, and a hydrochloric acid gas was blown into the suspension over 30 minutes under ice cooling to saturate the suspension with the gas. Afterward, the suspension was stirred at room temperature for 2 hours to precipitate a solid after it was once dissolved. After concentration under reduced pressure, the resulting residue was sludged with ether, collected by filtration, and then suspended in 15 ml of ethanol. Next, an ammonia gas was blown into the suspension over 2 hours to saturate it with the gas, whereby a solid was precipitated after it was once dissolved. The reaction system was allowed to stand overnight, as it was. Next, methanol and acetone were added to the reaction solution, and the undissolved precipitate was collected by filtration to obtain 0.42 g (1.1 mmols, 77.9%) of the desired compound in the state of yellow crystals.

mp: >279° C.

NMR (DMSO-$d_6$) δ: 9.5 (bs, 3H), 8.83 (m, 1H), 8.5 (d, 2H), 8.43 (s, 1H), 8.24 (s, 1H), 7.83 (d, 1H), 7.7 (d, 1H), 3.65 (m, 2H), 2.72 (t, 2H)

Reaction 6

1H-2-[4-[[4-[4-[N,N-bis(2-chloroethyl)amino]phenyl]butyryl]amino]phenyl]benzimidazole-5-[N-(2-amidinoethyl]carboxyamide hydrochloride 0.24 g (3.3 mmols) of thionyl chloride was added to 0.12 g (0.39 mmol) of chlorambucil, and the mixture was then stirred at room temperature for 5 minutes. Next, thionyl chloride was distilled off under reduced pressure and further removed by doing azeotropic distillation with benzene twice, and methylene chloride was then added. This solution was added to a DMF solution containing 0.54 mmol of 1H-2-(4-aminophenyl)benzimidazole-5-[N-(2-amidinoethyl]carboxyamide hydrochloride (which was obtained by subjecting the nitro compound of Reaction 5 to catalytic hydrogenation using 10% Pd/C as a catalyst) under ice cooling, and the solution was stirred at room temperature for 5 hours and then allowed to stand overnight. Next, a formed solid was removed by filtration, and the filtrate was then concentrated under reduced pressure. The resulting residue was purified through silica gel column chromatography (methylene chloride/methanol/acetic acid=80/20/1), and then crystallized from ether, thereby obtaining 71 mg (0.11 mmols, 20.4%) of the desired compound in the state of light brown crystals.

mp: Decomposed from 209° C.

NMR (DMSO-$d_6$) δ: 10.4 (s, 1H), 9.07 (s, 2H), 8.97 (m, 1H), 8.64 (s, 2H), 8.29 (d, 2H), 8.24 (s, 1H), 7.95 (d, 1H), 7.87 (d, 2H), 7.77 (d, 1H), 7.07 (d, 2H), 6.67 (d, 2H), 3.70 (s, 8H), 3.64 (m, 2H), 2.71 (m, 2H), 2.39 (m, 2H), 1.88 (m, 2H)

IR (KBr) cm$^{-1}$: 3100, 1686, 1519, 1322, 1258, 1193, 843, 740

Elemental analysis: ($C_{31}H_{35}Cl_2N_7O_2 \cdot 2HCl \cdot 3H_2O$) Calcd.: C:50.62, H:5.89, N:13.33, Cl:19.28 Found: C:50.68, H:5.48, N:13.63, Cl:18.88

EXAMPLE 3 (Compound 90)

2-[3-(formylamino)phenyl]benzimidazole-5-[N-(2-amidinoethyl]carboxyamide hydrochloride Reaction 1

1H-2-(3-nitrophenyl)benzimidazole-5-[N-(2-amidinoethyl)]carboxyamide hydrochloride In 40 ml of ethanol was suspended 1.08 g (3.22 mmols) of 1H-2-(3-nitrophenyl)benzimidazole-5-[N-(2-cyanoethyl)]carboxyamide, and a hydrochloric acid gas was blown into the suspension over 30 minutes under ice cooling to saturate the suspension with the gas. Next, the temperature of the suspension was returned to room temperature, and after stirring for 3 hours, the suspension was concentrated under reduced pressure. The resulting residue was decanted twice with ether and then suspended in 40 ml of ethanol, and an ammonia gas was blown thereinto under ice cooling over 50 minutes to saturate the suspension with the ammonia gas. Afterward, the temperature of the suspension was returned to room temperature, and the suspension was stirred for 3 hours and then allowed to stand overnight. Next, the suspension was concentrated under reduced pressure, and the resulting residue was then sludged with methanol/acetone. The resulting solid was purified through silica gel column chromatography (ethyl acetate/IPA/water=5/2/1), and then sludged with methylene chloride and IPA to obtain 0.67 g (1.72 mmols, 53.5%) of the desired compound in the state of creamy crystals.

mp: >270° C.

NMR (DMSO-$d_6$) δ: 9.10–9.06 (m, 3H), 8.88 (t, 0.5H), 8.79 (t, 0.5H), 8.71 (bs, 3H), 8.35 (d, 1H), 8.31 (s, 0.5H), 8.15 (s, 0.5H), 7.88 (t, 1H), 7.88 (d, 1H), 7.75 (d, 0.5H), 7.63 (d, 1H), 3.65 (q, 2H), 2.73 (t, 2H)

Reaction 2

1H-2-[3-(formylamino)phenyl]benzimidazole-5-[N-(2-amidinoethyl)]carboxyamide hydrochloride In a mixed solvent of 8 ml of DMF and 8 ml of methanol was suspended 0.65 g (1.67 mmols) of 1H-2-(3-nitrophenyl) benzimidazole-5-[N-(2-amidinoethyl)]carboxyamide hydrochloride, and catalytic hydrogenation was then carried out by using 0.28 g of 10% Pd/C as a catalyst. Next, the suspension was concentrated under reduced pressure, and to an ½ amount (a solution containing about 4 ml of DMF) of the concentrated suspension, a formylimidazole-THF solution [which was prepared by adding 0.16 ml (4.2 mmols) of formic acid to a mixture of 0.67 g (4.1 mmols) of CDI and 12 ml of THF, and then stirring the solution at room temperature in a nitrogen atmosphere for 1 hour] was added dropwise under ice cooling in a nitrogen atmosphere, and the temperature of the suspension was returned to room temperature. Afterward, the suspension was stirred for 5 hours and then allowed to stand overnight. Next, the suspension was concentrated under reduced pressure, and the resulting residue was purified through silica gel column chromatography (ethyl acetate/IPA/H$_2$O=6/2/1) and further purified preparative TLC (ethyl acetate/IPA/H$_2$O=5/2/1) twice, and then solidified with IPA-ether to obtain 17 mg (0.044 mmol, 5.3%) of the desired compound in the state of yellow amorphous powder.

NMR (DMSO-d$_6$) δ: 10.31 (s, 1H), 9.09 (s, 2H), 8.98 (t, 1H), 8.68 (s, 1H), 8.66 (s, 2H), 8.27 (s, 1H), 7.97 (d, 2H), 7.78 (d, 1H), 7.70 (d, 1H), 7.58 (t, 1H), 7.07 (d, 2H), 6.68 (d, 2H), 3.65 (m, 2H), 2.72 (t, 2H), 2.55 (m, 2H), 2.40 (t, 2H), 1.89 (m, 2H)

IR (KBr) cm$^{-1}$: 3064, 1690, 1519, 1310, 1245, 810, 723

Elemental analysis: (C$_{31}$H$_{35}$Cl$_2$N$_7$O$_2$.2HCl.3H$_2$O) Calcd.: C:50.62, H:5.89, N:13.33, Cl:19.28 Found: C:50.36, H:5.61, N:12.77, Cl:19.76

EXAMPLE 4 (Compound 45)

2-[4-(formylamino)phenyl]benzimidazole-5-[N-(2-amidinoethyl]carboxyamide hydrochloride Reaction 1

1H-2-(4-aminophenyl)benzimidazole-5-[N-(2-amidinoethyl)]carboxyamide hydrochloride In a mixed solvent of 4 ml of DMF and 4 ml of methanol was dissolved 0.42 g (1.08 mmols) of 1H-2-(4-nitrophenyl) benzimidazole-5-[N-(2-amidinoethyl)]carboxyamide hydrochloride, and catalytic hydrogenation was then carried out by using 0.18 g of 10% Pd/C as a catalyst. After the removal of the catalyst, methanol was distilled off, and the half of the solution containing DMF was taken out and used in the next reaction.

Reaction 2

1H-2-[4-(formylamino)phenyl]benzimidazole-5-[N-(2-amidinoethyl)]carboxyamide hydrochloride A solution, which had been prepared by adding 0.10 ml (2.65 mmols) of formic acid to 4 ml of a THF solution containing 0.44 g (2.7 mmols) of CDI and then stirring the solution at room temperature for 30 minutes under a nitrogen gas stream, was added dropwise to a DMF solution containing 0.54 mmol of 1H-2-(4-aminophenyl) benzimidazole-5-[N-(2-amidinoethyl)]carboxyamide hydrochloride under ice cooling under a nitrogen gas stream with stirring. Afterward, the temperature of the solution was returned to room temperature, followed by stirring for 6.5 hours. Next, the solution was concentrated under reduced pressure, and the resulting residue was purified through reversed phase silica gel column chromatography (ODS, water/methanol=50%), and then crystallized from ethanol-ether to obtain 36 mg (0.093 mmol, 17.2%) of the desired compound in the state of white crystals.

mp: 220°–229° C.

NMR (DMSO-d$_6$, 80° C.) δ: 10.80 (s, 1H), 9.06 (bs, 2H), 8.80 (bs, 3H), 8.40 (s, 1H), 8.17 (d, 1H), 8.12 (s, 1H), 7.93 (d, 2H), 7.72 (d, 1H), 6.83 (d, 2H), 3.45 (m, 2H), 2.44 (m, 2H)

IR (KBr) cm$^{-1}$: 3422, 1648, 1606, 1499, 1400, 1195, 840

EXAMPLE 5 (Compound 44)

1H-2-[4-(formylamino)phenyl]benzimidazole-5-[N-(3-(dimethylamino)propyl]]carboxyamide Reaction 1

1H-2-(4-nitrophenyl)benzimidazole-5-[N-[3-(dimethylamino)propyl]]carboxyamide

In 50 ml of DMF was dissolved 0.50 g (1.77 mmols) of 1H-2-(4-nitrophenyl)benzimidazole-5-carboxylic acid, and 0.34 g (2.1 mmols, 1.2 eq.) of CDI was added, followed by stirring at room temperature in a nitrogen atmosphere. After 4 hours, the solution was cooled on ice. Then, 0.24 ml (1.9 mmols, 1.1 eq.) of N,N-dimethyl-1,3-propanediamine was added to the solution, and the temperature of the solution was returned to room temperature and the solution was then allowed to stand overnight. After the completion of the reaction had been confirmed, the solution was concentrated under reduced pressure, and the resulting residue was sludged with methanol to obtain 0.52 g (1.42 mmols, 80.2%) of the desired compound in the state of yellowish white crystals.

mp: 261°–265° C.

NMR (DMSO-d$_6$) δ: 8.57 (t, 1H), 8.45 (s, 4H), 8.17 (s, 1H), 7.80 (d, 1H), 7.71 (d, 1H), 3.33 (q, 2H), 2.30 (t, 2H), 1.70 (m, 2H)

Reaction 2

1H-2-[4-(formylamino)phenyl]benzimidazole-5-[N-(3-(dimethylamino)propyl]]carboxyamide In a mixed solvent of 6 ml of DMF and 4 ml of methanol was suspended 0.18 g (0.49 mmol) of 1H-2-(4-nitrophenyl) benzimidazole-5-[N-[3-(dimethylamino)propyl]] carboxyamide, and catalytic hydrogenation was then carried out by the use of 10% Pd/C as a catalyst to lead it to a corresponding amino compound. This compound was dissolved in 8 ml of DMF and then ice-cooled, and a formylimidazole/THF solution [0.38 g (2.34 mmols) of CDI, prepared from 88 μl of formic acid and 4 ml of THF] was added dropwise under a nitrogen gas stream. Next, the temperature of the solution was returned to room temperature, and the solution was stirred for 7.5 hours and then allowed to stand overnight. After concentration under reduced pressure, the resulting residue was purified through alumina column chromatography (ICN, Almina N, adjusted to Grade 3 by adding water) (chloroform/methanol=8–10%), and then crystallized from ethanol-ether to obtain 0.11 g (0.30 mmol, 64.0%) of the desired compound in the state of yellowish white crystals.

mp: 126°–132° C.

NMR (DMSO-d$_6$) δ: 10.43 (s, 1H), 8.45 (bs, 1H), 8.35 (s, 0.5H), 7.98 (s, 0.5H), 8.14 (d, 2H), 7.77 (d, 2H), 7.68 (bs, 1H), 7.54 (d, 0.5H), 7.40 (d, 0.5H), 3.32 (m, 2H), 2.29 (t, 2H), 2.16 (s, 3H)

IR (KBr) cm$^{-1}$: 3379, 2949, 1692, 1608, 1545, 1290, 844, 737

Elemental analysis: (C$_{20}$H$_{23}$N$_5$O$_2$.0.5H$_2$O) Calcd.: C:64.15, H:6.46, N:18.70 Found: C:64.25, H:6.67, N:18.50

EXAMPLE 6 (Compound 29)

1H-2-[4-[[4-[4-[N,N-bis(2-chloroethyl)amino]phenyl] butyryl]amino]phenyl]benzimidazole-5-[N-[3-(dimethylamino)propyl]]carboxyamide In a mixed solvent of 6 ml of DMF and 4 ml of methanol was suspended 0.15 g (0.41 mmol) of 1H-2-(4-nitrophenyl) benzimidazole-5-[N-[3-(dimethylamino)propyl]] carboxyamide, and catalytic hydrogenation was then carried out by the use of 10% Pd/C as a catalyst to lead it to a corresponding amino compound. Next, this compound was dissolved in 8 ml of DMF, and 0.12 g (0.39 mmol, 0.96 eq.) of chlorambucil and 61 mg (0.45 mmol, 1.1 eq.) of HOBt were then added. Afterward, 96 mg (0.47 mmol, 1.1 eq.) of DCC was further added under ice cooling in a nitrogen atmosphere, and the temperature of the solution was returned to room temperature. Next, the solution was stirred for 7 hours and then allowed to stand overnight. Since the reaction did not complete, a solution prepared by the following procedure was added to the reaction system, followed by stirring for 10 hours. The above-mentioned solution was prepared by reacting 0.12 g (0.39 mmol, 0.95 eq.) of chlorambucil with 0.24 g of thionyl chloride at room temperature for 5 minutes, removing thionyl chloride by azeotropic distillation with benzene, and then dissolving the thionyl chloride-free material in methylene chloride. After the completion of the reaction had been confirmed, the resulting solid was removed by filtration, and the filtrate was then concentrated under reduced pressure. Afterward, the resulting residue was purified through alumina column chromatography (ICN, Almina N, methylene chloride/methanol= 2%), and then crystallized from ether to obtain 0.13 g (0.21 mmol, 51.2%) of the desired compound in the state of white crystals.

mp: 200°–210° C. (decomposed)

NMR (DMSO-$d_6$) δ: 10.14 (s, 1H), 8.54–8.5 (m, 1H), 8.15 (s, 0.5H), 8.00 (S, 0.5H), 8.10 (d, 1H), 7.80 (d, 2H), 7.70–7.51 (m, 2H), 7.12 (d, 2H), 6.71 (d, 2H), 3.70 (s, 8H), 3.34–3.36 (m, 2H), 2.53 (m, 2H), 2.41–2.33 (m, 4H), 2.17 (s, 6H), 1.92 (m, 2H), 1.70 (m, 2H)

IR (KBr) $cm_{-1}$: 2947, 1615, 1519, 1311, 1252, 846

Elemental analysis: ($C_{33}H_{40}Cl_2N_6O_2$) Calcd.: C:63.56, H:6.46, N:13.48 Found: C:63.10, H:6.53, N:13.15

EXAMPLE 7 (Compound 1001)

1H-2-[4-(guanidinoacetylamino)phenyl] benzimidazole-5-[N-[4-[N,N-bis(2-chloroethyl) amino)phenyl]]carboxyamide dihydrochloride Reaction 1

1H-2-(4-nitrophenyl)benzimidazole-5-[N-[4-[N,N-bis (2-chloroethyl)amino]phenyl]]carboxyamide In 8 ml of DMF were suspended 0.26 g (0.96 mmol) of 1H-2-(4-nitrophenyl)benzimidazole-5-carboxylic acid and 0.27 g (0.95 mmol) of N,N-bis(2-chloroethyl)-1,4-phenylenediamine hydrochloride, and the solution was then stirred under a nitrogen gas stream, while cooled on ice. Next, 0.40 ml (2.87 mmols, 3.0 eq.) of triethylamine and 0.22 ml (1.45 mmols, 1.5 eq.) of DECP were added in this order, and the solution was stirred for 3 hours and then allowed to stand overnight, as it was. After concentration under reduced pressure, the resulting residue was sludged with methanol to obtain 0.33 g (0.66 mmol, 69.7%) of the desired compound in the state of light brown crystals.

mp: >250° C.

NMR (DMSO-$d_6$) δ: 10.11 (s, 0.5H), 10.05 (s, 0.5H), 8.46 (s, 4H), 8.42 (s, 0.5H), 8.17 (s, 0.5H), 7.95–7.84 (m, 1.5H), 7.68 (d, 0.5H), 6.77 (d, 2H), 6.64 (d, 2H), 3.74 (s, 8H)

Reaction 2

1H-2-[4-(guanidinoacetylamino)phenyl] benzimidazole-5-[N-[4-[N,N-bis(2-chloroethyl) aminophenyl]]carboxyamide dihydrochloride 0.12 ml of 1N hydrochloric acid was added to a solution composed of a mixed solvent of DMF and methanol and 50 mg (0.10 mmol) of 1H-2-(4-nitrophenyl)benzimidazole-5-[N-[ 4-[N,N-bis(2-chloroethyl)amino]phenyl]] carboxyamide. Then the mixture was subjected to catalytic hydrogenation in the presence of 10% Pd/C as a catalyst to lead it to a corresponding amino compound. Next, the DMF solution of this amino compound was stirred under a nitrogen gas stream while cooled on ice, and 20 μl (0.14 mmol, 1.4 eq.) of triethylamine, 46 mg (0.30 mmol, 3.0 eq.) of guanidineacetic acid hydrochloride and 62 mg (0.30 mmol, 3.0 eq.) of DCC were added in this order. Afterward, the temperature of the solution was returned to room temperature, and the solution was stirred for 2 hours and then allowed to stand overnight. After the removal of a formed solid by filtration, the filtrate was then concentrated under reduced pressure. The resulting residue was subjected ejected to gel filtration (Sephadex LH-20, methanol), and 4N hydrochloric acid and dioxane were added to the eluted fraction. Next, the solution was concentrated and then sludged with methanol to obtain 10 mg (0.016 mmol, 15.6%) of the desired compound in the state of white crystals.

mp: 215°–227° C. (decomposed)

NMR (DMSO-$d_6$) δ: 10.30 (s, 1H), 8.35 (d, 2H), 8.32 (s, 1H), 8.05 (d, 1H), 7.93 (d, 2H), 7.83 (d, 1H), 7.63 (d, 3H), 7.50–7.20 (bs, 4H), 6.78 (d, 2H), 4.16 (d, 2H), 3.74 (s, 8H)

IR (KBr) $cm^{-1}$: 3332, 1652, 1602, 1516, 1328, 737

EXAMPLE 8 (Compound 1010)

1H-2-[4-(guanidinoacetylamino)phenyl] benzimidazole-5-[N-[3-[N,N-bis(2-chloroethyl) amino]phenyl]]carboxyamide Reaction 1 m-[N,N-bis(2-hydroxyethyl)amino]nitrobenzene

In 36 ml of 30% acetic acid was dissolved 5.0 g (36.2 mmols) of m-aminoitrobenzene, and 22.9 ml of ethylene oxide was further added under ice cooling, followed by stirring at room temperature overnight. After extraction with ethyl acetate, the ethyl acetate layer was dried over sodium sulfate and concentrated. The resulting residue was sludged with ether to obtain 5.21 g (23.0 mmols, 63.6%) in the state of yellow crystals.

mp: 98.5°–100° C.

NMR (DMSO-$d_6$) δ: 7.51 (d, 1H), 7.51 (s, 1H), 7.32 (t, 1H), 6.99 (d, 1H), 3.89 (t, 4H), 3.73 (bs, 2H), 3.65 (t, 4H)

Reaction 2

3-[N,N-bis(2-chloroethyl)amino]nitrobenzene

In 25 ml of toluene was suspended 2.5 g (11.0 mmols) of 3-[N,N-bis(2-hydroxyethyl)amino]nitrobenzene, and 10.2 g (85.7 mmols, 7.8 eq.) of thionyl chloride was added under ice cooling. Next, the suspension was heated and stirred for 5 hours in an oil bath at 70° C. After concentration under reduced pressure, the solution was extracted with ethyl acetate after addition of water. After drying over anhydrous sodium sulfate, the extracted layer was concentrated under reduced pressure, and the resulting residue was then sludged with ether to obtain 2.67 g (10.1 mmols, 92.2%) of the desired compound in the state of yellow crystals.

mp: 112°–113° C.

NMR (CDCl$_3$) δ: 7.61 (d, 1H), 7.50 (t, 1H), 7.39 (t, 1H), 6.98 (d, 1H), 3.83 (t, 4H), 3.68 (t, 4H)

Reaction 3

N,N-bis(2-chloroethyl)-1,3-phenylenediamine hydrochloride

In 35 ml of concentrated hydrochloric acid was dissolved 2.0 g (7.6 mmols) of 3-[N,N-bis(2-chloroethyl)amino]

nitrobenzene, and 6.9 g (30.6 mmols, 4.0 eq.) of stannic chloride (II) dihydrate was added, followed by stirring for 1 hour in an oil bath at 100° C. Next, the solution was allowed to stand until its temperature lowered to room temperature, and then diluted with water. The solution was basified with concentrated ammonia water, extracted with ethyl acetate twice, dried over anhydrous sodium sulfate, and then concentrated under reduced pressure. Afterward, 4N hydrochloric acid and dioxane were added to the resulting residue, and after concentration, the residue was crystallized from a small amount of methanol-ether to obtain 1.97 g (7.3 mmols, 96.1%) of the desired compound in the state of yellow crystals.

mp: 195°–201° C.

NMR (DMSO-$d_6$) δ: 10.30–9.80 (bs, 3H), 7.27 (t, 1H), 6.76 (d, 1H), 6.73 (s, 1H), 6.63 (d, 1H), 3.74 (s, 8H)

Reaction 4

1H-2-(4-nitrophenyl)benzimidazole-5-[N-3-[N,N-bis(2-chloroethyl)amino]phenyl]carboxyamide In 10 ml of DMF were dissolved 0.30 g (1.06 mmols) of 1H-2-(4-nitrophenyl)benzimidazole-5-carboxylic acid and 0.29 g (1.08 mmols, 1.0 eq.) of N,N-bis(2-chloroethyl)-1,3-phenylenediamine hydrochloride, and the solution was then stirred under a nitrogen gas stream, while cooled on ice. Next, 0.44 ml (3.15 mmols, 3.0 eq.) of triethylamine and 0.24 ml (1.58 mmols, 1.5 eq.) of DECP were added in this order, and the solution was stirred for 9 hours and then allowed to stand overnight, as it was. After concentration under reduced pressure, the resulting residue was purified through silica gel column chromatography (chloroform/methanol= 2–4%) and then sludged with ethanol to obtain 0.23 g (0.46 mmol, 43.5%) of the desired compound in the state of yellowish white crystals.

mp: 213°–217° C.

NMR (DMSO-$d_6$) δ: 10.20 (s, 0.5H), 10.11 (s, 0.5H), 8.47 (s, 4H), 8.43 (s, 1H), 8.16 (s, 0.5H), 7.92 (d, 0.5H), 7.86 (s, 0.5H), 7.71 (d, 0.5H), 7.31–7.15 (m, 3H), 6.51 (d, 1H), 3.80–3.74 (m, 8H)

Reaction 5

1H-2-[4-(guanidinoacetylamino)phenyl]benzimidazole-5-[N-[3-[N,N-bis(2-chloroethyl)amino)phenyl]]carboxyamide dihydrochloride In DMF-methanol, 50 mg (0.10 mmol) of 1H-2-(4-nitrophenyl)benzimidazole-5-[N-3-[N,N-bis(2-chloroethyl)amino]phenyl]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 44 mg (0.29 mmol, 2.9 eq.) of guanidineacetic acid hydrochloride and 59 mg (0.29 mmol, 2.9 eq.) of DCC were added in this order. Afterward, the temperature of the solution was returned to room temperature, and the solution was stirred for 5 hours and then allowed to stand overnight. After the removal of a formed solid by filtration, the filtrate was then concentrated under reduced pressure. Next, DMF was added to the residue, and the resulting crystals were removed by filtration. The concentrated residue of the filtrate was subjected to gel filtration (Sephadex LH-20, methanol), and 4N hydrochloric acid and dioxane were added to the eluted fraction, followed by concentration. The concentrated material was crystallized from ether to obtain 31 mg (0.048 mmol, 48.0%) of the desired compound in the state of light yellowish white crystals.

mp: 200°–210° C.

NMR (DMSO-$d_6$) δ: 10.27 (s, 1H), 9.41 (s, 1H), 8.33 (d, 2H), 8.30 (s, 1H), 7.96 (d, 1H), 7.90 (d, 2H), 7.80 (d, 1H), 7.64 (t, 1H), 7.50–7.15 (m, 7H), 6.51 (d, 1H), 4.16 (d, 2H), 3.76 (m, 8H)

IR (KBr) cm$^{-1}$: 3339, 1654, 1604, 1542

EXAMPLE 9 (Compound 2001)

1H-2-[3-(guanidinoacetylamino)phenyl]benzimidazole-5-[N-[4-[N,N-bis(2-chloroethyl)amino)phenyl]]carboxyamide dihydrochloride Reaction 1

1H-2-[3-(nitrophenyl)benzimidazole-5-[N-[4-[N,N-bis(2-chloroethyl)amino]phenyl]]carboxyamide In 12 ml of DMF were dissolved 0.30 g (1.06 mmols) of 1H-2-(3-nitrophenyl)benzimidazole-5-carboxylic acid and 0.29 g (1.08 mmols, 1.0 eq.) of N,N-bis(2-chloroethyl)-1,4-phenylenediamine hydrochloride, and the solution was then stirred under a nitrogen gas stream while cooled on ice. Next, 0.45 ml (3.23 mmols, 3.0 eq.) of triethylamine and 0.24 ml (1.58 mmols, 1.5 eq.) of DECP were added in this order, and the solution was stirred for 3 hours and then allowed to stand overnight, as it was. After concentration under reduced pressure, methanol was added to the resulting residue, and the solution was then allowed to stand for 3 hours. Next, the resulting solid was collected by filtration to obtain 0.45 g (0.90 mmol, 85.2%) of the desired compound in the state of ocherous powder.

mp: A definite melting point was not present.

NMR (DMSO-$d_6$) δ: 10.06 (bs, 1H), 9.06 (s, 1H), 8.66 (d, 1H), 8.38 (d, 1H), 8.38 (s, 0.5H), 8.16 (s, 0.5H), 7.90 (t, 1H), 7.93–7.70 (m, 2H), 7.63 (d, 2H), 6.77 (d, 2H), 3.74 (s, 8H)

Reaction 2

1H-2-[3-(guanidinoacetylamino)phenyl]benzimidazole-5-[N-[4-[N,N-bis(2-chloroethyl)amino]phenyl]]carboxyamide dihydrochloride In DMF-methanol, 0.15 g (0.30 mmol) of 1H-2-[3-(nitrophenyl)benzimidazole-5-[N-[4-[N,N-bis(2-chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 0.14 g (0.91 mmols, 3.0 eq.) of guanidineacetic acid hydrochloride and 0.19 g (0.92 mmol, 3.0 eq.) of DCC were added in this order. Afterward, the temperature of the solution was returned to room temperature, and the solution was stirred for 9 hours and then allowed to stand overnight. After the removal of a formed solid by filtration, the filtrate was concentrated under reduced pressure. Next, the residue was subjected to gel filtration (Sephadex LH-20, methanol), and 4N hydrochloric acid and dioxane were added to the eluted fraction, followed by concentration. The concentrated solution was crystallized from methanol, thereby obtaining 0.13 g (0.20 mmol, 67.7%) of the desired compound in the state of light yellowish white crystals.

mp: >250° C.

NMR (DMSO-$d_6$) δ: 10.71 (s, 1H), 10.23 (s, 1H), 8.65 (s, 1H), 8.31 (s, 1H), 8.01 (d, 2H), 7.82–7.77 (m, 2H), 7.64 (m, 4H), 7.60–7.20 (bs, 4H), 6.77 (d, 2H), 4.16 (d, 2H), 3.74 (s, 8H)

IR (KBr) cm$^{-1}$: 3310, 1652, 1517

Elemental analysis: (C$_{27}$H$_{28}$Cl$_2$N$_8$O$_2$·2HCl·H$_2$O) Calcd.: C:49.25, H:4.90, N:17.02, Cl:21.54 Found: C:49.30, H:4.70, N:16.91, Cl:21.61

EXAMPLE 10 (Compound 2004)

1H-2-[3-(guanidinoacetylamino)phenyl] benzimidazole-5-[N-[3-methyl-4-[N,N-bis(2-chloroethyl)amino]phenyl]]carboxyamide dihydrochloride Reaction 1

1H-2-[3-(nitrophenyl)benzimidazole-5-[N-[3-methyl-4-[N,N-bis(2-chloroethyl)amino]phenyl]] carboxyamide In 30 ml of DMF were dissolved 3.1 g (11 mmols) of 1H-2-(3-nitrophenyl)benzimidazole-5-carboxylic acid and 3.1 g (11 mmols, 1.0 eq.) of 3-methyl-4-[N,N-bis(2-chloroethyl)amino]aniline hydrochloride, and the solution was then stirred under a nitrogen gas stream while cooled on ice. Next, 2.5 ml (16 mmols, 1.5 eq.) of DECP and 4.6 ml (33 mmols, 3.0 eq.) of triethylamine were added in this order, and the solution was stirred at 0° C. for 30 minutes and at room temperature for 3 hours and then allowed to stand overnight. After the reaction solution was concentrated under reduced pressure, the resulting residue was dissolved in acetone. Next, silica gel was added thereto, and the solution was evaporated to dryness under reduced pressure and then purified through silica gel column chromatography (chloroform/methanol=8/2). After the solvents were distilled off under reduced pressure, the resulting residue was sludged with chloroform and a small amount of methanol. Next, the resulting powder was collected by filtration and then washed with methanol, thereby obtaining 4.2 g (yield=75%) of ocherous powder.

mp: A definite melting point was not present.

NMR (DMSO-d$_6$) δ: 10.22 (s, 0.5H), 10.16 (s, 0.5H), 9.06 (s, 1H), 8.66 (d, 1H), 8.42–8.36 (m, 1.5H), 8.17 (s, 0.5H), 7.93–7.62 (m, 5H), 7.24 (d, 1H), 3.57 (t, 4H), 3.39 (t, 4H), 2.31 (s, 3H)

Reaction 2

1H-2-[3-(guanidinoacetylamino)phenyl] benzimidazole-5-[N-[3-methyl-4-[N,N-bis(2-chloroethyl)amino]phenyl]]carboxyamide dihydrochloride In a mixed solvent of 5 ml of DMF and 5 ml of methanol, 0.40 g (0.78 mmol) of 1H-2-(3-nitrophenyl)benzimidazole-5-[N-[3-methyl-4-[N,N-bis(2-chloroethyl)amino]phenyl] carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 281 mg (2.3 mmols, 3 eq.) of guanidineacetic acid hydrochloride and 483 mg (2.3 mmols, 3 eq.) of DCC were added in this order. After stirring at 0° C. for 30 minutes, the solution was further stirred at room temperature for 6 hours and then allowed to stand overnight. Next, the resulting precipitate was removed by filtration and the solvents were distilled off from the resulting filtrate under reduced pressured. The resulting residue was purified through silica gel column chromatography (chloroform/methanol=95/5). After the solvents were distilled off under reduced pressure, the resulting residue was dissolved in methanol, and ether was then added to the solution, so that precipitation occurred again, thereby obtaining 155 mg (yield=34%) of white powder.

NMR (DMSO-d$_6$) δ: 10.83 (s, 1H), 10.44 (s, 1H), 8.68 (s, 1H), 8.37 (s, 1H), 8.09 (d, 2H), 7.89 (d, 1H), 7.82 (d, 1H), 7.73–7.63 (m, 3H), 7.44 (bs, 4H), 7.25 (d, 1H), 4.19 (d, 2H), 3.57 (t, 4H), 3.37 (t, 4H), 2.31 (s, H)

IR (KBr) cm$^{-1}$: 3348, 1665, 1504, 1308, 1263, 884

EXAMPLE 11 (Compound 2006)

1H-2-[3-(guanidinoacetylamino)phenyl] benzimidazole-5-[N-[3-chloro-4-[N,N-bis(2-chloroethyl)amino]phenyl]]carboxyamide dihydrochloride Reaction 1

1H-2-[3-(nitrophenyl)benzimidazole-5-[N-[3-chloro-4-[N,N-bis(2-chloroethyl)amino]phenyl]] carboxyamide In 7 ml of DMF was dissolved 0.60 g (2.12 mmols) of 1H-2-(3-nitrophenyl)benzimidazole-5-carboxylic acid, and the solution was then stirred under a nitrogen gas stream while cooled on ice. Afterward, 2.45 mmols of 3-chloro-4-[N,N-bis(2-chloroethyl)amino]aniline hydrochloride {which was synthesized from 0.73 g (2.45 mmols) of a corresponding nitro compound by catalytic hydrogenation} and 0.89 ml (6.38 mmols, 3.0 eq.) of triethylamine were added in this order, and 5 ml of DMF was further added. Next, 0.48 ml (3.16 mmols, 1.5 eq.) of DECP was additionally added, the solution was stirred for 6 hours and then allowed to stand overnight, as it was. After concentration under reduced pressure, the resulting residue was purified through silica gel column chromatography (chloroform/methanol=4%) and then crystallized from ethyl acetate. According to confirmation by NMR, the introduction of triethylamine hydrochloride was observed, and therefore, together with the resulting filtrate, the crystals were subjected to gel filtration (Sephadex LH-20, methanol). Next, solidification was accomplished with ether, thereby obtaining 0.48 g (0.90 mmol, 42.0%) of the desired compound in the state of ocherous solid.

mp: A definite melting point was not present.

NMR (DMSO-d$_6$) δ: 10.39 (s, 1H), 9.06 (s, 1H), 8.66 (d, 1H), 8.38 (d, 1H), 8.32 (s, 1H), 8.03 (d, 1H), 7.93–7.87 (m, 2H), 7.76 (d, 1H), 7.73 (dd, 1H), 7.37 (d, 1H), 3.64–3.48 (m, 8H)

Reaction 2

1H-2-[3-(guanidinoacetylamino)phenyl] benzimidazole-5-[N-[3-chloro-4-[N,N-bis(2-chloroethyl)amino]phenyl]]carboxyamide dihydrochloride In DMF-methanol, 0.21 g (0.40 mmol) of 1H-2-(3-nitrophenyl)benzimidazole-5-[N-[3-chloro-4-[N,N-bis(2-chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 0.18 g (1.17 mmols, 3.0 eq.) of guanidineacetic acid hydrochloride and 0.24 g (1.16 mmols, 3.0 eq.) of DCC were added in this order. Afterward, the temperature of the solution was returned to room temperature, and the solution was stirred for 2 hours and then allowed to stand overnight. After the removal of a formed solid by filtration, the filtrate was concentrated under reduced pressure. Next, the residue was subjected to gel filtration (Sephadex LH-20, methanol), and 4N hydrochloric acid and dioxane were added to the eluted fraction, followed by concentration. The concentrated material was solidified with ether, thereby obtaining 0.15 g (0.22 mmol, 55.7%) of the desired compound in the state of light yellowish white power.

mp: A definite melting point was not present.

NMR (DMSO-$d_6$) δ: 10.78 (s, 1H), 10.63 (s, 1H), 8.67 (s, 1H), 8.37 (s, 1H), 8.04 (m, 2H), 7.88–7.63 (m, 5H), 7.60–7.25 (bs, 4H), 7.37 (d, 1H), 4.18 (d, 2H), 3.62 (t, 4H), 3.51 (t, 4H)

IR (KBr) $cm^{-1}$: 3313, 1673, 1498, 1385, 1307, 1252

Elemental analysis: ($C_{27}H_{27}Cl_3N_8O_2 \cdot 2HCl \cdot 5H_2O$) Calcd.: C:42.40, H:5.14, N:14.65 Found: C:42.48, H:4.73, N:14.67

EXAMPLE 12 (Compound 2011)

1H-2-[3-[4-(guanidino)butyryl]amino]phenyl] benzimidazole-5-[N-[4-[N,N-bis(2-chloroethyl) amino)phenyl]]carboxyamide dihydrochloride In DMF-methanol, 0.20 g (0.40 mmol) of 1H-2-(3-nitrophenyl)benzimidazole-5-[N-[4-[N,N-bis(2-chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 0.22 g (1.21 mmols, 3.0 eq.) of guanidinobutyric acid hydrochloride and 0.25 g (1.21 mmols, 3.0 eq.) of DCC were added in this order. Afterward, the temperature of the solution was returned to room temperature, and the solution was stirred for 3 hours and then allowed to stand overnight. After the removal of a formed solid by filtration, the filtrate was concentrated under reduced pressure. Next, the residue was purified through silica gel column chromatography (ethyl acetate/IPA/water= 6/2/1) and then subjected to gel filtration (Sephadex LH-20, methanol), and 4N hydrochloric acid and dioxane were added to the eluted fraction, followed by concentration. The concentrated material was solidified with ether, thereby obtaining 0.10 g (0.15 mmol, 37.5%) of the desired compound in the state of yellow power (hygroscopic).

mp: A definite melting point was not present.

NMR (DMSO-$d_6$) δ: 10.59 (s, 1H), 10.32 (s, 1H), 8.69 (s, 1H), 8.36 (s, 1H), 8.10 (d, 1H), 8.05 (d, 1H), 7.95 (t, 1H), 7.87 (d, 1H), 7.79 (d, 1H), 7.65 (m, 3H), 7.50–7.00 (bs, 4H), 6.77 (d, 2H), 3.74 (s, 8H), 3.18 (q, 2H), 1.85 (m, 2H)

IR (KBr) $cm^{-1}$: 3164, 1655, 1517, 1330, 1247, 1182

Elemental analysis: ($C_{29}H_{32}Cl_2N_8O_2 \cdot 2HCl \cdot 3.3H_2O$) Calcd.: C:47.85, H:5.62, N:15.39, Cl:19.48 Found: C:47.95, H:5.49, N:15.10, Cl:19.35

EXAMPLE 13 (Compound 2014)

1H-2-[3-[[4-(guanidino)butyryl]amino]phenyl] benzimidazole-5-[N-[3-methyl-4-[N,N-bis(2-chloroethyl)amino]phenyl]]carboxyamide dihydrochloride In a mixed solvent of 5 ml of DMF and 5 ml of methanol, 0.40 g (0.78 mmol) of 1H-2-(3-nitrophenyl)benzimidazole-5-[N-[3-methyl-4-[N,N-bis(2-chloroethyl)amino]phenyl]] carboxyamide was subjected to catalytic hydrogenation using 10% Pd/C (wet) as a catalyst to lead it to a corresponding amino compound. Next, the DMF solution of this amino compound was stirred under a nitrogen gas stream while cooled on ice, and 426 mg (2.4 mmols, 3 eq.) of 4-guanidinobutyric acid hydrochloride and 450 mg (2.4 mmols, 3 eq.) of EDCI were added in this order. Afterward, the solution was stirred at 0° C. for 30 minutes and further at room temperature for 3 hours, and then allowed to stand overnight. The solvents were distilled under reduced pressure, and the resulting residue was then purified through silica gel column chromatography (ethyl acetate/IPA/water= 5/2/1). After the solvents were distilled off under reduced pressure, the resulting residue was dissolved in methanol and then further subjected to gel filtration column chromatography (Sephadex LH-20, methanol). After the solvents were distilled off under reduced pressure, the resulting residue was then sludged with acetone-IPA, thereby obtaining 113 mg (yield 21%) of the desired compound in the state of light yellow power.

NMR (DMSO-$d_6$) δ: 10.58 (s, 1H), 10.44 (s, 1H), 8.69 (s, 1H), 8.36 (s, 1H), 8.11–7.61 (m, 7H), 7.25 (bs, 4H), 7.25 (d, 1H), 4.03 (q, 1H), 3.57 (t, 4H), 3.37 (t, 4H), 3.26 (q, 2H), 2.50 (t, 2H), 2.31 (s, 3H), 1.84 (m, 2H)

IR (KBr) $cm^{-1}$: 3357, 1664, 1504, 1308, 1180, 886

EXAMPLE 14 (Compound 2016)

1H-2-[3-[[4-(guanidino)butyryl]amino]phenyl] benzimidazole-5-[N-[3-chloro-4-[N,N-bis(2-chloroethyl)amino]phenyl]]carboxyamide dihydrochloride In DMF-methanol, 0.31 g (0.58 mmol) of 1H-2-(3-nitrophenyl)benzimidazole-5-[N-[3-chloro-4-[N,N-bis(2-chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 0.32 g (1.76 mmols, 3.0 eq.) of guanidinobutyric acid hydrochloride and 0.36 g (1.74 mmols, 3.0 eq.) of DCC were added in this order. Afterward, the temperature of the solution was returned to room temperature, and the solution was stirred for 3 hours and then allowed to stand overnight. Since the material did not disappear the next day, 0.11 g 4-guanidinobutyric acid and 0.12 g of DCC were added, followed by stirring for further 2 hours. After the removal of a formed solid by filtration, the filtrate was concentrated under reduced pressure, and the resulting residue was then purified through silica gel column chromatography (ethyl acetate/IPA/water= 6/2/1) and then further subjected to gel filtration (Sephadex LH-20, methanol). Next, 4N hydrochloric acid and dioxane were added to the eluted fraction, followed by concentration. The residue was collected by scraping, thereby obtaining 73 mag (0.10 methanol, 17.9%) of the desired compound in the state of a white solid.

mp: A definite melting point was not present.

NMR (DMSO-$d_6$) δ: 10.37 (s, 1H), 10.29 (s, 1H), 8.59 (s, 1H), 8.29 (bs, 1H), 8.03 (s, 1H), 7.88–7.72 (m, 6H), 7.51 (t, 1H), 7.36 (d, 1H), 7.40–6.80 (bs, 4H), 3.62 (t, 4H), 3.50 (m, 4H), 3.19 (m, 2H), 2.46 (m, 2H), 1.84 (m, 2H)

IR (KBr) $cm^{-1}$: 3178, 1662, 1498, 1393, 1304

Elemental analysis: ($C_{29}H_{31}Cl_3N_8O_2 \cdot 2HCl \cdot 0.5H_2O$) Calcd.: C:48.93, H:4.81, N:15.74 Found: C:48.65, H:5.16, N:15.65

EXAMPLE 15 (Compound 2031)

1H-2-[3-[[4-(dimethylamino)butyryl]amino]phenyl] benzimidazole-5-[N-[4-[N,N-bis(2-chloroethyl) amino)phenyl]]carboxyamide dihydrochloride In DMF-methanol, 0.20 g (0.40 mmol) of 1H-2-(3-nitrophenyl)benzimidazole-5-[N-[4-[N,N-bis(2- chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 0.20 g (1.19 mmols, 3.0 eq.) of 4-dimethylaminobutyric acid hydrochloride and 0.25 g (1.21 mmols, 3.0 eq.) of DCC were added in this order. Afterward, the temperature of the solution was returned to room temperature, and the solution was stirred for 4.5 hours and then allowed to stand overnight. After the removal of a formed solid by filtration, the filtrate was concentrated under reduced pressure, and the resulting residue was then purified through silica gel column chromatography (ethyl acetate/IPA/water=5/2/1) and then further subjected to gel filtration (Sephadex LH-20, methanol). Since the presence of impurities was observed, the solution was subjected to silica gel column chromatography (ethyl acetate/methanol=1/1) again and then further subjected to gel filtration (Sephadex LH-20, methanol). Next, solidification was carried out with ether to obtain 89 mg (0.14 mmol, 34.0%) of the desired compound in the state of a light yellowish white solid.

mp: A definite melting point was not present.

NMR (DMSO-$d_6$) δ: 10.25 (s, 1H), 10.07 (s, 0.5H), 10.01 (s, 0.5H), 8.59 (s, 0.5H), 8.57 (s, 0.5H), 8.33 (s, 0.5H), 8.12 (s, 0.5H), 7.88–7.48 (m, 7H), 6.77 (d, 2H), 3.74 (s, 8H), 2.75 (m, 2H), 2.54 (s, 6H), 2.45 (s, 6H), 1.90 (m, 2H)

IR (KBr) cm$^{-1}$: 3214, 1614, 1518, 1328, 1244, 1182

Elemental analysis: ($C_{30}H_{34}Cl_2N_6O_2$·HCl·$H_2O$) Calcd.: C:56.65, H:5.86, N:13.21 Found: C:56.60, H:5.78, N:13.00

EXAMPLE 16 (Compound 2091)

1H-2-[3-[[3-(methylthio)propionyl]amino]phenyl]benzimidazole-5-[N-[4-[N,N-bis(2-chloroethyl)aminophenyl]]carboxyamide In a mixed solvent of 5 ml of DMF and 3 ml of methanol, 0.27 g (0.54 mmol) of 1H-2-(3-nitrophenyl)benzimidazole-5-[N-[4-[N,N-bis(2-chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 70 μl (0.68 mmol, 1.25 eq.) of 3-(methylthio)propionic acid and 0.13 g (0.63 mmol, 1.2 eq.) of DCC were added in this order. Afterward, the temperature of the solution was returned to room temperature, and the solution was stirred for 2.5 hours and then allowed to stand overnight. Since the progress of the reaction stopped the next day, 70 μl (0.68 mmol) of 3-(methylthio)propionic acid and 0.13 g (0.63 mmol) of DCC were added, and the solution was stirred for 10 hours and then allowed to stand overnight. After the removal of a formed solid by filtration, the filtrate was concentrated under reduced pressure, and the resulting residue was then purified through silica gel column chromatography (chloroform/methanol=4%) and then crystallized from ether, thereby obtaining 0.17 g (0.30 mmol, 55.2%) of the desired compound in the state of light yellowish white crystals.

mp: 142°–146° C.

NMR (DMSO-$d_6$) δ: 10.21 (s, 1H), 10.07 (s, 0.4H), 10.01 (s, 0.6H), 8.55 (m, 1H), 8.33 (s, 0.6H), 8.11 (s, 0.4H), 7.87–7.59 (m, 6H), 7.51 (t, 1H), 6.77 (d, 2H), 3.74 (s, 8H), 2.82–2.65 (m, 4H), 2.12 (s, 2H)

IR (KBr) cm$^{-1}$: 3259, 1644, 1518, 1327, 1248, 1181, 814

Elemental analysis: ($C_{28}H_{29}Cl_2N_6O_2$·$H_2O$) Calcd.: C:57.14, H:5.31, N:11.90 Found: C:57.09, H:5.40, N:11.67

EXAMPLE 17 (Compound 2041)

2-[N-[3-[5-[N-[4-[N,N-bis(2-chloroethyl)amino]phenyl nyl]carbamoyl]-1H-benzimidazole-2-yl]phenyl]]carbamoylethyl-dimethylsulfonium iodide 0.10 g (0.18 mmol) of 1H-2-[3-[[3-(methylthio)propionyl]amino]phenyl]benzimidazole-5-[N-[4-[N,N-bis(2-chloroethyl)amino)phenyl]]carboxyamide was dissolved in a mixture of 0.5 ml of 80% formic acid, 0.25 ml of acetic acid and 0.2 ml of methyl iodide, and the solution was then stirred at room temperature for 9 hours under shading and then allowed to stand overnight. After concentration under reduced pressure, the resulting residue was subjected to gel filtration (Sephadex LH-20, methanol, carried out twice) and then solidified with ether to obtain 47 mg (0.07 mmol, 36.6%) of the desired compound in the state of light yellowish white powder.

mp: A definite melting point was not present.

NMR (DMSO-$d_6$) δ: 10.49 (s, 1H), 10.05 (s, 1H), 8.58 (s, 1H), 8.24 (s, 1H), 7.87 (m, 2H), 7.70–7.47 (m, 5H), 6.77 (d, 2H), 3.74 (s, 8H), 3.57 (t, 2H), 3.04 (t, 2H), 2.97 (s, 6H)

IR (KBr) cm$^{-1}$: 3407, 1645, 1614, 1517, 1328, 1249, 1181

Elemental analysis: ($C_{29}H_{32}Cl_2IN_5O_2S$·HCl) Calcd.: C:46.51, H:4.44, N:9.35 Found: C:46.20, H:4.24, N:9.08

EXAMPLE 18 (Compound 2092)

1H-2-[3-[[3-(methylthio)propionyl]amino]phenyl]benzimidazole-5-[N-[3-methyl-4-[N,N-bis(2-chloroethyl)amino]phenyl]]carboxyamide In a mixed solvent of 5 ml of DMF and 5 ml of methanol, 0.40 g (0.78 mmol) of 1H-2-(3-nitrophenyl)benzimidazole-5-[N-[3-methyl-4-[N,N-bis(2-chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 281 mg (2.3 mmols, 3 eq.) of 3-(methylthio)propionic acid and 483 mg (2.3 mmols, 3 eq.) of DCC were added in this order. Afterward, the solution was stirred at 0° C. for 30 minutes and further at room temperature for 6 hours and then allowed to stand overnight. After the resulting precipitate was removed by filtration, the solvents were distilled off under reduced pressure, and the resulting residue was then purified through silica gel column chromatography (chloroform/methanol=95/5). After the solvents were distilled off under reduced pressure, the resulting residue was dissolved in methanol, and ether was then added, so that precipitation occurred again, thereby obtaining 155 mg (yield=34%) of the desired compound in the state of white powder.

NMR (DMSO-$d_6$) δ: 10.21 (s, 1H), 10.16 (s, 1H), 8.57 (s, 1H), 8.24 (bs, 1H), 7.86 (d, 2H), 7.72–7.49 (m, 5H), 7.24 (d, 1H), 3.57 (t, 4H), 3.36 (t, 4H), 2.80 (t, 2H), 2.68 (t, 2H), 2.37 (s, 3H), 2.12 (s, 3H)

EXAMPLE 19 (Compound 2044)

2-[N-[3-[5-[N-[3-methyl-4-[N,N-bis(2-chloroethyl)amino]phenyl]carbamoyl]-1H benzimidazole-2-yl]phenyl]]carbamoylethyl-dimethylsulfonium iodide 0.10 g (0.17 mmol) of 1H-2-[3-[[3-(methylthio)propionyl]amino]phenyl]benzimidazole-5-[N-[3-methyl-4-[N,N-bis(2-chloroethyl)amino]phenyl]]carboxyamide was dissolved in a mixture of 0.6 ml of 80% formic acid, 0.3 ml of acetic acid and 0.5 ml of methyl iodide, and the solution was then stirred at room temperature for 3 hours under shading and then allowed to stand overnight. After concentration under reduced pressure, the resulting residue was purified through gel filtration column chromatography (Sephadex LH-20, methanol, carried out twice). The solvents were distilled off under reduced pressure, and the resulting residue was dissolved in methanol. Afterward, IPA was added to the solution, so that precipitation occurred again, thereby obtaining 58 mg (yield=47%) of the desired compound in the state of light yellow powder.

NMR (DMSO-$d_6$) δ: 10.56 (s, 1H), 10.20 (s, 1H), 8.59 (s, 1H), 8.27 (s, 1H), 7.91 (d, 2H), 7.78–7.55 (m, 5H), 7.24 (d, 1H), 3.57 (t, 4H), 3.37 (t, 4H), 3.21 (t, 2H), 3.05 (t, 2H), 2.97 (s, 6H), 2.31 (s, 3H)

IR (KBr) cm−1: 3422, 1654, 1502, 1313, 1118, 885

EXAMPLE 20 (Compound 2093)

1H-2-[3-[3-(methylthio)propionylamino]phenyl]benzimidazole-5-[N-[3-chloro-4-[N,N-bis(2-chloroethyl)amino]phenyl]]carboxyamide In DMF-methanol, 0.21 g (0.40 mmol) of 1H-2-(3-nitrophenyl)benzimidazole-5-[N-[3-chloro-4-[N,N-bis(2-chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 0.12 ml (1.16 mmols, 2.9 eq.) of 3-methylthiopropionic acid and 0.24 g (1.16 mmols, 2.9 eq.) of DCC were added in this order. Afterward, the temperature of the solution was returned to room temperature, and the solution was stirred for 2 hours and then allowed to stand overnight. After the removal of a formed solid by filtration, the filtrate was concentrated under reduced pressure, and the resulting residue was subjected to silica gel column chromatography (chloroform/methanol= 4%) and then solidified with ether, thereby obtaining 0.18 g (0.30 mmol, 75.3%) of the desired compound in the state of light yellowish white powder.

mp: A definite melting point was not present.

NMR (DMSO-$d_6$) δ: 10.36 (s, 1H), 10.23 (s, 1H), 8.58 (s, 1H), 8.25 (s, 1H), 8.02 (d, 1H), 7.85 (d, 2H), 7.75–769 (m, 2H), 7.52 (t, 1H), 7.37 (d, 1H), 3.62 (t, 4H), 3.50 (t, 4H), 2.80 (t, 2H), 2.68 (t, 2H)

EXAMPLE 21 (Compound 2046)

2-[N-[3-[5-[N-[3-chloro-4-[N,N-bis(2-chloroethyl)amino]phenyl]carbamoyl]-1H-benzimidazole-2-yl]phenyl]carbamoylethyl]dimethylsulfonium iodide 0.10 g (0.17 mmol) of 1H-2-[3-(3-methylthiopropionylamino)phenyl]benzimidazole-5-[N-[3-chloro-4-[N,N-bis(2-chloroethyl)amino]phenyl]]carboxyamide was dissolved in a mixture of 0.5 ml of 85% formic acid and 0.25 ml of acetic acid, and 0.2 ml of methyl iodide was then added, followed by stirring at room temperature for 3 days under shading. After concentration under reduced pressure, the resulting residue was subjected to gel filtration (Sephadex LH-20, methanol), and then solidified with ether, thereby obtaining 0.10 g (0.13 mmol, 81.2%) of the desired compound in the state of light yellowish white powder.

mp: A definite melting point was not present.

NMR (DMSO-$d_6$) δ: 10.48 (s, 1H), 10.35 (s, 1H), 8.58 (s, 1H), 8.25 (s, 1H), 8.02 (s, 1H), 7.86 (m, 2H), 7.71 (m, 3H), 7.55 (t, 1H), 7.36 (d, 1H), 3.64–3.48 (m, 8H), 3.03 (t, 2H), 2.97 (s, 6H)

IR (KBr) cm−1: 3248, 1655, 1577, 1497, 1389, 1307

Elemental analysis: ($C_{29}H_{31}Cl_3IN_5O_3S.2.5H_2O$) Calcd.: C:43.98, H:4.58, N:8.84 Found: C:44.00, H:4.26, N:8.62

EXAMPLE 22 (Compound 2051)

1H-2-[3-[(3-morpholinopropionyl)amino]phenyl]benzimidazole-5-[N-[4-[N,N-bis(2-chloroethyl)amino]phenyl]]carboxyamide hydrochloride In DMF-methanol, 0.51 g (1.02 mmols) of 1H-2-(3-nitrophenyl)benzimidazole-5-[N-[4-[N,N-bis(2-chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 0.21 ml (1.51 mmols, 1.5 eq.) of triethylamine and a chloroform solution containing 1.53 mmols of 3-morpholinopropionyl chloride {which was prepared from 0.30 g (1.53 mmols) of 3-morpholinopropionic acid and 1 ml of thionyl chloride in chloroform} were added in this order. Afterward, the temperature of the solution was returned to room temperature, and the solution was stirred for 3 hours and then allowed to stand overnight. Since the material did not disappear the next day, the chloroform solution containing 1.53 mmols of 3-morpholinopropionyl chloride was further added. After stirring for 9 hours, the solution was concentrated under reduced pressure, and the resulting residue was subjected to silica gel column chromatography (chloroform/methanol= 8–12%). Next, the eluted fraction was concentrated, and methanol was then added. Afterward, the resulting solid was collected by filtration to obtain 0.18 g (0.28 mmol, 27.3%) of the desired compound in the state of light yellowish white powder. Furthermore, the filtrate was subjected to gel filtration (Sephadex LH-20, methanol) and then solidified with ether, thereby obtaining 0.11 g (0.17 mmol, 16.7%) of the desired compound in the state of white powder (total yield= 44.0%).

mp: A definite melting point was not present.

NMR (DMSO-$d_6$) δ: 10.30 (s, 1H), 10.08 (s, 0.4H), 10.01 (s, 0.6H), 8.57 (s, 0.4H), 8.54 (s, 0.6H), 8.33 (s, 0.6H), 8.12 (s, 0.4H), 7.88–7.47 (m, 7H), 6.77 (d, 2H), 3.74 (s, 8H), 3.60 (m, 4H), 2.67 (m, 2H), 2.55–2.44 (m, 6H)

IR (KBr) cm−1: 3120, 1622, 1591, 1519, 1341, 1183, 1115

Elemental analysis: ($C_{31}H_{34}Cl_2N_6O_3.HCl.4H_2O$) Calcd.: C:51.85, H:6.04, N:11.70 Found: C:51.81, H:6.22, N:12.12

EXAMPLE 23 (Compound 2053)

1H-2-[3-[(3-morpholinopropionyl)amino]phenyl]benzimidazole-5-[N-[4-[N,N-bis(2-chloroethyl)]amino-3-methyl]phenyl]carboxyamide hydrochloride In a mixed solvent of 10 ml of DMF and 10 ml of methanol was dissolved 0.50 g (1.00 mmol) of 1H-2-(3-nitrophenyl)benzimidazole-5-[N-[4-[N,N-bis(2-chloroethyl)amino-3-methyl]phenyl]carboxyamide, and catalytic hydrogenation was then carried out under a nitrogen atmosphere in the presence of 10% Pd/C as a catalyst to lead the above-mentioned compound to a corresponding amino compound. Next, the DMF solution of this amino compound was stirred under a nitrogen gas stream while cooled on ice, and 0.59 ml (3.0 mmols) of morpholinoethylcarboxylic acid hydrochloride and 0.62 g (3.00 mmols) of DCC were added in this order. Afterward, the temperature of the solution was returned to room temperature, and the solution was then allowed to stand overnight. After the reaction, the reaction solution was concentrated under reduced pressure, and the resulting brown syrup-like residue was purified through silica gel column chromatography (chloroform/methanol=20/1–10/1). Next, the resulting fluorescent fraction was taken out, concentrated, and then sludged with ether/chloroform to obtain 0.25 g (0.38 mmol, 38.0%) of the desired compound in the state of white powder.

mp: A definite melting point was not present.

NMR (DMSO-$d_6$) δ: 10.25 (s, 1H), 10.18 (s, 0.5H), 10.13 (s, 0.5H), 8.55 (d, 1H), 3.34 (s, 0.5H), 8.12 (s, 0.5H), 7.88–7.48 (m, 7H), 7.24 (d, 1H), 3.61–3.50 (m, 8H), 3.64 (t, 4H), 2.67 (t, 2H), 2.54 (t, 2H), 2.43 (bs, 4H), 2.31 (s, 3H)

IR (KBr) cm$^{-1}$: 3258, 2963, 1648, 1502, 1446, 1314,

EXAMPLE 24 (Compound 2054)

1H-2-[3-[(3-morpholinopropionyl)amino]phenyl]benzimidazole-5-[N-[3-chloro-4-[N-bis(2-chloroethyl)amino]phenyl]]carboxyamide hydrochloride In DMF-methanol, 0.30 g (0.56 mmol) of 1H-2-(3-nitrophenyl)benzimidazole-5-[N-[3-chloro-4-[N,N-bis(2-chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 0.16 ml (1.15 mmols, 2.0 eq.) of triethylamine and a chloroform solution containing 1.13 mmols of 3-morpholinopropionyl chloride {which was prepared from 0.22 g (1.13 mmols) of 3-morpholinopropionic acid and 1 ml of thionyl chloride in chloroform} were added in this order. Afterward, the temperature of the solution was returned to room temperature, followed by stirring. After 3 hours, 0.16 ml (1.15 mmols) of triethylamine and the chloroform solution containing 1.13 mmols of 3-morpholinopropionyl chloride were further added, and the solution was then allowed to stand overnight. After concentration under reduced pressure, the resulting residue was subjected to silica gel column chromatography (chloroform/methanol=12%). The eluted fraction was further subjected to gel filtration (Sephadex LH-20, methanol), and 4N hydrochloric acid and dioxane were added, followed by concentration. Next, solidification was accomplished with a small amount of ethanolether, thereby obtaining 0.13 g (0.18 mmol, 32.4%) of the desired compound in the state of light yellowish white amorphous powder.

mp: A definite melting point was not present.

NMR (DMSO-$d_6$) δ: 10.80 (s, 1H), 10.61 (s, 1H), 8.62 (s, 1H), 8.37 (s, 1H), 8.04 (m, 3H), 7.87–7.73 (m, 3H), 7.64 (t, 1H), 7.37 (d, 1H), 3.87–3.79 (m, 4H), 3.62 (t, 4H), 3.51 (t, 4H), 3.44 (m, 4H), 3.06 (m, 4H)

IR (KBr) cm$^{-1}$: 3214, 1671, 1576, 1497, 1394, 1307, 1128, 1087

Elemental analysis: ($C_{31}H_{33}Cl_3N_6O_3 \cdot HCl \cdot 6.5H_2O$) Calcd.: C:46.69, H:5.94, N:10.54 Found: C:46.53, H:5.95, N:10.45

EXAMPLE 25 (Compound 2061)

1H-2-[3-(3-pyridylacetylamino)phenyl]benzimidazole-5-[N-[4-[N,N-bis(2-chloroethyl)amino]phenyl]carboxyamide In DMF-methanol, 0.40 g (0.80 mmol) of 1H-2-(3-nitrophenyl)benzimidazole-5-[N-(4-[N,N-bis(2-chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 0.21 g (1.21 mmols, 1.5 eq.) of 3-pyridylacetic acid hydrochloride and 0.23 g (1.20 mmols, 1.5 eq) of EDCI were added in this order. Afterward, the temperature of the solution was returned to room temperature, followed by stirring for 2.5 hours. After concentration under reduced pressure, the resulting residue was subjected to silica gel column chromatography (chloroform/methanol=8%), and then solidified with ether. Since some impurities were contained in the powder, a separating operation was carried out by the use of chloroform and dilute ammonia water to precipitate insolubles. Next, the insolubles were collected by filtration to obtain 49 mg (0.083 mmol, 10.4%) of the desired compound in the state of light brown solid. Furthermore, the resulting chloroform layer was concentrated, and then solidified with ether, thereby obtaining 65 mg (0.10 mmol, 12.5%) of the desired hydrochloride in the state of light brown powder.

mp: A definite melting point was not present.

Free form: NMR (DMSO-$d_6$) δ: 10.47 (s, 1H), 10.00 (s, 0.5H), 8.57 (s, 1H), 8.55 (d, 1H), 8.48 (d, 1H), 8.32 (s, 0.5H), 8.10 (s, 0.5H), 7.87–7.49 (m, 8H), 7.38 (t, 1H), 6.77 (d, 2H), 3.77 (s, 2H), 3.73 (s, 8H)

Hydrochloride: NMR (DMSO-$d_6$) δ: 10.52 (s, 1H), 10.03 (s, 1H), 8.62 (s, 1H), 8.54 (m, 2H), 8.22 (s, 1H), 7.91–7.84 (m, 3H), 7.72–7.62 (m, 4H), 7.55–7.45 (m, 2H), 6.77 (d, 2H), 3.81 (s, 2H), 3.73 (s, 8H)

IR (KBr) cm$^{-1}$: 3070, 1617, 1518, 1328, 1184, 1141

Elemental analysis (free form): ($C_{31}H_{28}Cl_2N_6O_2 \cdot 2.5H_2O$) Calcd.: C:58.86, H:5.26, N:13.29 Found: C:58.86, H:5.44, N:13.28

EXAMPLE 26 (Compound 2063)

1H-2-[3-(3-pyridylacetylamino)phenyl]benzimidazole-5-[N-[3-methyl-4-[N,N-bis(2-chloroethyl)amino]phenyl]]carboxyamide In 10 ml of a mixed solvent of DMF:methanol=1:1, 0.40 g (0.80 mmol) of 1H-2-(3-nitrophenyl)benzimidazole-5-[N-[3-methyl-4-[N,N-bis(2-chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 0.4 g (2.3 mmols, 3 eq.) of 3-pyridylacetic acid hydrochloride and 0.45 g (2.4 mmols, 3 eq) of EDCI were added in this order, followed by stirring for 30 minutes as it was. After stirred at room temperature for further 3 hours, the solution was allowed to stand overnight. After the solvents were distilled off under reduced pressure, the resulting residue was purified through silica gel column chromatography (chloroform/methanol=95/5). The solvents were distilled off, and the residue was then dissolved in methanol. Next, isopropyl ether was added, so that precipitation occurred again, to obtain 153 mg (yield=33%) of white powder.

NMR (DMSO-$d_6$) δ: 10.48 (s, 1H), 10.18 (bs, 0.5H), 10.13 (bs, 0.5H), 8.61–7.36 (m, 13H), 7.23 (d, 1H), 3.77 (s, 2H), 3.59 (t, 4H), 3.36 (t, 4H), 2.31 (s, 3H)

IR (KBr) cm$^{-1}$: 3348, 1665, 1504, 1308, 1263, 884

EXAMPLE 27 (Compound 2064)

1H-2-[3-(3-pyridylacetylamino)phenyl]benzimidazole-5-[N-[3-chloro-4-[N,N-bis(2-chloroethyl)amino]phenyl]]carboxyamide In DMF-methanol, 0.40 g (0.75 mmol) of 1H-2-(3-nitrophenyl)benzimidazole-5-[N-[3-chloro-4-[N,N-bis(2- chloroethyl)amino]phenyl]]carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 0.21 g (1.21 mmols, 1.6 eq.) of 3-pyridylacetic acid and 0.22 g (1.15 mmols, 1.5 eq) of EDCI were added in this order. Afterward, the temperature of the solution was returned to room temperature, followed by stirring for 3.5 hours. After concentration under reduced pressure, the resulting residue was subjected to a separating operation by the use of chloroform and water to precipitate gel-like insolubles. Next, the resulting aqueous layer was adjusted to a pH of about 11 with an aqueous sodium hydroxide solution and then extracted with chloroform twice. The obtained chloroform layers were joined to each other, dried over anhydrous sodium sulfate, and then concentrated under reduced pressure. Afterward, the residue was solidified with ether, thereby obtaining 96 mg (0.15 mmol, 20.6%) of the desired hydrochloride in the state of light brown powder.

mp: A definite melting point was not present.

NMR (DMSO-$d_6$) δ: 10.47 (s, 1H), 10.37 (s, 0.4H), 10.31 (s, 0.6H), 8.57 (s, 1H), 8.48 (d, 1H), 8.34 (s, 0.6H), 8.11 (s, 0.4H), 8.02 (s, 1H), 7.87–7.61 (m, 7H), 7.52 (t, 1H), 7.40–7.35 (m, 2H), 3.77 (s, 2H), 3.61 (t, 4H), 3.50 (t, 4H)

IR (KBr) cm$^{-1}$: 3191, 1631, 1582, 1498, 1390, 1309

EXAMPLE 28 (Compound 2073)

1H-2-[3-(4-pyridylacetylamino)phenyl]
benzimidazole-5-[N-[3-methyl-4-[N,N-bis(2-
chloroethyl)amino]phenyl]]carboxyamide In 10 ml of a mixed solvent of DMF:methanol=1:1, 0.40 g (0.80 mmol) of 1H-2-(3-nitrophenyl)benzimidazole-5-[N-[3-methyl-4-[N,N-bis(2-chloroethyl)amino]phenyl]] carboxyamide was subjected to catalytic hydrogenation using 10% Pd/C as a catalyst to lead it to a corresponding amino compound. Next, the DMF solution of this amino compound was stirred under a nitrogen gas stream while cooled on ice, and 0.4 g (2.3 mmols, 3 eq.) of 4-pyridylacetic acid hydrochloride and 0.45 g (2.4 mmols, 3 eq) of EDCI were added in this order, followed by stirring for 30 minutes as it was. After stirred at room temperature for additional 6 hours, the solution was allowed to stand overnight. After the solvents were distilled off under reduced pressure, the resulting residue was purified through silica gel column chromatography (chloroform/methanol=6/1). The solvents were distilled off, and the residue was further purified through silica gel column chromatography (chloroform/methanol=8/1). The solvents were distilled off, and the residue was then dissolved in methanol. Next, isopropyl ether was added, so that precipitation occurred again, to obtain 50 mg (yield=11%) of light yellow powder.

NMR (DMSO-$d_6$) δ: 10.51 (s, 1H), 10.18 (bs, 0.5H), 10.13 (bs, 0.5H), 8.61 (s, 1H), 8.55 (d, 2H), 8.33 (s, 0.5H), 8.11 (s, 0.5H), 7.89–7.49 (m, 7H), 7.39 (d, 2H), 7.23 (d, 1H), 3.77 (s, 2H), 3.57 (t, 4H), 3.36 (t, 4H), 2.31 (s, 3H)

IR (KBr) cm$^{-1}$: 3422, 1647, 1508, 1318, 1239, 829

Formulation Example 1

| | |
|---|---|
| Compound No. 2053 as an active ingredient | 30 g |
| Lactose | 68 g |
| Crystalline cellulose | 20 g |
| Magnesium stearate | 2 g |

The components described above are mixed in the above composition and the resulting mixture was formulated into core tablets by a tableting machine. Each of the core tablets weighed 120 mg containing 30 mg of Compound No. 2053 and had a diameter of 7 mm.

Talc was then sprinkled on each core tablet and the surface having talc was then coated with varnish to form an undercoat. Additional varnish coating was repeated so as to obtain tablets suitable for the internal uses. Color coating was further conducted. After drying, the tablets having the color coats were waxed and polished into tablets of uniform gloss.

Formulation Example 2

As an active ingredient, 1 g of Compound No. 2053 was weighed and dissolved in 1,000 ml of sterilized propylene glycol. The resting solution was poured and enclosed in ampoules so as to obtain injections in ampoules, each of which contained 5 ml of the solution.

Test Example 1

Investigation was made on the linkage of each compound to DNA. The test was carried out by comparing a Tm value in the case that the compound was added to the DNA solution with a Tm value in the case that no compound was added thereto.

That is to say, poly d(A-T)-d(A-T) was used as the DNA. This DNA was dissolved in a buffer solution and the compound was further added thereto, and the Tm value was then measured. On the other hand, the Tm of the DNA alone was measured, and a difference (ΔTm) was then calculated. For the measurement, a U-3200 model spectrophotometer made by Hitachi, Ltd. was used, and for the control of temperature, SPR-10 model made by Hitachi, Ltd. was used.

The ΔTm of Compound 2001 was obtained, and it was 14° C.

Test Example 2

The anticancer activity of each compound will be described. Table 2 shows the anti-tumor activity of the typical compounds. This test was carried out by measuring an in vitro inhibitory activity on tumor cell growth. That is to say, the B16 melanoma cells of a mouse were planted on a culture plate having 96 cells, and a compound was then added after one day and the cells were cultured at 37° C. for 3 days in 5% $CO_2$. Next, a compound concentration ($IC_{50}$) necessary to accomplish a 50% growth inhibitory effect was determined in accordance with a procedure described in Cancer. Res., Vol. 48, p. 589–601 (1988). The unit of the drug concentration was μg/ml. The result of distamycin is also simultaneously shown as a comparative example.

TABLE 2

| Compound No. | Anti-tumor activity IC$_{50}$ (ug/ml) |
|---|---|
| 2 | 0.58 |
| 29 | 3.05 |
| 47 | 0.38 |
| 1001 | 0.36 |
| 1010 | 3.19 |
| 2001 | 0.82 |
| 2004 | 0.53 |
| 2006 | 0.65 |
| 2011 | 0.97 |
| 2014 | 1.18 |
| 2016 | 2.08 |
| 2031 | 1.56 |
| 2041 | 0.37 |
| 2044 | 0.72 |
| 2046 | 0.39 |
| 2051 | 0.49 |
| 2053 | 0.33 |
| 2054 | 0.41 |
| 2063 | 3.48 |
| 2073 | 1.19 |
| Distamycin | 36 |

Test Example 3

A cell floating solution having 1×10$^7$ mouse colon cancer cells of Colon 26 per ml of HBSS (Hanks' Balanced Salt Solution) was prepared. Next, 0.1 ml of this cell floating solution was implanted in the side abdomen hypodermis of a female CDF1 mouse (0 day). On the day after the tumor implantation (1st day), the weight of the mouse was measured, and a solution of a compound (a 5% glucose solution containing 5% Tween 80) was administered into the tail vein of the mouse. On the 15th day, the tumor was extracted, and its weight was then measured.

An average tumor weight ratio of each experimental sample was calculated as a T/C value on the assumption that the average tumor weight ratio of a control to which any compound was not administered was 100%.

Table 3 shows the results of the test. The T/C values correspond to compound numbers, respectively, and each value in the parentheses represents the concentration of the drug at the time when its T/C value was obtained.

TABLE 3

| Compound No. | T/C (%) | Dose (mg/kg) |
|---|---|---|
| 2001 | 13 | 30 |
| 2006 | 21 | 10 |
| Adriamycin | 29 | 20 |

What is claimed is:

1. A compound represented by the following formula (1) or its pharmacologically acceptable salt:

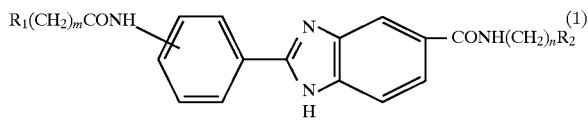

wherein each of m and n is independently an integer of from 0 to 5; each of R$_1$ and R$_2$ is independently a hydrogen atom, a halogen atom, an alkylthio group having 1 to 8 carbon atoms, an amino group which is optionally substituted, an ammonium group which is optionally substituted, a sulfonium group which is optionally substituted, a phenyl group which is optionally substituted with only members selected from the group consisting of a halogen atom, a straight-chain alkoxy group having 1 to 3 carbon atoms, a branched alkoxy group having 1 to 3 carbon atoms, an alkoxycarbonyl group having 2 to 4 carbon atoms, a trifluoromethyl group, a cyano group, an amidino group, a guanidino group and a dialkylamino group in which the alkyl groups have 1 to 3 carbon atoms, a hetero-five-membered ring group which is optionally substituted, a hetero-six-membered ring group which is optionally substituted, an amidino group, a guanidino group, an amino acid residue or a group represented by the formula (2)

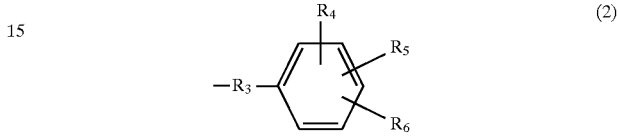

wherein R$_3$ is a direct bond or an oxygen atom with the proviso that when R$_3$ is an oxygen atom, m or n of (CH$_2$)$_m$ or —(CH$_2$)$_n$ to which R$_3$ bonds is not 0; R$_4$ is a hydrogen atom, an alkyl group having 1 to 8 carbon atoms, an alkoxy group having 1 to 8 carbon atoms, a halogen atom, a trifluoromethyl group, a cyano group, an amidino group, a carboxyl group or —COR$_7$ wherein R$_7$ is an alkylamino group having 1 to 8 carbon atoms which is optionally substituted by a substituted amino group, an amino group which is optionally substituted by a phenyl group which is optionally substituted, or a benzylamino group which is optionally substituted; R$_5$ is a hydrogen atom, an alkyl group having 1 to 8 carbon atoms, an alkoxy group having 1 to 8 carbon atoms or a halogen atom; R$_6$ is a —(CH$_2$)$_p$N(R$_8$)$_2$ or —(CH$_2$)$_p$NR$_8$R$_9$ wherein p is an integer of from 0 to 5; R$_8$ is —CH$_2$CH$_2$W wherein W is a halogen atom, a hydroxyl group, a mesyloxy group or a tosyloxy group or —OCOR$_7$ wherein R$_7$ is defined above; R$_9$ is an alkyl group having 1 to 5 carbon atoms or a mesyl group;

the phenyl group having a R$_1$(CH$_2$)$_m$CONH group in the formula (1) is optionally substituted by the R$_1$(CH$_2$)$_m$CONH group at any position of the phenyl group with the proviso that when m is 1, R$_1$ is not a hydrogen atom; and wherein R$_2$ is not hydrogen.

2. The compound or its pharmacologically acceptable salt according to claim 1 herein R$_1$ is a halogen atom or a group represented by the formula (2).

3. The compound or its pharmacologically acceptable salt according to claim 1 wherein R$_2$ is a halogen atom or a group represented by the formula (2).

4. The compound or its pharmacologically acceptable salt according to claim 2 wherein R$_2$ is an amino group which is optionally substituted, a guanidino group or an amidino group.

5. The compound or its pharmacologically acceptable salt according to claim 3 wherein R$_1$ is an amino group which is optionally substituted, a guanidino group or an amidino group.

6. An anticancer composition which contains, as an active ingredient, a compound or its pharmacologically acceptable salt described in claim 5.

7. An antimicrobial composition which contains, as an active ingredient, a compound or its pharmacologically acceptable salt described in claim 5.

8. An antiviral composition which contains, as an active ingredient, a compound or its pharmacologically acceptable salt described in claim 5.

9. The compound or its pharmacologically acceptable salt according to claim 1 wherein the alkylthio group of R$_1$ R$_2$ has 1 to 4 carbon atoms.

10. The compound or its pharmacologically acceptable salt according to claim 1 wherein the phenyl group having a $R_1(CH_2)_m CONH$ group in the formula (1) is substituted by the $R_1(CH_2)_m CONH$ group in the 3-position or the 4-position of the phenyl group.

11. The compound or its pharmacologically acceptable salt according to claim 1 wherein $R_1$ is $NH_2C(=NH)NH-$ and m is 1.

12. The compound or its pharmacologically acceptable salt according to claim 11 wherein $R_2$ is

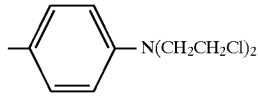

and n is 0.

13. An anticancer composition which contains, as an active ingredient, a compound or its pharmacologically acceptable salt described in claim 4.

14. An anticancer composition which contains, as an active ingredient, a compound or its pharmacologically acceptable salt described in claim 3.

15. An anticancer composition which contains, as an active ingredient, a compound or its pharmacologically acceptable salt described in claim 2.

16. An anticancer composition which contains, as an active ingredient, a compound or its pharmacologically acceptable salt described in claim 1.

17. An antimicrobial composition which contains, as an active ingredient, a compound or its pharmacologically acceptable salt described in claim 4.

18. An antimicrobial composition which contains, as an active ingredient, a compound or its pharmacologically acceptable salt described in claim 3.

19. An antimicrobial composition which contains, as an active ingredient, a compound or its pharmacologically acceptable salt described in claim 2.

20. An antimicrobial composition which contains, as an active ingredient, a compound or its pharmacologically acceptable salt described in claim 1.

21. An antiviral composition which contains, as an active ingredient, a compound or its pharmacologically acceptable salt described in claim 4.

22. An antiviral composition which contains, as an active ingredient, a compound or its pharmacologically acceptable salt described in claim 3.

23. An antiviral composition which contains, as an active ingredient, a compound or its pharmacologically acceptable salt described in claim 2.

24. An antiviral composition which contains, as an active ingredient, a compound or its pharmacologically acceptable salt described in claim 1.

25. A process of preparing a material selected from the group consisting of an anticancer agent, an antimicrobial agent and an antiviral agent by forming a compound or its pharmacologically acceptable salt as described in claim 5 into a dosage form suitable for administration.

26. A process of preparing a material selected from the group consisting of an anticancer agent, an antimicrobial agent and an antiviral agent by forming a compound or its pharmacologically acceptable salt as described in claim 4 into a dosage form suitable for administration.

27. A process of preparing a material selected from the group consisting of an anticancer agent, an antimicrobial agent and an antiviral agent by forming a compound or its pharmacologically acceptable salt as described in claim 3 into a dosage form suitable for administration.

28. A process of preparing a material selected from the group consisting of an anticancer agent, an antimicrobial agent and an antiviral agent by forming a compound or its pharmacologically acceptable salt as described in claim 2 into a dosage form suitable for administration.

29. A process of preparing a material selected from the group consisting of an anticancer agent, an antimicrobial agent and an antiviral agent by forming a compound or its pharmacologically acceptable salt as described in claim 4 into a dosage form suitable for administration.

* * * * *

UNITED STATES PATENT AND TRADEMARK OFFICE
CERTIFICATE OF CORRECTION

PATENT NO. : 5,821,258
DATED : October 13, 1998
INVENTOR(S) : Akio Matsunaga et al.

It is certified that error appears in the above-identified patent and that said Letters Patent is hereby corrected as shown below:

On the title page, under item [56]:

In the Other Publications Section, third article, first line, delete "Distamyci" and insert --Distamycin--.

In claim 2, column 102, line 44, delete "herein" and insert --wherein--.

In claim 9, column 102, line 66, between $R_1$ and $R_2$ insert --or--.

Signed and Sealed this

Twentieth Day of July, 1999

Attest:

Q. TODD DICKINSON

*Attesting Officer*     *Acting Commissioner of Patents and Trademarks*